United States Patent
Liou et al.

(10) Patent No.: US 10,246,455 B2
(45) Date of Patent: Apr. 2, 2019

(54) HISTONE DEACETYLASE INHIBITORS

(71) Applicants: Taipei Medical University, Taipei (TW); National Health Research Institutes, Zhunan (TW)

(72) Inventors: Jing-Ping Liou, Taipei (TW); Jang-Yang Chang, Taipei (TW); Jia-Yi Wang, Taipei (TW); Yun Yen, Arcadia, CA (US)

(73) Assignees: Taipei Medical University, Taipei (TW); National Health Research Institutes, Zhunan (TW)

( * ) Notice: Subject to any disclaimer, the term of this patent is extended or adjusted under 35 U.S.C. 154(b) by 0 days.

(21) Appl. No.: 15/302,739

(22) PCT Filed: Apr. 9, 2015

(86) PCT No.: PCT/US2015/025084
§ 371 (c)(1),
(2) Date: Oct. 7, 2016

(87) PCT Pub. No.: WO2015/157504
PCT Pub. Date: Oct. 15, 2015

(65) Prior Publication Data
US 2017/0057956 A1 Mar. 2, 2017

Related U.S. Application Data

(60) Provisional application No. 61/978,606, filed on Apr. 11, 2014.

(51) Int. Cl.
*C07D 471/04* (2006.01)
*C07D 487/04* (2006.01)
*C07D 231/56* (2006.01)
*C07D 209/08* (2006.01)
*A61K 31/437* (2006.01)

(52) U.S. Cl.
CPC .......... *C07D 471/04* (2013.01); *A61K 31/437* (2013.01); *C07D 209/08* (2013.01); *C07D 231/56* (2013.01); *C07D 487/04* (2013.01)

(58) Field of Classification Search
None
See application file for complete search history.

(56) References Cited

U.S. PATENT DOCUMENTS

| 4,288,595 A | 9/1981 | Ledig |
| 2011/0245315 A1 | 10/2011 | Chen et al. |

FOREIGN PATENT DOCUMENTS

| WO | WO-2004/078757 A2 | 9/2004 |
| WO | WO-2005/013691 A1 | 2/2005 |
| WO | WO-2006/050076 A1 | 5/2006 |
| WO | WO-2007/011626 A2 | 1/2007 |
| WO | WO-2009/137462 A2 | 11/2009 |
| WO | WO-2011/011186 A2 | 1/2011 |
| WO | WO-2011/094708 A2 | 8/2011 |
| WO | WO-2012/058645 A1 | 5/2012 |
| WO | WO-2012/106343 A2 | 8/2012 |
| WO | WO-2013/062344 A1 | 5/2013 |
| WO | WO-2015/087151 A1 | 6/2015 |

OTHER PUBLICATIONS

SciFinder by CAS, CAPLUS Acc. No. 1988:610923, Jotwani et al., Indian Journal of Chemistry, Section B: Organic Chemistry Including Medicinal Chemistry, 27B(2), p. 166 (abstract).*
Database CAPLUS, Acc. No. 1943:31462, Kruber, Berichte der Deutschen Chemischen Gesellschaft [Abteilung] B: Abhandlungen (1943), vol. 76B, pp. 128-143 (SciFinder abstract).*
Kruber, Berichte der Deutschen Chemischen Gesellschaft [Abteilung] B: Abhandlungen (1943), vol. 76B, pp. 128-143.*
Porter et al., Bioorganic & Medicinal Chemistry Letters (2009), 19(10), pp. 2780-2784.*
Butler et al "Rational Design and Simple Chemistry Yield a Superior, Neuroprotective HDAC6 Inhibitor, Tubastatin A" Journal of the American Chemical Society vol. 132, pp. 10842-10846, 2010.
Smith et al "A Novel and Highly Efficient Synthesis of the Aza Analogs of Tacrine" Tetrahedron Letters vol. 40, pp. 5643-5646, 1999.

* cited by examiner

*Primary Examiner* — Brian J Davis
(74) *Attorney, Agent, or Firm* — Cesari and McKenna, LLP

(57) ABSTRACT

Fused bicycle indol, indoline, azoindole, or azoindoline compounds of Formula (I) set forth herein. Also disclosed are pharmaceutically acceptable salts of these compounds and pharmaceutical compositions containing the same. Further disclosed is a method for treating cancer, e.g., glioma, prostate cancer, and colorectal cancer, with these compounds.

9 Claims, No Drawings

HISTONE DEACETYLASE INHIBITORS

CROSS REFERENCE TO RELATED APPLICATIONS

This application is the National Stage of International Application No. PCT/US2015/025084, filed on Apr. 9, 2015, which claims the benefit of Provisional Application No. 61/978,606, filed on Apr. 11, 2014. The contents of both applications are hereby incorporated by reference in their entirety.

BACKGROUND

Histone deacetylases (HDACs) are a class of enzymes, e.g., HDAC1-11, that regulate gene expression via histone acetylation. HDAC inhibitors have been known to induce expression of p21 and/or p27, two proteins that induce cell growth arrest, differentiation, and apoptosis in tumor cells. See Nimmanapalli et al., Blood 2003, 101, 3236-39; and Roy et al., Molecular Cancer Therapeutics 2007, 6, 2696-2707. They have thus attracted great attention as potent anticancer agents. See, e.g., Lu et al., Journal of Medicinal Chemistry 2005, 48, 5530-35; Kulp et al., Clinical Cancer Research 2006, 12, 5199-5206; and Ryan et al., Journal of Clinical Oncology 2005, 23, 3912-22.

SUMMARY

This invention is based on an unexpected discovery that certain indol, indoline, azoindole, and azoindoline compounds are effective in inhibiting HDACs.

In one aspect, this invention relates to compounds of formula (I) shown below:

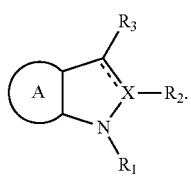
(I)

In this formula, $R_1$ is $SO_2R_a$ or $CH_2R_a$, in which $R_a$ is $C_1$-$C_{10}$ alkyl, $C_2$-$C_{10}$ alkenyl, $C_2$-$C_{10}$ alkynyl, aryl, heteroaryl, $C_3$-$C_{10}$ cycloalkyl, $C_3$-$C_{10}$ cycloalkenyl, $C_1$-$C_{10}$ heterocycloalkyl, or $C_1$-$C_{10}$ heterocycloalkenyl; each of alkyl, alkenyl, and alkynyl optionally substituted with halo, hydroxyl, nitro, cyano, amino, $C_1$-$C_6$ alkoxy,

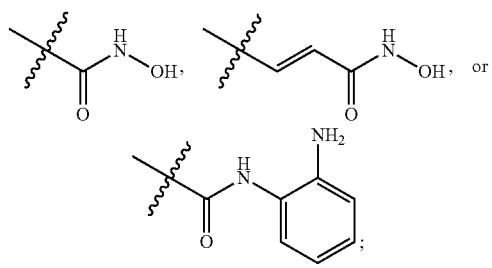

and each of aryl, heteroaryl, cycloalkyl, cycloalkenyl, heterocycloalkyl, or heterocycloalkenyl optionally substituted with halo, hydroxyl, nitro, cyano, amino, $C_1$-$C_6$ alkoxy, $C_1$-$C_6$ alkyl, $C_2$-$C_6$ alkenyl, $C_2$-$C_6$ alkynyl, aryl, heteroaryl, $C_3$-$C_{10}$ cycloalkyl, $C_3$-$C_{10}$ cycloalkenyl, $C_1$-$C_{10}$ heterocycloalkyl, $C_1$-$C_{10}$ heterocycloalkenyl,

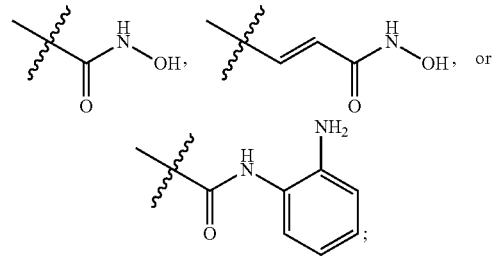

each of $R_2$ and $R_3$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl; X is C, CH, N, or NH; A is heteroaryl; and = is a single or double bond.

One subset of these compounds includes those in which A is a pyridine ring or a pyrimidine ring and X is CH, C, or N. Each of the pyridine ring and the pyridmidine ring is optionally mono, di, or tri-substituted with halo, hydroxyl, nitro, cyano, amino, $C_1$-$C_6$ alkylamino, $C_2$-$C_{10}$ dialkylamino, $C_1$-$C_6$ alkoxy, $C_1$-$C_6$ alkyl, $C_2$-$C_6$ alkenyl, $C_2$-$C_6$ alkynyl, aryl, heteroaryl, $C_3$-$C_{10}$ cycloalkyl, $C_3$-$C_{10}$ cycloalkenyl, $C_1$-$C_{10}$ heterocycloalkyl, or $C_1$-$C_{10}$ heterocycloalkenyl, in which alkenyl is optionally substituted with C(O)OR', C(O)NR'R", R' being H or $C_1$-$C_6$ alkyl and R" being H, OH, $C_1$-$C_6$ alkyl, or aryl.

$R_a$ can be naphthalenyl or phenyl, each of which is optionally mono-, di, or tri-substituted with halo, hydroxyl, nitro, cyano, amino, $C_1$-$C_6$ alkylamino, $C_2$-$C_{10}$ dialkylamino, $C_1$-$C_6$ alkoxy, $C_1$-$C_6$ alkyl, $C_2$-$C_6$ alkenyl, $C_2$-$C_6$ alkynyl, aryl, heteroaryl, $C_3$-$C_{10}$ cycloalkyl, $C_3$-$C_{10}$ cycloalkenyl, $C_1$-$C_{10}$ heterocycloalkyl, or $C_1$-$C_{10}$ heterocycloalkenyl, alkenyl being optionally substituted with C(O)OR''', in which R''' is H or $C_1$-$C_6$ alkyl.

$R_a$ can also be phenyl optionally substituted with

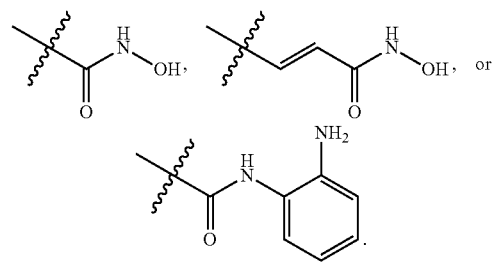

Typically, $R_2$ is H or deleted and $R_3$ is H.

In another aspect, this invention relates to compounds of formula (I), in which $R_1$ is $SO_2R_b$ or $CH_2R_b$, $R_b$ being phenyl optionally substituted with

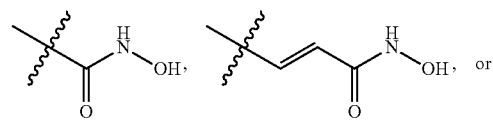

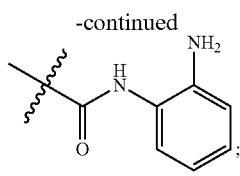

each of $R_2$ and $R_3$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl; X is C, CH, N, or NH; A is phenyl; and $=$ is a single or double bond.

One subset of the just-described compounds includes those in which X is CH, C, or N; $R_2$ is H or deleted; and $R_3$ is H.

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. The term "alkylene" refers to bivalent alkyl. Examples include —$CH_2$—, —$CH_2CH_2$—, —$CH_2CH_2CH_2$—, —$CH_2(CH_3)CH_2$—, and —$CH_2CH_2CH_2CH_2$—. The term "alkoxy" refers to an —O-alkyl group. Examples include methoxy, ethoxy, propoxy, and isopropoxy.

The term "alkenyl" refers to a straight or branched hydrocarbon group, containing 2-20 (e.g., 2-10 and 2-6) carbon atoms and one or more double bonds. Examples include —CH=$CH_2$, —CH=$CHCH_3$, —$CH_2$CH=$CH_2$, and —$CH_2$CH=$CHCH_3$. The term "alkynyl" refers to a straight or branched hydrocarbon group, containing 2-20 (e.g., 2-10 and 2-6) carbon atoms and one or more triple bonds.

The term "cycloalkyl" refers to a saturated monocyclic, bicyclic, tricyclic, or tetracyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The term "cycloalkylenyl" refers to a partially unsaturated monocyclic, bicyclic, tricyclic, or tetracyclic hydrocarbon group having 3 to 12 carbons and one or more double bonds.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples of heterocycloalkyl groups include, but are not limited to, piperazinyl, imidazolidinyl, azepanyl, pyrrolidinyl, dihydrothiadiazolyl, dioxanyl, morpholinyl, tetrahydropuranyl, and tetrahydrofuranyl. The term "heterocycloalkylene" refers to bivalent heterocycloalkyl. The term "heterocycloalkenyl" refers to a nonaromatic 5-8 membered monocyclic, 8-12 membered bicyclic, or 11-14 membered tricyclic ring system having one or more heteroatoms (e.g., O, N, P, and S) and one or more double bond.

The term "aryl" refers to a 6-carbon monocyclic, 10-carbon bicyclic, 14-carbon tricyclic aromatic ring system wherein each ring may have 1 to 5 substituents. Examples of aryl groups include phenyl, naphthenyl, and anthracenyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

The term "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further substituted.

The compounds described above also include their salts and solvates, if applicable. A salt can be formed between an anion and a positively charged group (e.g., amino) on a compound; examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group; examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Also within the scope of this invention is a pharmaceutical composition containing one of the compounds described above as a therapeutic agent and a pharmaceutically acceptable carrier. The pharmaceutical composition can further contain another therapeutic agent for treating cancer. This invention also features the use of one of the compounds described above for the manufacture of a medicament for treating cancer.

Still within the scope of this invention is a method of treating cancer by administering to a subject in need thereof an effective amount of any compound described above. The compound can be conveniently administered once a day to the subject in need thereof. The term "treating" refers to application or administration of the compound to a subject, having cancer, with the purpose to cure, heal, alleviate, relieve, alter, remedy, ameliorate, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

Cancers that can be treated by the methods of this invention include both solid and haematological tumours of various organs. Examples of solid tumors are pancreatic cancer; bladder cancer; colorectal cancer; breast cancer, including metastatic breast cancer; prostate cancer, including androgen-dependent and androgen-independent prostate cancer; renal cancer, including metastatic renal cell carcinoma; hepatocellular cancer; lung cancer, including non-small cell lung cancer (NSCLC), bronchioloalveolar carcinoma (BAC), and adenocarcinoma of the lung; ovarian cancer, including progressive epithelial or primary peritoneal cancer; cervical cancer; gastric cancer; esophageal cancer; head and neck cancer, including squamous cell carcinoma of the head and neck; melanoma; neuroendocrine cancer, including metastatic neuroendocrine tumors; brain tumors, including glioma, anaplastic oligodendroglioma, adult glioblastoma multiforme, and adult anaplastic astrocytoma; bone cancer; and soft tissue sarcoma. Examples of hematologic malignancy are acute myeloid leukemia; chronic myelogenous leukemia (CML), including accelerated CML and CML blast phase; acute lymphoblastic leukemia; chronic lymphocytic leukemia; Hodgkin's disease; non-Hodgkin's lymphoma, including follicular lymphoma and mantle cell lymphoma; B-cell lymphoma; T-cell lymphoma; multiple myeloma; Waldenstrom's macroglobulinemia; myelodysplastic syndromes, including refractory anemia, refractory anemia with ringed sideroblasts, refractory anemia with excess blasts (RAEB), and RAEB in transformation; and myeloproliferative syndromes.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A composition for oral administration can be in various orally acceptable dosage forms including capsule, tablet, emulsion and aqueous suspension, dispersion, and solution. In the case of tablet, commonly used carriers include lactose and corn starch. Lubricating agents, such as magnesium stearate, are also typically added. For oral administration in a capsule form, useful diluents include lactose and dried corn starch. When aqueous emulsions or suspensions are administered orally, the active ingredient can be suspended or dissolved in an oily phase combined with emulsifying or suspending agents. If desired, certain sweetening, flavoring, or coloring agents can be added. Oral solid dosage forms can be prepared by amorphous spray dried techniques, hot melt extrusion strategy, micronization, and nano-milling technologies.

An inhalation composition or nasal aerosol can be prepared according to techniques well known in the art of pharmaceutical formulation. It is typically prepared as a solution in saline, employing benzyl alcohol or other suitable preservatives, absorption promoters, fluorocarbons, and/or other solubilizing or dispersing agents.

A composition having an active compound can also be administered in the form of suppositories for rectal administration.

The carrier in the pharmaceutical composition must be "acceptable" in the sense that it is compatible with the active ingredient of the composition (preferably, capable of stabilizing the active ingredient) and not deleterious to the subject to be treated. One or more solubilizing agents can be utilized as a pharmaceutical excipient(s) for delivery of an active compound. Examples of other carriers include colloidal silicon oxide, magnesium stearate, cellulose, sodium lauryl sulfate, and D&C Yellow #10.

The compounds of this invention can be used together with one or more other active agents to treat cancer. Thus, this invention also relates to a method for treating cancer by administering to a subject in need of the treatment an effective amount of a compound of this invention and an effective amount of one or more other active agents. Active agents include, but are not limited to, immunomodulatory agents, such as interferons α, β, and γ; antiviral agents, such as ribavirin and amantadine; inhibitors of indoleamine 2,3-dioxygenase and/or tryptophan 2,3-dioxygenase; and inhibitors of other targets in the HDAC-associated conditions. Such an active agent and a compound of this invention may be applied to a subject at two separate times or simultaneously but in two dosage forms. Alternatively, they can be combined in a composition as described above for use as a single dosage form.

The details of one or more embodiments of the invention are set forth in the description below. Other features, objects, and advantages of the invention will be apparent from the description and from the claims.

DETAILED DESCRIPTION

Shown in Table 1 below are exemplary compounds of this invention:

TABLE 1

Exemplary compounds

TABLE 1-continued
Exemplary compounds
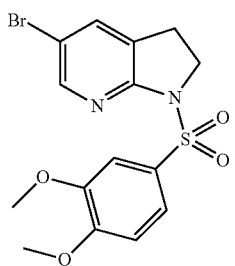 2d
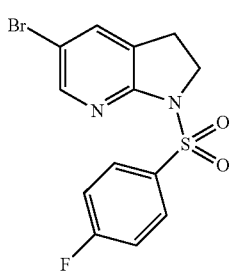 2e
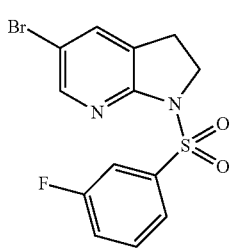 2f
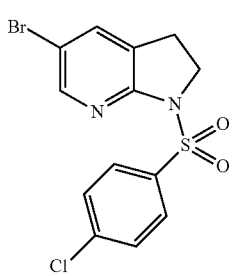 2g
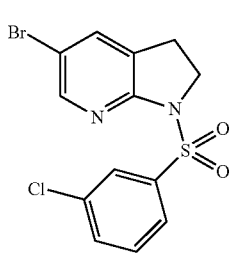 2h
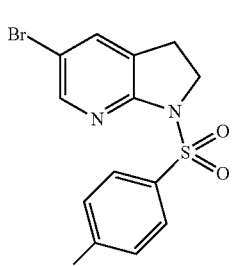 2i
TABLE 1-continued
Exemplary compounds
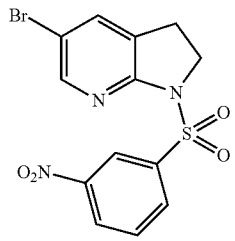 2j
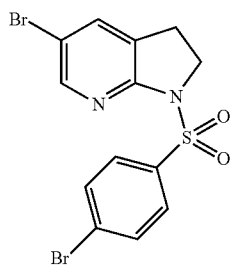 2k
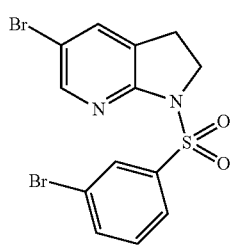 2l
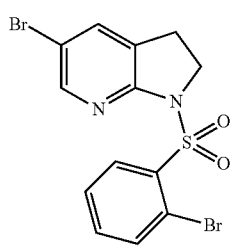 [SMILES: O=S(=O)(c1ccccc1Br)N1CCc2cc(Br)cnc21] 2m
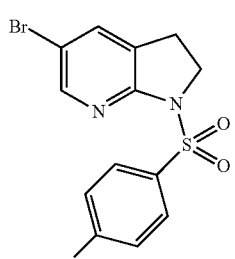 2n
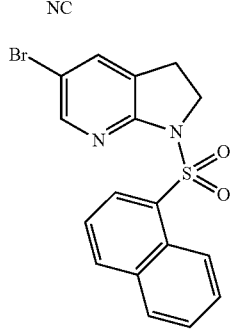 2o TABLE 1-continued Exemplary compounds TABLE 1-continued
Exemplary compounds
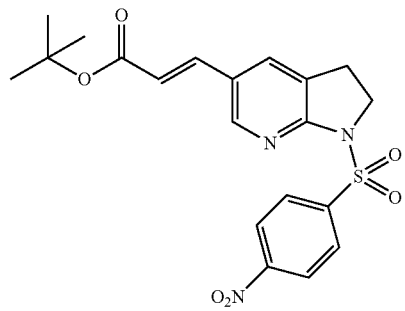 [SMILES: CC(C)(C)OC(=O)/C=C/c1cnc2c(c1)CCN2S(=O)(=O)c1ccc([N+](=O)[O-])cc1]
3i
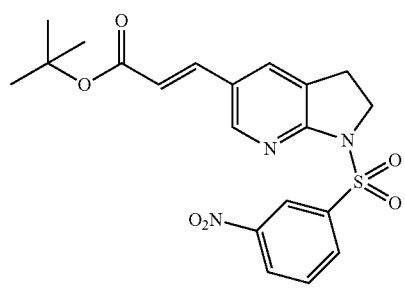 [SMILES: CC(C)(C)OC(=O)/C=C/c1cnc2c(c1)CCN2S(=O)(=O)c1cccc([N+](=O)[O-])c1]
3j
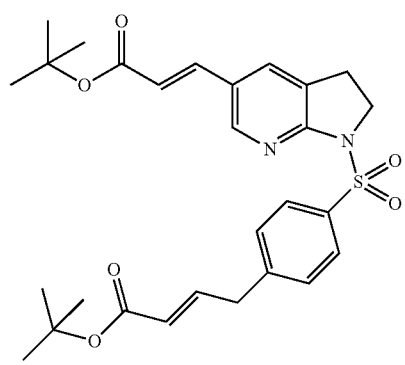 [SMILES: CC(C)(C)OC(=O)/C=C/Cc1ccc(S(=O)(=O)N2CCc3cc(/C=C/C(=O)OC(C)(C)C)cnc32)cc1]
3k
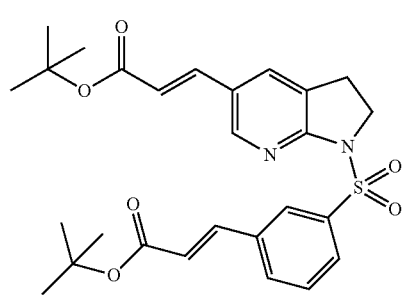 [SMILES: CC(C)(C)OC(=O)/C=C/c1cccc(S(=O)(=O)N2CCc3cc(/C=C/C(=O)OC(C)(C)C)cnc32)c1]
3l
TABLE 1-continued
Exemplary compounds
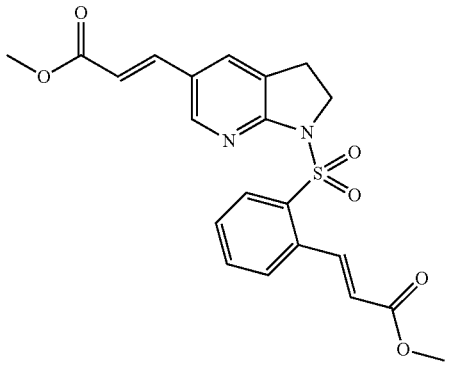
3m
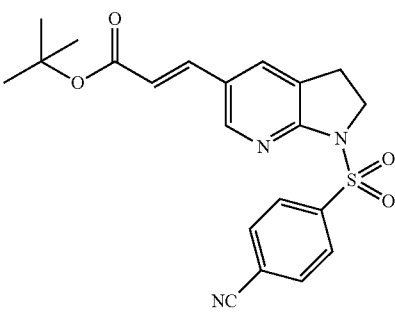 [SMILES: CC(C)(C)OC(=O)/C=C/c1cnc2c(c1)CCN2S(=O)(=O)c1ccc(C#N)cc1]
3n
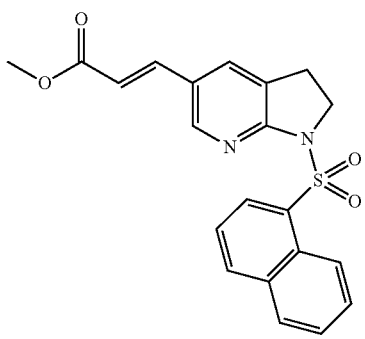 [SMILES: COC(=O)/C=C/c1cnc2c(c1)CCN2S(=O)(=O)c1cccc2ccccc12]
3o
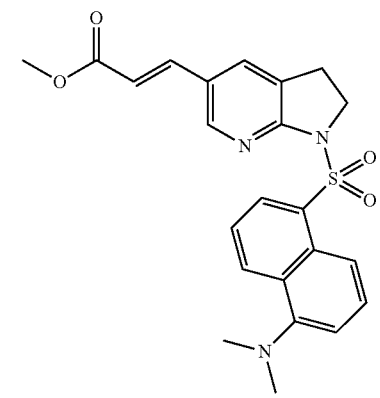 [SMILES: COC(=O)/C=C/c1cnc2c(c1)CCN2S(=O)(=O)c1cccc2c(N(C)C)cccc12]
3p
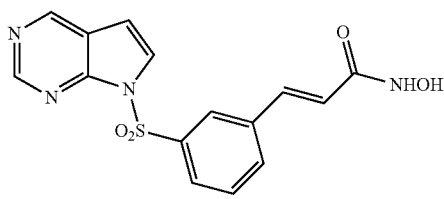
4

TABLE 1-continued
Exemplary compounds
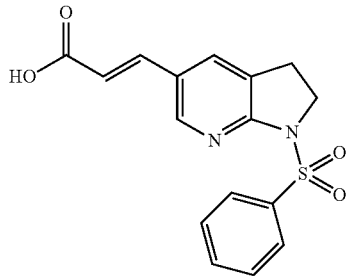 [SMILES: O=C(O)/C=C/c1cnc2c(c1)CCN2S(=O)(=O)c1ccccc1] 4a
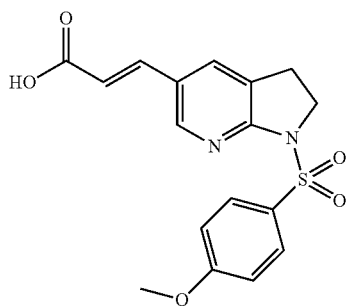 [SMILES: COc1ccc(S(=O)(=O)N2CCc3cc(/C=C/C(=O)O)cnc32)cc1] 4b
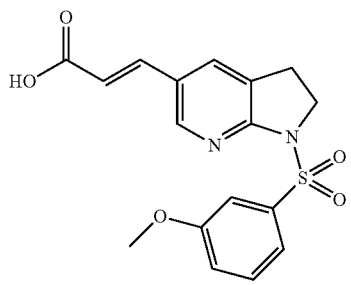 [SMILES: COc1cccc(S(=O)(=O)N2CCc3cc(/C=C/C(=O)O)cnc32)c1] 4c
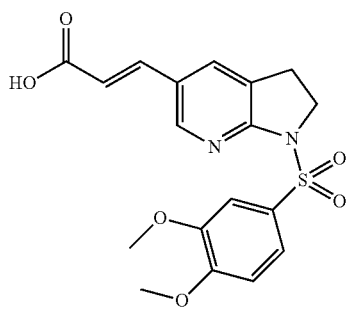 [SMILES: COc1ccc(S(=O)(=O)N2CCc3cc(/C=C/C(=O)O)cnc32)cc1OC] 4d
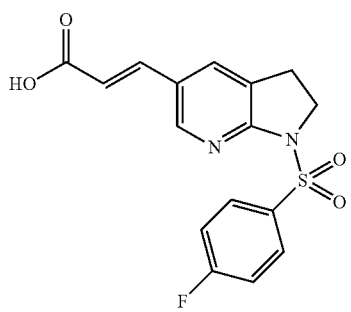 4e
TABLE 1-continued
Exemplary compounds
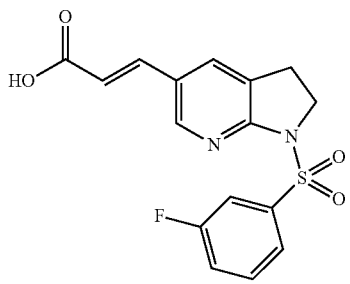 [SMILES: O=C(O)/C=C/c1cnc2c(c1)CCN2S(=O)(=O)c1cccc(F)c1] 4f
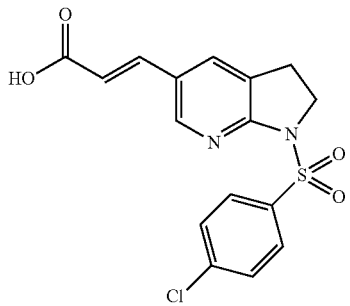 [SMILES: O=C(O)/C=C/c1cnc2c(c1)CCN2S(=O)(=O)c1ccc(Cl)cc1] 4g
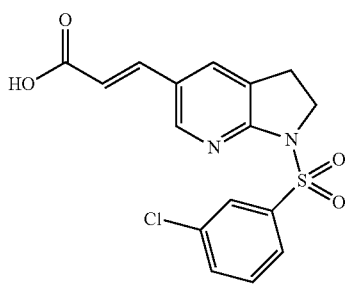 [SMILES: O=C(O)/C=C/c1cnc2c(c1)CCN2S(=O)(=O)c1cccc(Cl)c1] 4h
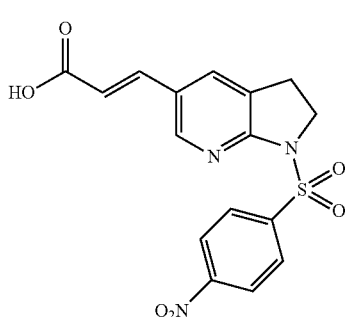 4i
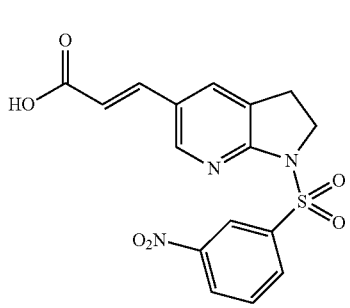 [SMILES: O=C(O)/C=C/c1cnc2c(c1)CCN2S(=O)(=O)c1cccc([N+](=O)[O-])c1] 4j TABLE 1-continued
Exemplary compounds
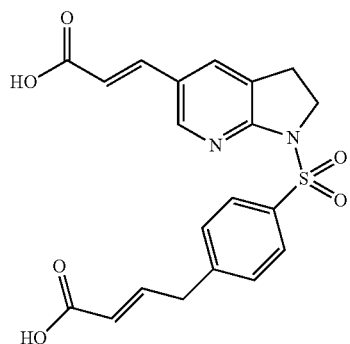 [SMILES: O=C(O)/C=C/Cc1ccc(S(=O)(=O)N2CCc3cc(/C=C/C(=O)O)cnc32)cc1]
4k
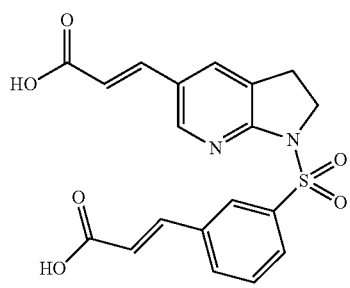 [SMILES: O=C(O)/C=C/c1cccc(S(=O)(=O)N2CCc3cc(/C=C/C(=O)O)cnc32)c1]
4l
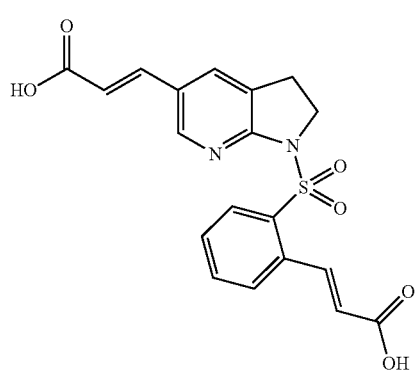 [SMILES: O=C(O)/C=C/c1cnc2c(c1)CCN2S(=O)(=O)c1ccccc1/C=C/C(=O)O]
4m
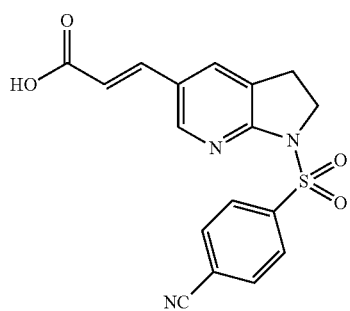 [SMILES: N#Cc1ccc(S(=O)(=O)N2CCc3cc(/C=C/C(=O)O)cnc32)cc1]
4n
TABLE 1-continued
Exemplary compounds
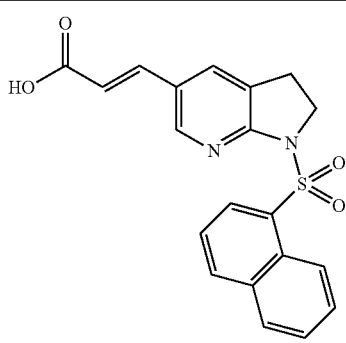
4o
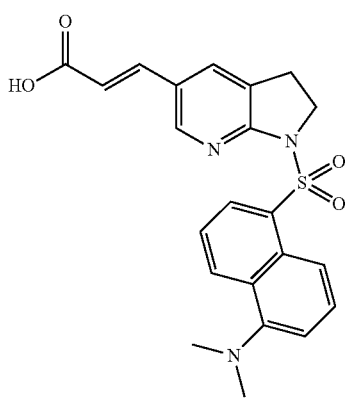 [SMILES: CN(C)c1cccc2c(S(=O)(=O)N3CCc4cc(/C=C/C(=O)O)cnc43)cccc12]
4p
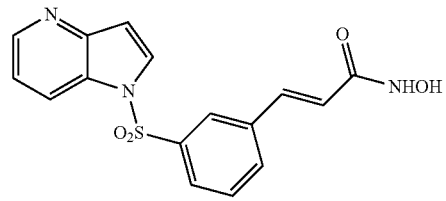
5
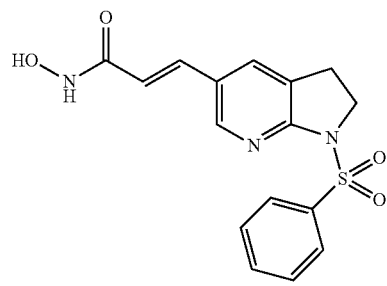 [SMILES: O=C(/C=C/c1cnc2c(c1)CCN2S(=O)(=O)c1ccccc1)NO]
5a
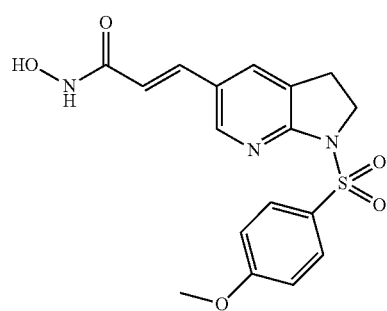 [SMILES: COc1ccc(S(=O)(=O)N2CCc3cc(/C=C/C(=O)NO)cnc32)cc1]
5b TABLE 1-continued Exemplary compounds 5c, 5d, 5e, 5f, 5g, 5h, 5i, 5j, 5k, 5l

TABLE 1-continued
Exemplary compounds
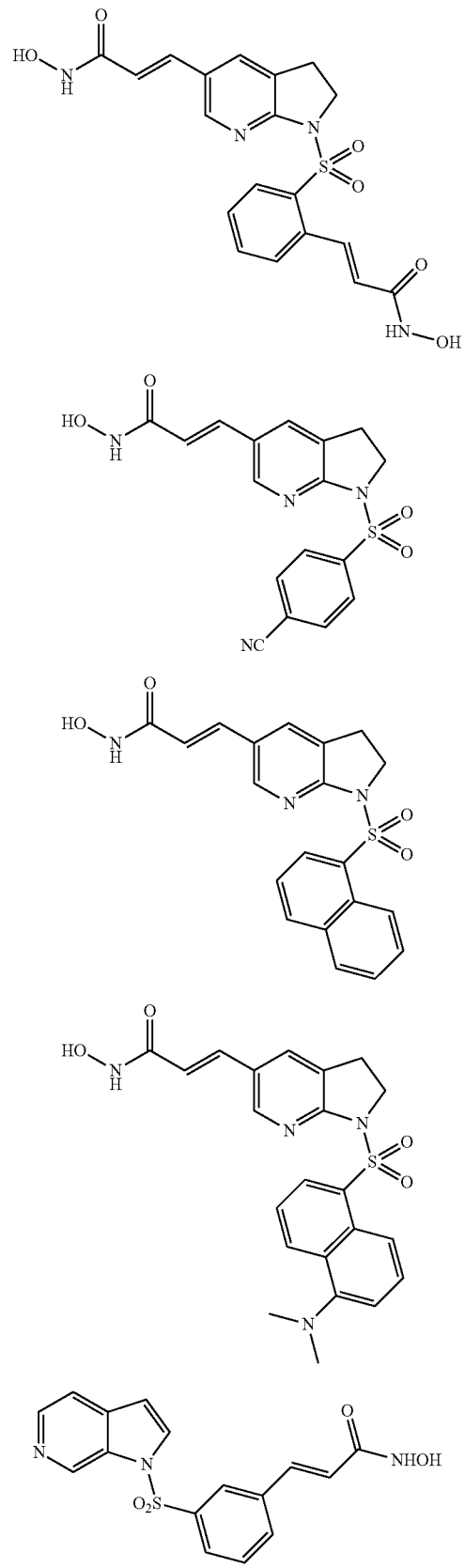
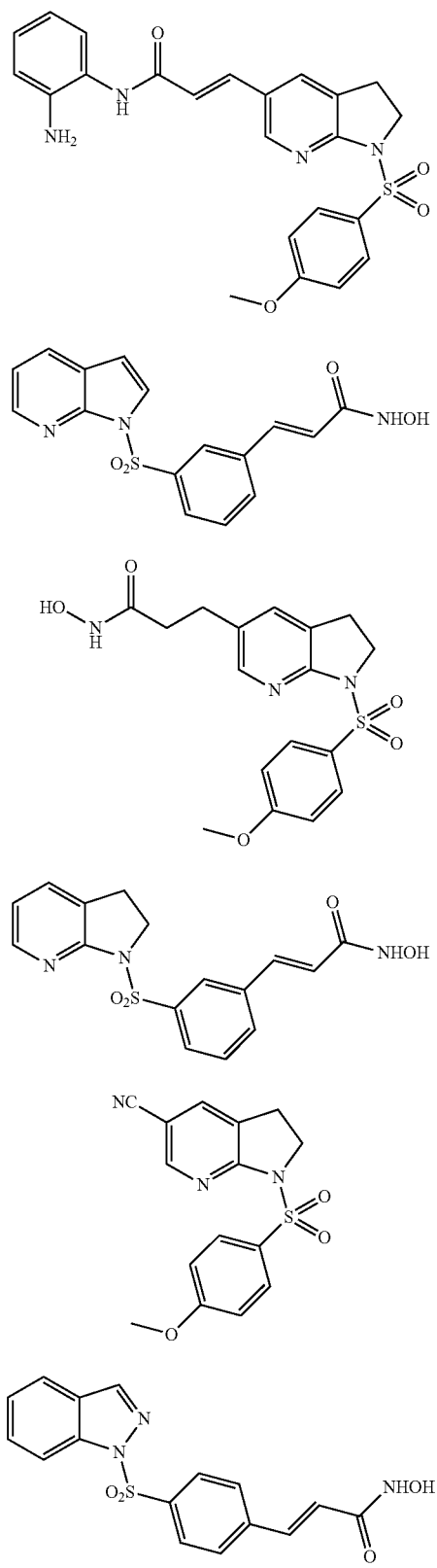

TABLE 1-continued
Exemplary compounds
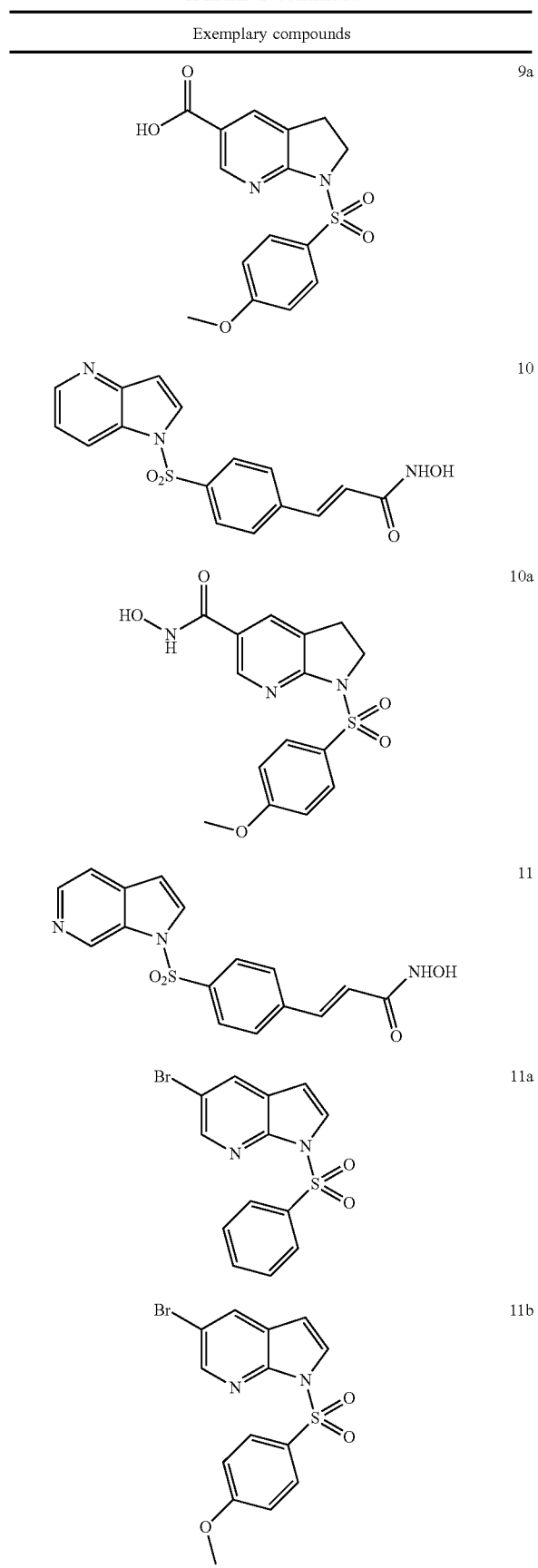
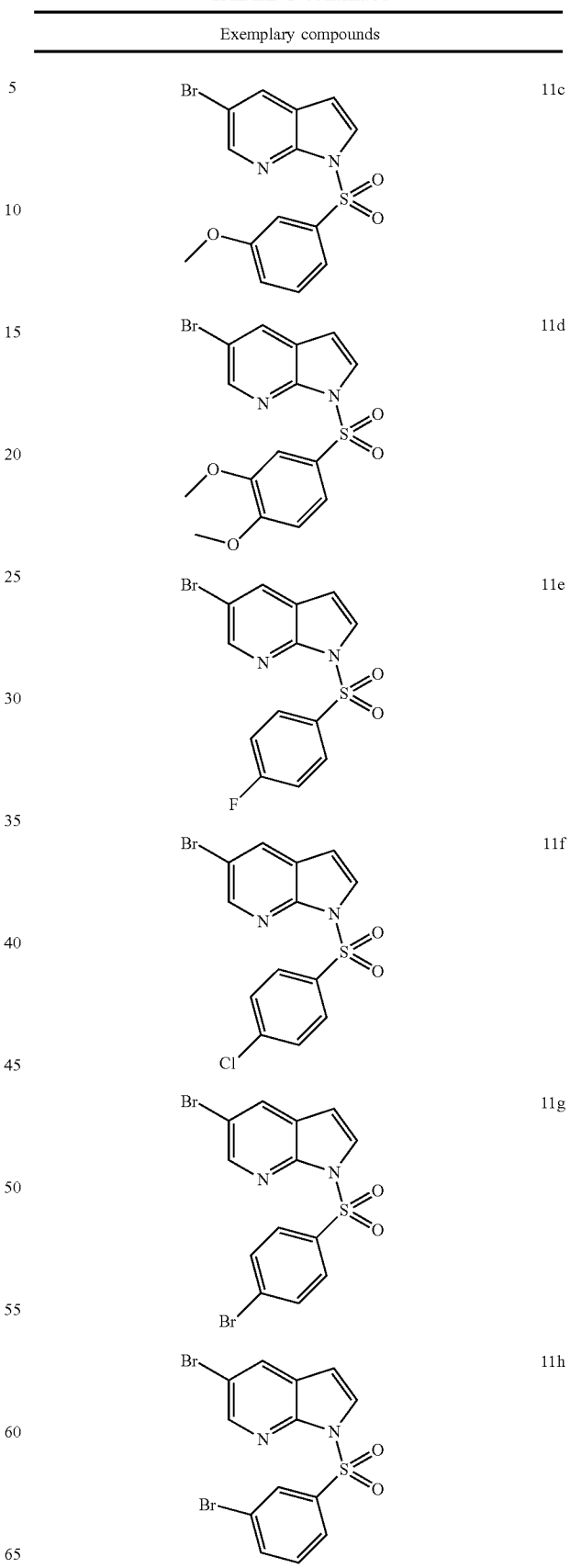

TABLE 1-continued

Exemplary compounds

| | |
|---|---|
| 11i | 5-bromo-7-azaindole N-sulfonyl(2-bromophenyl) |
| 12 | 7-azaindole N-sulfonyl-4-(hydroxyamino-carbonyl vinyl)phenyl |
| 12a | tert-butyl (E)-3-(1-(phenylsulfonyl)-7-azaindol-5-yl)acrylate |
| 12b | tert-butyl (E)-3-(1-((4-methoxyphenyl)sulfonyl)-7-azaindol-5-yl)acrylate |
| 12c | tert-butyl (E)-3-(1-((3-methoxyphenyl)sulfonyl)-7-azaindol-5-yl)acrylate |
| 12d | tert-butyl (E)-3-(1-((3,4-dimethoxyphenyl)sulfonyl)-7-azaindol-5-yl)acrylate |
| 12e | tert-butyl (E)-3-(1-((4-fluorophenyl)sulfonyl)-7-azaindol-5-yl)acrylate |
| 12f | tert-butyl (E)-3-(1-((4-chlorophenyl)sulfonyl)-7-azaindol-5-yl)acrylate |
| 12g | tert-butyl (E)-3-(4-((5-(3-tert-butoxy-3-oxoprop-1-enyl)-7-azaindol-1-yl)sulfonyl)phenyl)acrylate |

TABLE 1-continued
Exemplary compounds
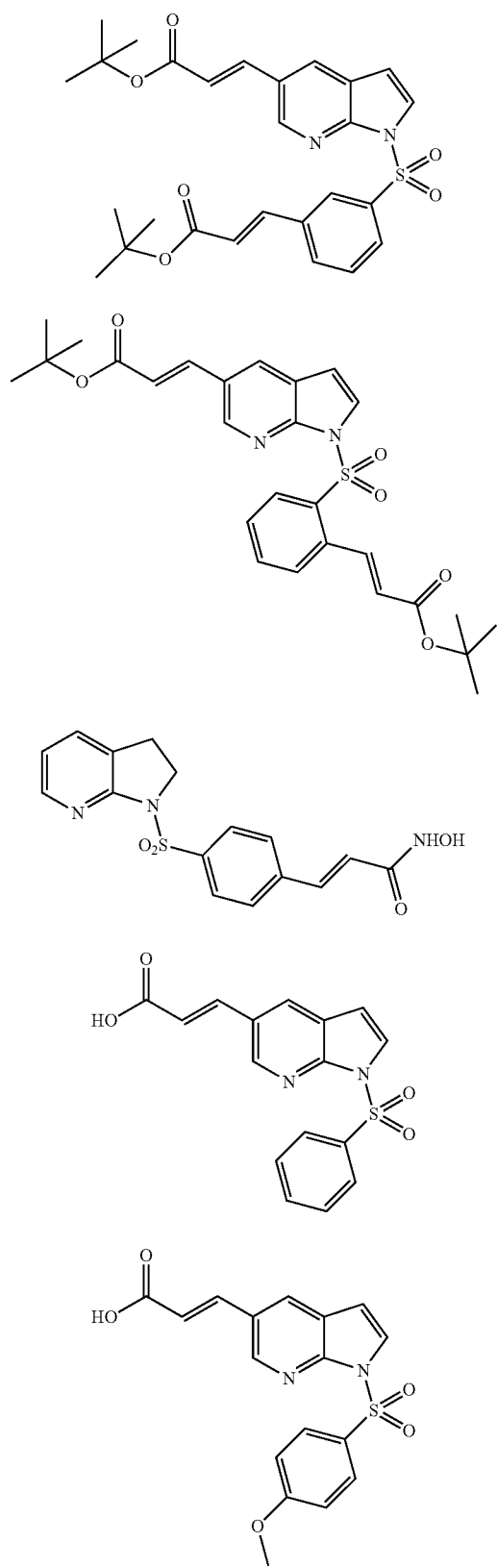
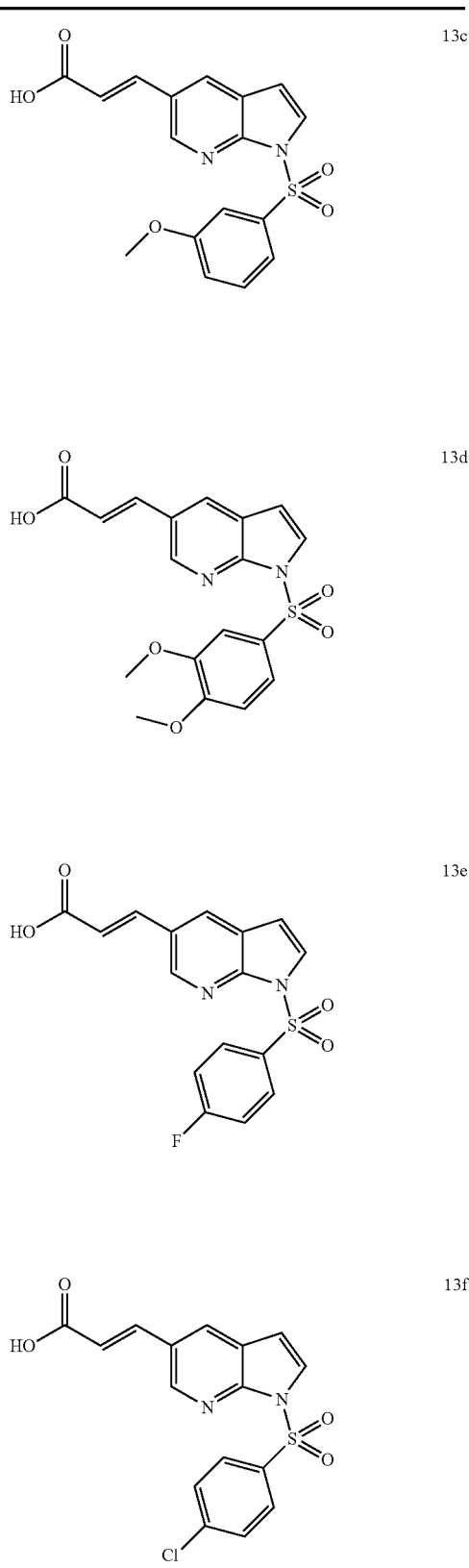

TABLE 1-continued
Exemplary compounds
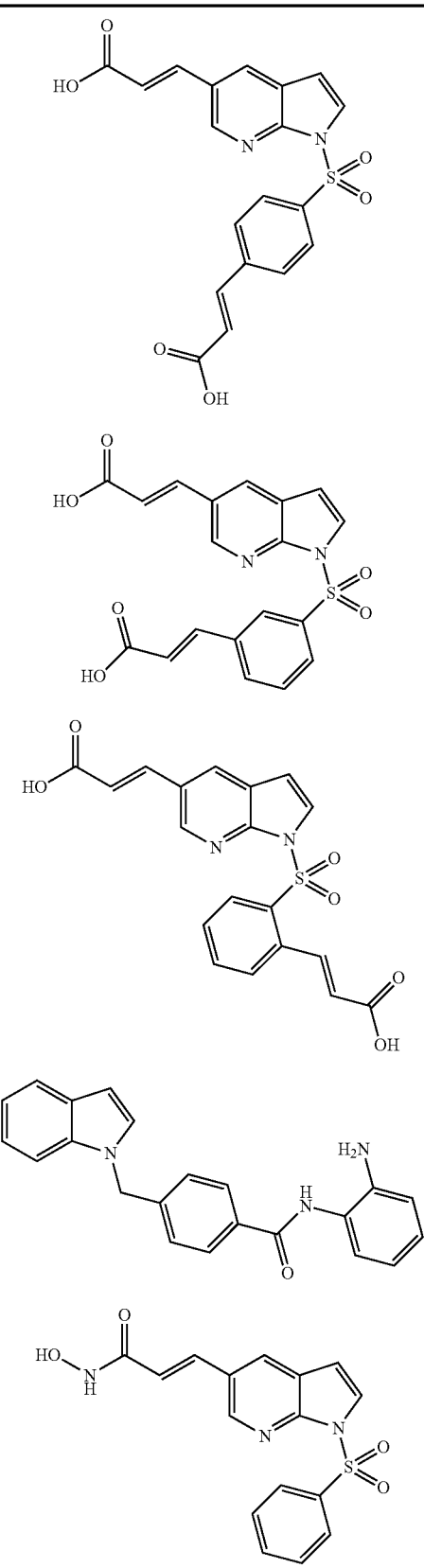
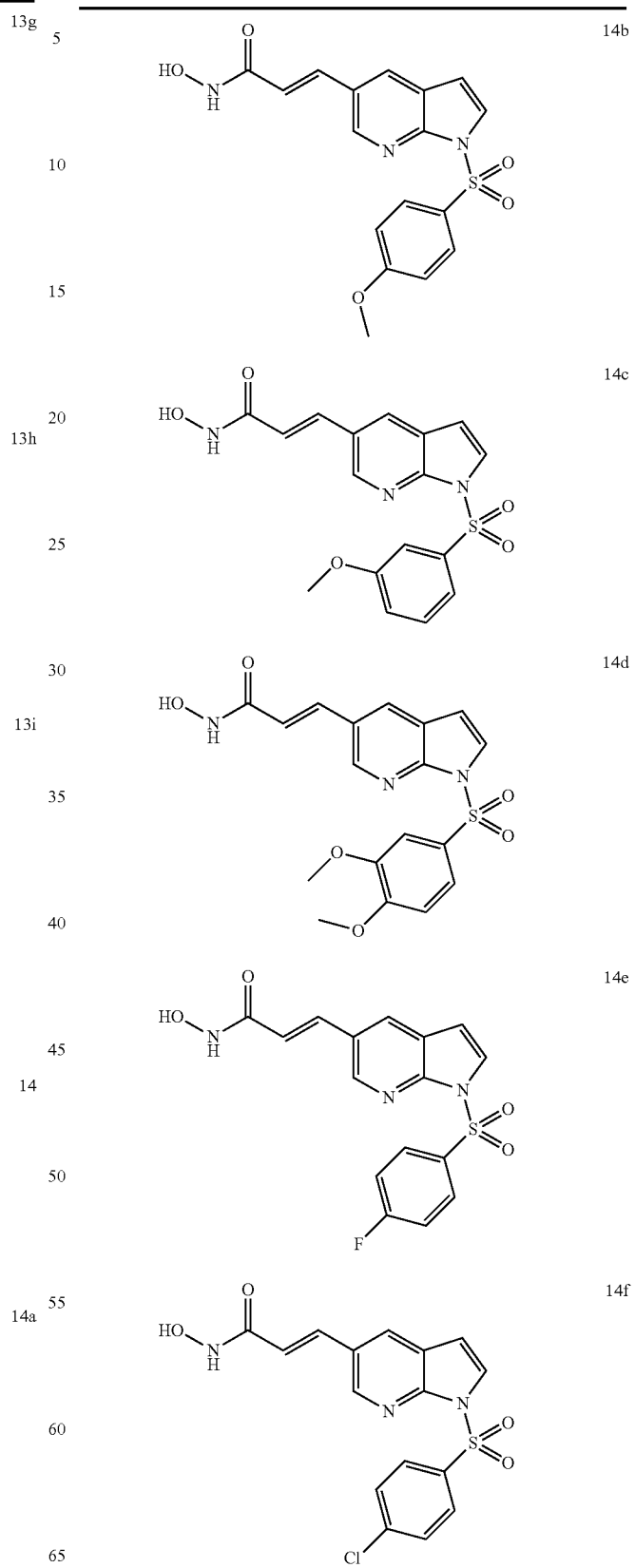

TABLE 1-continued
Exemplary compounds
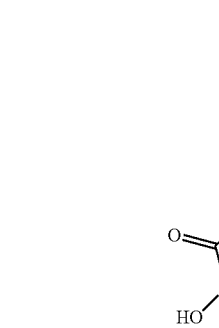

TABLE 1-continued

Exemplary compounds

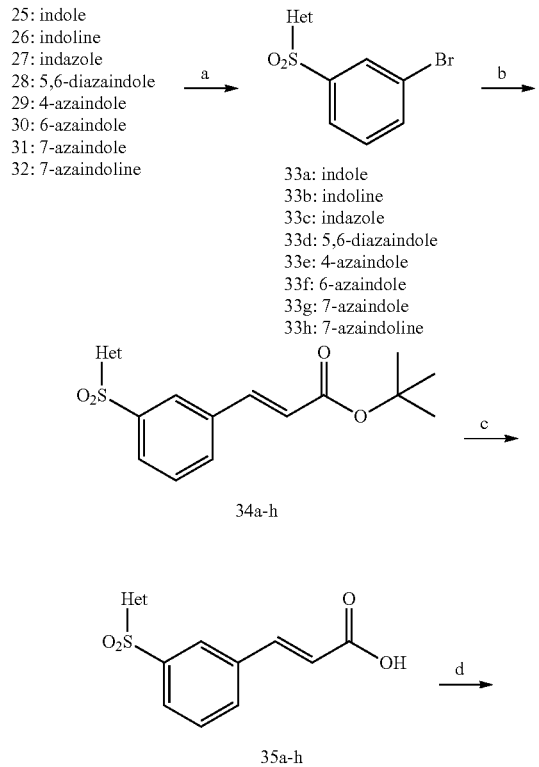

24

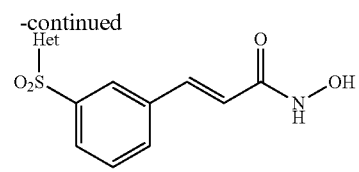

1: indole
2: indoline
3: indazole
4: 5,6-diazaindole
5: 4-azaindole
6: 6-azaindole
7: 7-azaindole
8: 7-azaindoline The compounds of this invention can be prepared by synthetic methods well known in the art. See R. Larock, Comprehensive Organic Transformations (2nd Ed., VCH Publishers 1999); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2nd ed., John Wiley and Sons 2009) and subsequent editions thereof. Specific routes that can be used to synthesize the compounds of this invention can be found in Vinodkumar et al., *J. Polym. Sci. A.* 2008, 14, 37-49; and Varasi et al., *J. Med. Chem.* 2011, 54, 3051-64.

Scheme 1 below depicts routes that can be followed to synthesize Compounds 1-8 of this invention. Note that Het in Scheme 1 and schemes below refers to the heterocyclic ring in each of Compounds 25-32.

In the scheme above, reagents and conditions are as follows: (a) 3-bromobenzenesulfonyl chloride, KOH, tetra-butyl ammonium hydrogen sulfate (TBAHS), $CH_2Cl_2$, room tempearture (RT), yield 56%-93%; (b) $NaHCO_3$, $PPh_3$, $Pd(OAc)_2$, tert-butyl acrylate, triethyl amine (TEA), dimethylformamide (DMF), 80° C., yield 37%-89%; (c) trifluoroacetic acid (TFA), RT, yield 97%-54%; and (d) i. (benzotriazol-1-yloxy)tripyrrolidinophosphonium hexafluorophosphate (PyBOP), $Et_3N$, o-(tetrahydro-2H-pyran-2-yl)hydroxylamine ($NH_2OTHP$), DMF, RT; ii. 5% TFA, MeOH, RT, yield 10%-33%.

The synthesis of Compounds 1-8 and their analytical data are shown below.

(E)-3-(3-(1H-indol-1-ylsulfonyl)phenyl)-N-hydroxyacrylamide (1)

The title compound was obtained in 5% overall yield from compound 35a in a manner similar to that described for the preparation of 3, both shown below. Melting point (mp)=188-191° C. $^1$H NMR (500 MHz, CD3OD and DMSO): δ 6.66 (d, J=15.0 Hz, 1H), 6.85 (s, 1H), 7.29 (t, J=7.0 Hz, 1H), 7.39 (t, J=8.0 Hz, 2H), 7.57-7.63 (m, 2H), 7.78-7.81 (m, 2H), 7.91 (t, J=7.5 Hz, 1H), 8.04 (d, J=8.0 Hz, 1H), 8.10 (s, 1H). MS (EI) m/z: 341.0 (M+, 1.2%), 344.0 (100%). HRMS (EI) for $C_{17}H_{14}O_4N_2S$ (M+): calcd, 342.3691. found 342.0676.

(E)-N-hydroxy-3-(3-(indolin-1-ylsulfonyl)phenyl)acrylamide (2)

The title compound was obtained in 1.04% overall yield from compound 35b in a manner similar to that described for the preparation of 3 shown below. mp=207-209° C. $^1$H NMR (500 MHz, $CD_3OD$): δ 2.65 (t, J=8.0), 3.70 (td, J=5.0, 8.5, 2H), 6.35 (d, J=16.5, 1H), 6.75 (d, J=5.5 Hz, 1H), 6.85 (d, J=7.0 Hz, 1H), 6.97 (d, J=7.0 Hz, 1H), 7.29 (t, J=8.0 Hz, 1H), 7.36 (t, J=8.0 Hz, 1H), 7.40 (d, J=16.0 Hz, 1H), 7.50 (t, J=8.0 Hz, 1H), 7.57 (t, J=8.0 Hz, 1H), 7.69 (d, J=11.0 Hz, 1H). MS (EI) m/z: 343.0 (M+, 0.16%), 116 (100%). HRMS (EI) for $C_{17}H_{16}O_4N_2S$ (M+): calcd, 344.3849. found, 344.0834.

(E)-3-(3-(1H-Indazol-1-ylsulfonyl)phenyl)-N-hydroxyacrylamide (3)

A mixture of indazole (500 mg, 4.23 mmol), potassium hydroxide (470 mg, 8.46 mmol), and tetrabutylammonium hydrogensulfate (220 mg, 0.63 mmol) in dry $CH_2Cl_2$ (30 mL) was stirred for 30 minutes with nitrogen gas. The mixture was filtered and the filtrate was extracted with water (30 mL) and $CH_2Cl_2$ (30 mL×3). The organic layer was collected and dried over anhydrous MgSO$_4$. After the removal of MgSO$_4$ through filtration, the filtrate was concentrated in vacuo to yield an oily product. The residue was purified by a flash column over silica gel (3:1 EtOAc/n-hexane; R$_f$=0.28) to give 1270 mg (89%) of 33c as a white solid: $^1$H NMR (500 MHz, CDCl$_3$) δ 7.32 (t, J=8.0 Hz, 1H), 7.36 (t, J=8.0 Hz, 1H), 7.59 (td, J=1.5, 8.5 Hz, 1H), 7.68 (d, J=8.0 Hz, 1H), 7.71 (d, J=8.0 Hz, 1H), 7.91 (d, J=8.0 Hz, 1H), 8.13 (t, J=2.0 Hz, 1H), 8.19 (d, J=8.5 Hz, 1H), 8.22 (s, 1H).

A mixture of compound 33c (1250 mg, 3.71 mmol), tert-butyl acrylate (0.60 mL, 4.45 mmol), triethylamine (TEA; 0.75 mL, 6.32 mmol), triphenylphosphine (TPP; 480 mg, 1.86 mmol), palladium acetate (410 mg, 1.86 mmol), and sodium bicarbonate (310 mg, 3.70 mmol) was heated to 80° C. in DMF (2 mL) for 5 hours. Then this reaction was quenched with water and extracted with CH$_2$Cl$_2$ (3×30 mL). The organic layer was collected and dried over anhydrous MgSO$_4$. After removal of MgSO$_4$ through filtration, the filtrate was concentrated in vacuo. The residue was purified by a flash column over silica gel (3:1 EtOAc/n-hexane; R$_f$=0.28) to give 1180 mg (81%) of 34c as a solid: $^1$H NMR (500 MHz, CDCl$_3$) δ 1.51 (s, 9H), 6.38 (dd, J=6.0, 16.5 Hz, 1H), 7.35 (t, J=7.5 Hz, 1H), 7.48 (d, J=16.0 Hz, 1H), 7.55 (d, J=8.0 Hz, 2H), 7.58 (td, J=1.0, 7.0 Hz, 1H), 7.70 (d, J=8.0 Hz, 1H), 7.98 (d, J=2.0 Hz, 2H), 8.20 (s, 1H), 8.22 (d, J=8.5 Hz, 1H).

To a solid of compound 34c (1030 mg, 2.60 mmol) and trifluoroacetic acid (8.60 mL, 0.13 mmol) and stirred 30 minutes followed by addition of water (20 mL) to afford a white solid. The resulting solid was collected by filtration and purified by recrystallization with ethanol to give 450 mg (53%) of 35c as a pink solid: $^1$H NMR (500 MHz, CD$_3$OD and CDCl$_3$) δ 6.07 (d, J=16.0 Hz, 1H), 6.97 (t, J=7.5 Hz, 1H), 7.11 (t, J=8.0 Hz, 1H), 7.19 (d, J=7.0 Hz, 1H), 7.22 (d, J=7.5 Hz, 1H), 7.36 (dd, J=8.0, 13.5 Hz, 2H), 7.52 (d, J=8.0 Hz, 1H), 7.69 (s, 1H), 7.78 (d, J=8.5 Hz, 1H), 7.89 (s, 1H).

To a mixture of compound 35c (420 mg, 1.28 mmol), PyBOP (770 mg, 1.52 mmol), DMF (1 mL), NH$_2$OTHP (150 mg, 1.29 mmol), and TEA (1 mL, 3.52 mmol) was stirred 5 hours under nitrogen. The mixture was filtered and the filtrate was extracted with water (30 mL) and CH$_2$Cl$_2$ (3×30 mL). The organic layer was collected and dried over anhydrous MgSO$_4$. After removal of MgSO$_4$ through filtration, the filtrate was concentrated in vacuo to yield an oily product. The residue was purified by a flash column over silica gel (1:2 EtOAc/n-hexane; R$_f$=0.39) to take white solid. Then solid was added 5% trifluoroacetic acid (60 mL) and methanol (3 mL), then stirred for 30 minutes. This reaction was concentrated in vacuo and filtered to yield a white product. The mixture was washed by water/CH$_2$Cl$_2$ to give 80 mg (18%) of 3 as a purple solid: mp=166-168° C.; $^1$H NMR (500 MHz, CD$_3$OD and DMSO) δ 6.52 (d, J=16.0 Hz, 1H), 7.39 (t, J=7.5 Hz, 1H), 7.51-7.54 (m, 2H), 7.64 (t, J=8.0 Hz, 1H), 7.79 (d, J=8.0 Hz, 2H), 7.90 (d, J=8.0 Hz, 1H), 8.11 (s, 1H), 8.21 (d, J=8.5 Hz, 1H), 8.35 (s, 1H); HRMS (ESI) for C$_{16}$H$_{13}$O$_4$N$_3$S (M-H) calcd 343.0627. found 342.0541.

(E)-3-(3-((7H-Pyrrolo[2,3-d]pyrimidin-7-yl)sulfonyl)phenyl)-N-hydroxyacrylamide (4)

The title compound was obtained in 59.88% overall yield from compound 35d in a manner similar to that described above for the preparation of 3: $^1$H-NMR (500 MHz, DMSO-d$_6$): δ 6.62 (d, J=15.5 Hz, 1H), 6.96 (d, J=4.0 Hz, 1H), 7.51 (d, J=15.5 Hz, 1H), 7.67 (t, J=8.0 Hz, 1H), 7.92 (d, J=7.5 Hz, 1H), 8.00 (d, J=4.0 Hz, 1H), 8.10 (d, J=8.0 Hz, 1H), 8.37 (s, 1H), 9.00 (s, 1H), 9.12 (s, 1H).

(E)-3-(3-(1H-Pyrrolo[3,2-b]pyridin-1-ylsulfonyl)phenyl)-N-hydroxyacrylamide (5)

The title compound was obtained in 17% overall yield from compound 35e in a manner similar to that described for the preparation of 3: mp=148-150° C. $^1$H NMR (500 MHz, CD$_3$OD): δ 6.58 (d, J=16.0 Hz, 1H), 7.04 (d, J=4.0 Hz, 1H), 7.59 (d, J=15.5 Hz, 1H), 7.63 (t, J=8.0 Hz, 1H), 7.69 (dd, J=5.5, 8.5 Hz, 1H), 7.91 (d, J=7.5 Hz, 1H), 8.06 (d, J=7.5 Hz, 1H), 8.24 (s, 1H), 8.37 (d, J=4 Hz, 1H), 8.64 (d, J=5.0 Hz, 1H), 8.86 (d, J=8.5 Hz, 1H).

(E)-3-(3-(1H-Pyrrolo[2,3-c]pyridin-1-ylsulfonyl)phenyl)-N-hydroxyacrylamide (6)

The title compound was obtained in 33% overall yield from compound 35f in a manner similar to that described for the preparation of 3: mp=128-129° C.; $^1$H NMR (500 MHz, CD$_3$OD) δ 6.58 (d, J=17.0 Hz, 1H), 7.19 (d, J=3.5 Hz, 1H), 7.59 (d, J=15.5 Hz, 1H), 7.65 (t, J=8.0 Hz, 1H), 7.95 (d, J=7.5 Hz, 1H), 8.13 (d, J=8.0 Hz, 1H), 8.18 (d, J=6.0 Hz, 1H), 8.30 (s, 1H), 8.49 (d, J=6.5 Hz, 1H), 8.54 (d, J=3.5 Hz, 1H), 9.56 (s, 1H); MS (EI) m/z: 342.0 (M$^+$, 3.57%), 118 (100%); HRMS (EI) for C$_{16}$H$_{13}$O$_4$N$_3$S (M$^+$) calcd 343.0627. found 343.0629.

(E)-3-(3-(1H-Pyrrolo[2,3-b]pyridin-1-ylsulfonyl)phenyl)-N-hydroxyacrylamide (7)

The title compound was obtained in 20% overall yield from compound 35g in a manner similar to that described for the preparation of 3: mp=188-191° C.; $^1$H NMR (500 MHz, CD$_3$OD) δ 6.55 (d, J=15.5 Hz, 1H), 6.74 (d, J=4.0 Hz, 1H), 7.25 (dd, J=5.0, 7.5 Hz, 1H), 7.54 (m, 1H), 7.57 (d, J=4.0 Hz, 1H), 7.78 (d, J=8.0 Hz, 1H), 7.82 (d, J=4.0 Hz, 1H), 7.97 (dd, J=1.5, 7.5 Hz, 1H), 8.06 (d, J=7.5 Hz, 1H), 8.33 (dd, J=1.5, 4.5 Hz, 1H), 8.36 (s, 1H); MS (EI) m/z: 342.0 (M$^+$, 2.20%), 118 (100%); HRMS (EI) for C$_{16}$H$_{13}$O$_4$N$_3$S (M$^+$): calcd 343.0627. found 343.0626.

(E)-3-(3-(2,3-Dihydro-1H-pyrrolo[2,3-b]pyridin-1-ylsulfonyl)phenyl)-N-hydroxyacrylamide (8)

The title compound was obtained in 10% overall yield from compound 35h in a manner similar to that described for the preparation of 3: mp=228-230° C.; $^1$H NMR (500 MHz, CD$_3$OD and CDCl$_3$) δ 3.04 (t, J=8.0 Hz, 2H), 4.04 (t, J=8.0 Hz, 2H), 6.50 (dd, J=5.0, 8.0 Hz, 1H), 7.45 (d, J=7.5 Hz, 1H), 7.51 (d, J=7.5 Hz, 1H), 7.55 (d, J=16.0 Hz, 1H), 7.72 (d, J=7.0 Hz, 1H), 7.97 (d, J=8.0 Hz, 1H), 8.00 (d, J=8.0 Hz, 1H), 8.05 (d, J=4.5 Hz, 1H), 8.21 (s, 1H); MS (EI) m/z: 347.0 (M$^+$, 0.90), 116 (100%); HRMS (EI) for C$_{16}$H$_{15}$O$_4$N$_3$S (M$^+$) calcd 345.3730. found 345.0783.

Scheme 2 below shows the synthetic route of preparing Compounds 9-13 of this invention.

In this scheme, reagents and conditions are as follows: (a) 4-bromobenzenesulfonyl chloride, KOH, TBAHS, CH$_2$Cl$_2$, RT, 88%-93%; (b) NaHCO$_3$, PPh$_3$, Pd(OAc)$_2$, tert-butyl acrylate, NEt$_3$, DMF, 80° C., 35%-83%; (c) TFA, RT, 97%-53%; and (d) i. PyBOP, Et$_3$N, NH$_2$OTHP, DMF, RT; ii. 5% TFA, MeOH, RT, 9%-44%.

The preparation of Compounds 9-13 is describe in detail below.

Scheme 2. Synthesis of Compounds 9-13

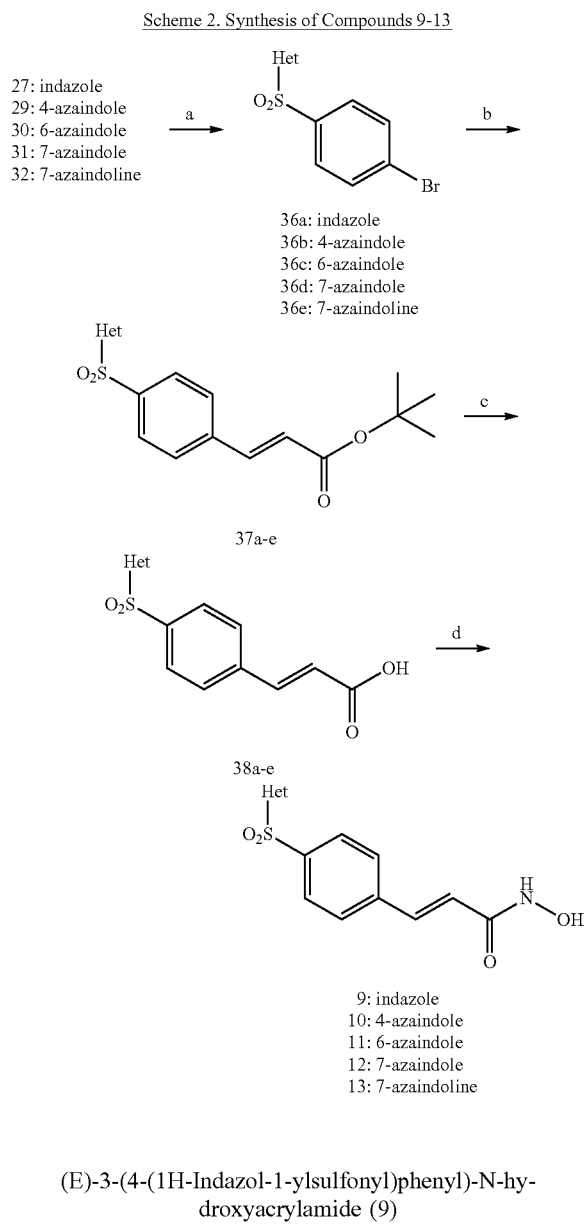

27: indazole
29: 4-azaindole
30: 6-azaindole
31: 7-azaindole
32: 7-azaindoline

36a: indazole
36b: 4-azaindole
36c: 6-azaindole
36d: 7-azaindole
36e: 7-azaindoline 37a-e 38a-e 9: indazole
10: 4-azaindole
11: 6-azaindole
12: 7-azaindole
13: 7-azaindoline

(E)-3-(4-(1H-Indazol-1-ylsulfonyl)phenyl)-N-hydroxyacrylamide (9)

To a mixture of indazole (500 mg, 4.23 mmol), potassium hydroxide (470 mg, 8.46 mmol), and tetrabutylammonium hydrogensulfate (220 mg, 0.63 mmol) in dry $CH_2Cl_2$ (30 mL) was and, after addition of 4-bromobenzenesulfonyl chloride (1300 mg, 5.10 mmol) and stirred overnight. The mixture was filtered off and added water followed by extraction with $CH_2Cl_2$ (3×30 mL). The organic layer was collected and dried over anhydrous $MgSO_4$ and concentrated in vacuo to yield an oily product. The residue was purified by a flash column over silica gel (ethyl acetate:n-hexane=3:1; $R_f$=0.30) to give 1250 mg (yield 88%) of 36a as a solid: $^1$H NMR (500 MHz, $CDCl_3$) δ 7.11 (td, J=2.5, 8.5 Hz, 1H), 7.31 (dd, J=2.0, 7.5 Hz, 1H), 7.64 (dd, J=9.0, 16.0 Hz, 2H), 7.68 (d, J=9.0 Hz, 2H), 7.96 (dd, J=1.5, 7.0 Hz, 2H), 8.62 (s, 1H).

A mixture of 36a (1270 mg, 3.78 mmol), tert-butyl acrylate (0.60 mL, 4.54 mmol), triethylamine (0.75 mL, 6.45 mmol), triphenylphosphine (490 mg, 1.90 mmol), palladium acetate (420 mg, 1.90 mmol), and sodium bicarbonate (320 mg, 3.78 mmol) was heated to 80° C. in DMF (2 mL) for 5 hours. The mixture was then filtered and the filtrate was extracted with water (30 mL) and $CH_2Cl_2$ (3×30 mL). The organic layer was collected and dried over anhydrous $MgSO_4$. After removal of $MgSO_4$ through filtration, the filtrate was concentrated in vacuo to yield an oily product, which was purified by a flash column over silica gel (1:10 EtOAc/n-hexane) to give 680 mg (47%) of 37a as a yellow solid: $^1$H NMR (500 MHz, $CDCl_3$) δ 1.57 (s, 9H), 6.38 (d, J=16.0 Hz, 1H), 7.46 (t, J=7.5 Hz, 1H), 7.50-7.59 (m, 3H), 7.70 (dd, J=3.5, 8.5 Hz, 1H), 7.98 (dd, J=9.0, 17.0 Hz, 2H), 8.19-8.23 (m, 2H).

To a solid of compound 37a (560 mg, 1.46 mmol) and trifluoroacetic acid (4.80 mL, 0.07 mmol) and stirred for 30 minutes followed by addition of water (20 mL) to afford a white solid. The resultant solid was collected by filtration and purified by recrystallization with methanol to give 410 mg (86%) of 38a as a white solid: $^1$H NMR (500 MHz, $CD_3OD$) δ 6.44 (d, J=16.0 Hz, 1H), 7.35 (t, J=8.0 Hz, 1H), 7.53-7.62 (m, 4H), 7.71 (d, J=8.0 Hz, 1H), 7.94 (d, J=8.0 Hz, 2H), 8.16 (d, J=8.5 Hz, 1H), 8.23 (s, 1H).

A mixture of compound 38a (640 mg, 1.96 mmol), PyBOP (1170 mg, 2.31 mmol), DMF (1 mL), $NH_2OTHP$ (230 mg, 1.96 mmol), and triethylamine (1 mL, 5.35 mmol) was stirred under nitrogen for 5 hours, then filtered, and the filtrate was extracted with water (30 mL) and $CH_2Cl_2$ (30 mL×3). The organic layer was collected and dried over anhydrous $MgSO_4$. After removal of $MgSO_4$ through filtration, the filtrate was concentrated in vacuo to yield an oily residue, which was purified with a flash column over silica gel (ethyl acetate:n-hexane=1:2; $R_f$=0.40) to take white solid. Then solid was added 5% trifluoroacetic acid (60 mL) and methanol (3 mL), then stirred for 30 minutes. This reaction mixture was concentrated in vacuo and filtered to yield a white product, which was washed with water/$CH_2Cl_2$ to give 110 mg (16%) of 9 as a purple solid: mp=140-142° C.; $^1$H NMR (500 MHz, $CD_3OD$ and DMSO) δ 6.53 (d, J=16.0 Hz, 1H), 7.39 (t, J=7.5 Hz, 1H), 7.52 (d, J=16.0 Hz, 1H), 7.63 (t, J=8.0 Hz, 1H), 7.67 (d, J=8.0 Hz, 2H), 7.79 (d, J=8.0 Hz, 1H), 7.94 (d, J=8.5 Hz, 2H), 8.20 (d, J=9.0 Hz, 1H), 8.34 (s, 1H); HRMS (EI) for $C_{16}H_{13}O_4N_3S$ (M$^+$) calcd 343.0627. found 343.0627.

(E)-3-(4-(1H-Pyrrolo[3,2-b]pyridin-1-ylsulfonyl)phenyl)-N-hydroxyacrylamide (10)

The title compound was obtained in 44% overall yield from compound 38b in a manner similar to that described above for the preparation of 9: mp=188-190° C. $^1$H NMR (500 MHz, $CD_3OD$): δ 6.57 (d, J=16.0 Hz, 1H), 7.01 (d, J=3.5 Hz, 1H), 7.54 (d, J=15.5 Hz, 1H), 7.63 (dd, J=5.5, 8.5 Hz, 1H), 7.74 (d, J=8.5 Hz, 2H), 8.07 (d, J=8.5 Hz, 2H), 8.28 (d, J=4.0 Hz, 1H), 8.61 (d, J=5.0 Hz, 1H), 8.76 (d, J=8.5 Hz, 1H).

(E)-3-(4-(1H-Pyrrolo[2,3-c]pyridin-1-ylsulfonyl)phenyl)-N-hydroxyacrylamide (11)

The title compound was obtained in 22% overall yield from compound 38c in a manner similar to that described for the preparation of 9: mp=167-169° C.; $^1$H NMR (500 MHz, $CD_3OD$) δ 6.53 (d, J=16.0 Hz, 1H), 7.15 (d, J=3.5 Hz, 1H), 7.54 (d, J=15.5 Hz, 1H), 7.76 (d, J=8.5 Hz, 2H), 8.12 (d, J=6.5 Hz, 1H), 8.14 (d, J=8.5 Hz, 2H), 8.46 (t, J=3.5 Hz, 1H), 8.48 (s, 1H), 9.51 (s, 1H); HRMS (ESI) for $C_{16}H_{13}O_4N_3S$ (M-H) calcd 343.0627. found 342.0542.

(E)-3-(4-(1H-Pyrrolo[2,3-b]pyridin-1-ylsulfonyl) phenyl)-N-hydroxyacrylamide (12)

The title compound was obtained in 9% overall yield from compound 38d in a manner similar to that described for the preparation of 9: mp=169-170° C.; $^1$H NMR (500 MHz, CD$_3$OD) δ 6.54 (d, J=16.0 Hz, 1H), 6.74 (d, J=3.5 Hz, 1H), 7.25 (dd, J=5.0, 9.0 Hz, 1H), 7.53 (d, J=16.0 Hz, 1H), 7.68 (d, J=8.5 Hz, 2H), 7.81 (d, J=4.0 Hz, 1H), 8.97 (dd, J=1.5, 8.0 Hz, 1H), 8.11 (d, J=8.5 Hz, 2H), 8.31 (dd, J=1.0, 4.5 Hz, 1H); HRMS (EI) for C$_{16}$H$_{13}$O$_4$N$_3$S (M$^+$) calcd 343.3571. found 343.0627.

(E)-3-(4-(2,3-Dihydro-1H-pyrrolo[2,3-b]pyridin-1-ylsulfonyl)phenyl)-N-hydroxyacrylamide (13)

The title compound was obtained in 28% overall yield from compound 38e in a manner similar to that described for the preparation of 9: mp=220-223° C.; $^1$H NMR (500 MHz, CD$_3$OD and DMSO) δ 3.04 (t, J=8.0 Hz, 2H), 4.04 (t, J=8.0 Hz, 2H), 6.54 (d, J=16.0 Hz, 1H), 6.51 (dd, J=5.0, 7.5 Hz, 1H), 7.49 (d, J=9.0 Hz, 1H), 7.53-7.58 (m, 2H), 7.77 (d, J=8.0 Hz, 1H), 7.98 (d, J=7.5 Hz, 1H), 8.04 (d, J=5.0 Hz, 1H), 8.23 (s, 1H); HRMS (EI) for C$_{16}$H$_{13}$O$_4$N$_3$S (M$^+$) calcd 345.3571. found 345.0783.

Shown below in Scheme 3 is the synthetic route of preparing Compounds 14-21 of this invention.

Reagents and conditions are as follows: (a) i. methyl 4-chloromethylbenzoate, NaH, DMF, RT; ii. 1N KOH, MeOH, reflux; and (b) o-phenylenediamine, N-(3-dimethylaminopropyl)-N'-ethylcarbodiimide hydrochloride (EDC), hydroxybenzotriazole (HOBt), TEA, DMF, RT.

Scheme 3. Synthesis of Compounds 14-21

25: indole
26: indoline
27: indazole
29: 4-azaindole
39: 5-azaindole
30: 6-azaindole
31: 7-azaindole
32: 7-azaindoline

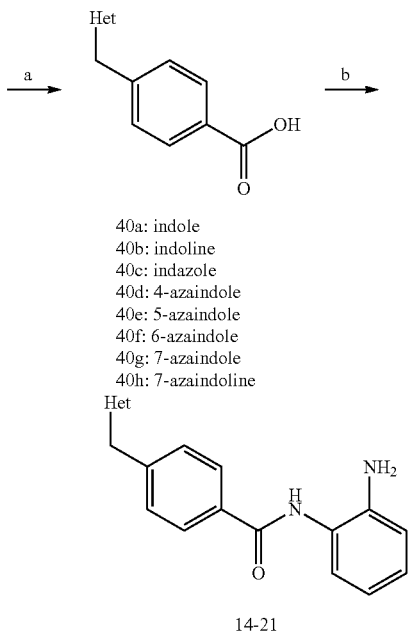

40a: indole
40b: indoline
40c: indazole
40d: 4-azaindole
40e: 5-azaindole
40f: 6-azaindole
40g: 7-azaindole
40h: 7-azaindoline 14-21

The preparation of Compounds 14-21 is described in detail below.

4-((1H-Indol-1-yl)methyl)-N-(2-aminophenyl)benzamide (14)

A mixture of indole (500 mg, 4.27 mmol), potassium hydroxide (480 mg, 8.54 mmol), and NH$_2$OTHF (220 mg, 0.643 mmol) in dry CH$_2$Cl$_2$ (30 mL) was stirred for 30 minutes under a nitrogen atmosphere, after which methyl-4-(chloromethyl)benzoate (950 mg, 5.12 mmol) was added. The mixture was stirred overnight and filtered. Water was added to the filtrate followed by extraction with CH$_2$Cl$_2$ (30 mL×3). The organic layer was collected and dried over anhydrous MgSO$_4$ and concentrated in vacuo to yield an oily product. To the resultant residue was added lithium hydroxide (210 mg, 8.58 mmol) and subsequently heated to 100° C. for 2 h in a solvent containing MeOH (7.6 mL) and water (7.6 mL). The mixture was filtered off and added water followed by extraction with CH$_2$Cl$_2$ (30 mL×3). The organic layer was collected and dried over anhydrous MgSO$_4$ and concentrated in vacuo to yield an oily product, which was purified with a flash column over silica gel (ethyl acetate:n-hexane=1:1; R$_f$=0.325) to afford 40a (570 mg, 79%) as a solid. $^1$H NMR (500 MHz, CD$_3$OD): δ 5.40 (s, 2H), 6.59 (d, J=3.0 Hz, 1H), 7.11-7.25 (m, 6H), 7.67 (d, J=8.0 Hz, 1H), 8.02 (d, J=8.5 Hz, 2H).

To a mixture of compound 40a (570 mg, 2.27 mmol) was added 4-methylmorpholine (0.5 mL, 7.95 mmol) in dried DMF (2 mL) stirred 30 minutes with nitrogen gas. The reaction mixture was added HOBt (460 mg, 3.41 mmol) and EDC (650 mg, 3.41 mmol) and o-phenylenediamine (270 mg, 2.50 mmol) and stirred for 5 hours, which was then filtered. To the filtrate was added water followed by extraction with CH$_2$Cl$_2$ (30 mL×3). The organic layer was collected and dried over anhydrous MgSO$_4$ and concentrated in vacuo to yield an oily product, which was purified with a flash column over silica gel (ethyl acetate:n-hexane=1:1; R$_f$=0.22) and recrystallization with ethyl acetate/acetone to afford 14 (240 mg, 31%) as a solid. mp=207-210° C. $^1$H NMR (500 MHz, CD$_3$OD): δ 5.48 (s, 2H), 6.51 (d, J=3.0 Hz, 1H), 6.73 (t, J=8.0 Hz, 1H), 6.86 (dd, J=1.0, 8.0 Hz, 1H), 6.99-7.09 (m, 3H), 7.14 (d, J=8.0 Hz, 1H), 7.22 (d, J=8.5 Hz, 2H), 7.26 (d, J=8.0 Hz, 1H), 7.29 (d, J=3.5 Hz, 1H), 7.55 (d, J=7.5 Hz, 1H), 7.87 (d, J=8.5 Hz, 2H). MS (EI) m/z: 341.0 (M$^+$, 39.63%), 57 (100%). HRMS (EI) for C$_{21}$H$_{18}$ON$_4$ (M$^+$): calcd, 341.4058. found 341.1529.

N-(2-Aminophenyl)-4-(indolin-1-ylmethyl)benzamide (15)

The title compound was obtained in 31% overall yield from compound 40b in a manner similar to that described for the preparation of 14: $^1$H NMR (500 MHz, CD$_3$OD): δ 2.99 (t, J=8.5 Hz, 2H), 3.37 (t, J=8.5 Hz, 2H), 4.38 (s, 2H), 6.57 (d, J=8.0 Hz, 1H), 6.66 (t, J=7.5 Hz, 1H), 6.76 (t, J=7.5 Hz, 1H), 6.90 (d, J=7.5 Hz, 1H), 7.03 (t, J=7.5 Hz, 1H), 7.07-7.10 (m, 2H), 7.23 (d, J=7.0 Hz, 1H), 7.56 (d, J=8.5 Hz, 2H), 8.00 (d, J=8.0 Hz, 2H). MS (EI) m/z: 343.0 (M$^+$, 100%). HRMS (EI) for C$_{22}$H$_{21}$ON$_3$ (M$^+$): calcd, 343.4216. found, 343.1683.

4-((1H-Indazol-1-yl)methyl)-N-(2-aminophenyl) benzamide (16)

The title compound was obtained in 30% overall yield from compound 40c in a manner similar to that described for the preparation of 14: mp=185-188° C. $^1$H NMR (500 MHz, CDCl$_3$ and CD$_3$OD): δ 5.46 (s, 2H), 6.58 (t, J=8.0 Hz, 1H), 6.64 (d, J=8.0 Hz, 1H), 6.86 (t, J=8.0 Hz, 1H), 6.94-6.98 (m, 2H), 7.04 (d, J=8.0 Hz, 2H), 7.17 (d, J=5.5 Hz, 2H), 7.55 (d, J=8.0 Hz, 2H), 7.67 (d, J=8.0 Hz, 2H), 7.84 (s, 1H). MS (EI) m/z: 342.0 (M$^+$, 32.79%), 235 (100%). MS (EI) m/z: 342.0

(M+, 32.79%), 235 (100%). HRMS (EI) for C₂₁H₁₈ON₄ (M+): calcd, 342.3938. found 342.1478.

4-((1H-Pyrrolo[3,2-b]pyridin-1-yl)methyl)-N-(2-aminophenyl)-benzamide (17)

The title compound was obtained in 23% overall yield from compound 45d in a manner similar to that described for the preparation of 14: mp=116-118° C. ¹H NMR (500 MHz, CDCl₃ and CD₃OD): δ 5.26 (s, 2H), 6.53 (d, J=3.5 Hz, 1H), 6.62 (t, J=8.0 Hz, 1H), 6.67 (d, J=8.0 Hz, 1H), 6.89 (t, J=8.0 Hz, 1H), 6.53 (dd, J=5.0, 8.5 Hz, 1H), 7.01 (d, J=7.0 Hz, 1H), 7.02 (d, J=8.0 Hz, 2H), 7.31 (d, J=3.5 Hz, 1H), 7.44 (d, J=8.5 Hz, 1H), 7.72 (d, J=8.0 Hz, 2H), 8.15 (d, J=4.5 Hz, 1H). MS (EI) m/z: 342.0 (M+, 89.71%), 208 (100%). HRMS (EI) for C₂₁H₁₈ON₄ (M+): calcd, 342.3938. found 342.1483.

4-((1H-Pyrrolo[3,2-c]pyridin-1-yl)methyl)-N-(2-aminophenyl)benzamide (18)

The title compound was obtained in 32% overall yield from compound 40e in a manner similar to that described for the preparation of 14: mp=165-167° C. ¹H NMR (500 MHz, CD₃OD): δ 5.59 (s, 2H), 6.76 (t, J=7.5 Hz, 1H), 6.81 (d, J=3.5 Hz, 1H), 6.89 (d, J=8.0 Hz, 1H), 7.07 (t, 7.0 Hz, 1H), 7.16 (d, J=7.5 Hz, 1H), 7.31 (d, J=8.0 Hz, 2H), 7.51 (d, J=6.0 Hz, 1H), 7.55 (d, J=3.0 Hz, 1H), 7.93 (d, J=8.0 Hz, 2H), 8.17 (d, J=6.0 Hz, 1H), 8.86 (s, 1H). MS (EI) m/z: 342.0 (M+, 21.0%), 207 (100%). HRMS (EI) for C₂₁H₁₈ON₄ (M+): calcd, 342.3938. found 342.1479.

4-((1H-Pyrrolo[2,3-c]pyridin-1-yl)methyl)-N-(2-aminophenyl)-benzamide (19)

The title compound was obtained in 27% overall yield from compound 40f in a manner similar to that described for the preparation of 14: mp=154-155° C. ¹H NMR (500 MHz, CD₃OD): δ 5.64 (s, 2H), 6.65 (d, J=3.0 Hz, 1H), 6.74 (t, J=7.5 Hz, 1H), 6.87 (d, J=8.5 Hz, 1H), 7.05 (t, J=8.0 Hz, 1H), 7.15 (d, J=8.0 Hz, 1H), 7.31 (d, J=8.0 Hz, 2H), 7.63 (d, J=5.5 Hz, 1H), 7.67 (d, J=3.0 Hz, 1H), 7.92 (d, J=8.0 Hz, 2H), 8.08 (d, J=4.0 Hz, 1H), 8.66 (s, 1H). MS (EI) m/z: 342.0 (M+, 21.11%), 207 (100%). HRMS (EI) for C₂₁H₁₈ON₄ (M+): calcd, 342.3938. found 342.1480.

4-((1H-Pyrrolo[2,3-b]pyridin-1-yl)methyl)-N-(2-aminophenyl)benzamide (20)

The title compound was obtained in 37% overall yield from compound 40g in a manner similar to that described for the preparation of 14: mp=158-159° C. ¹H NMR (500 MHz, CDCl₃ and CD₃OD): δ 5.29 (s, 2H), 6.28 (d, J=3.5 Hz, 1H), 6.51 (t, J=7.5 Hz, 1H), 6.58 (d, J=3.0 Hz, 1H), 6.78 (t, J=6.5 Hz, 1H), 6.85 (dd, J=5.0, 8.0 Hz, 1H), 6.91 (d, J=8.0 Hz, 1H), 6.98 (d, J=8.0 Hz, 2H), 7.00 (d, J=3.5 Hz, 1H), 7.61 (d, J=8.0 Hz, 2H), 7.72 (dd, 1.5, 8.0 Hz, 1H), 7.97 (d, J=3.5 Hz, 1H). MS (EI) m/z: 342.0 (M+, 72.6%), 147 (100%).

N-(2-Aminophenyl)-4-((2,3-dihydro-1H-pyrrolo[2,3-b]pyridin-1-yl)methyl)benzamide (21)

The title compound was obtained in 49% overall yield from compound 40h in a manner similar to that described for the preparation of 14: mp=105-107° C. ¹H NMR (500 MHz, CD₃OD and DMSO): δ 2.99 (t, J=8.5 Hz, 2H), 3.42 (t, J=8.5 Hz, 2H), 4.17 (s, 2H), 4.63 (s, 2H), 6.47 (dd, J=5.5, 6.5 Hz, 1H), 6.77 (dd, J=5.0, 6.5 Hz, 1H), 6.82 (d, J=8.0 Hz, 1H), 7.05 (t, J=7.5 Hz, 1H), 7.22 (d, J=7.0 Hz, 1H), 7.31 (d, J=7.5 Hz, 1H), 7.43 (d, J=8.0 Hz, 2H), 7.86 (d, J=5.0 Hz, 1H), 7.97 (d, J=8.0 Hz, 2H), 9.21 (s, 1H). MS (EI) m/z: 344.0 (M+, 51.03%), 237 (100%). HRMS (EI) for C₂₁H₂₀ON₄ (M+): calcd, 344.4097. found, 344.1636.

Shown below in Scheme 4 is the synthetic route of preparing Compounds 22-24 of this invention.

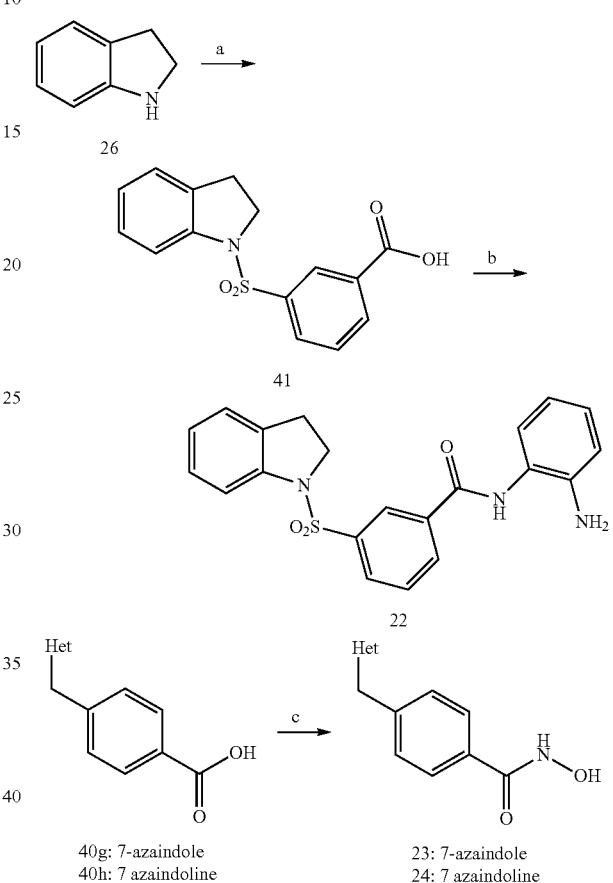

Scheme 4. Synthesis of Compounds 22-24

40g: 7-azaindole
40h: 7 azaindoline

23: 7-azaindole
24: 7 azaindoline

Reagents and conditions are as follows: (a) i. 3-chlorosulfonylbenzoic acid methyl ester, NaH, DMF, RT; ii. 1N KOH, MeOH, reflux; (b) o-phenylenediamine, EDC, HOBt, TEA, DMF, RT; and (c) i. O-benzylhydroxylamine, EDC, HOBt, TEA, DMF, RT; ii. Pd/C, H₂, MeOH, RT.

The preparation of Compounds 22-24 is describe in detail below.

N-(2-Aminophenyl)-4-(indolin-1-ylsulfonyl)benzamide (22)

To a mixture of 3-(chlorosulfonyl)benzoic acid (220 mg, 1.01 mmol), water (30 mL) and indoline (120 mg, 1.01 mmol) was added NaHCO₃ to adjust the pH of the mixture to 8. After stirred for 2 hours, the mixture was added HCl until pH=3, then concentrated in vacuo, and filtered to yield a white product, which was purified by recrystallization in ethanol to afford 41 (100 mg, 33%) as a white solid. ¹H NMR (500 MHz, CD3OD): δ 2.92 (t, J=8.0 Hz, 2H), 3.98 (t, J=8.0 Hz, 2H), 7.00 (t, J=7.4 Hz, 1H), 7.09 (d, J=7.4 Hz, 1H), 7.23 (t, J=7.8 Hz, 1H), 7.57 (t, J=7.8 Hz, 1H), 7.65 (t, J=8.1 Hz, 1H), 8.01 (d, J=7.9 Hz, 1H), 8.27 (d, J=7.8 Hz, 1H), 8.54 (s, 1H).

41

Compound 41 (100 mg, 0.33 mmol) was added to a 4-methylmorpholine (0.2 mL, 1.38 mmol) solution in dried DMF (1 mL), which was stirred for 30 minutes under a nitrogen atmosphere. The resultant reaction mixture was added HOBt (80 mg, 0.59 mmol), EDC (110 mg. 0.59 mmol), and o-phenylenediamine (50 mg. 0.43 mmol) and stirred for 5 hours, after which it was filtered. Water was added to the filtrate followed by extraction with $CH_2Cl_2$ (30 mL×3). The organic layer was collected, dried over anhydrous $MgSO_4$, and concentrated in vacuo to yield an oily product, which was purified by a flash column over silica gel (ethyl acetate:n-hexane=1:2; $R_f$=0.19) to afford 22 (100 mg, 77%) as a white solid. mp=192-193° C. $^1$H NMR (500 MHz, $CDCl_3$ and $CD_3OD$): δ 2.74 (t, J=8.4 Hz, 2H), 3.81 (t, J=8.4 Hz, 2H), 6.65 (t, J=7.5 Hz, 1H), 6.70 (d, J=8.0 Hz, 1H), 6.82 (t, J=8.0 Hz, 1H), 6.93 (d, J=7.4 Hz, 1H), 6.94 (d, J=7.5 Hz, 1H), 7.02 (d, J=7.5 Hz, 1H), 7.03 (d, J=7.4 Hz, 1H), 7.41 (t, J=8.0 Hz, 1H), 7.44 (d, J=8.0 Hz, 1H), 7.74 (d, J=7.5 Hz, 1H), 8.00 (d, J=8.0 Hz, 1H), 8.24 (s, 1H). MS (EI) m/z: 393.0 (M$^+$, 68.13%), 116 (100%). HRMS (EI) for $C_{21}H_{19}O_3N_3S$ (M$^+$): calcd, 393.4589. found, 393.1143.

N-Hydroxy-4-pyrrolo[2,3-b]pyridin-1-ylmethyl-benzamide (23)

A mixture of 40g (0.51 g, 4.2 mmol), EDC (1.82 g, 11.7 mmol), HOBt (1.68 g, 12.4 mmol), NMM (1.2 mL), o-benzylhydroxyamine (0.67 g, 4.2 mmol), and DMF (10 mL) was stirred at room temperature for 1 hour. To the mixture was added water (30 mL), and then extracted with ethyl acetate (30 mL×3). The organic layers were collected, dried, and concentrated to afford an oily residue. The resultant residue was added to Pd/C and MeOH (20 mL), which was stirred under hydrogen at room temperature for 1 hour, and then filtered. The filtrate was concentrated and purified with a column chromatography to afford a white solid (0.44 g, 39%). $^1$H NMR (500 MHz, $CD_3OD$): δ 5.55 (s, 2H), 6.55 (d, J=3.5 Hz, 1H), 7.11-7.14 (m, 1H), 7.21 (d, J=8.0 Hz, 2H), 7.40 (d, J=3.5 Hz, 1H), 7.65 (d, J=8.0 Hz, 2H), 8.01 (dd, J=1.0, 8.0 Hz, 1H), 8.21 (dd, J=1.0, 4.5 Hz, 1H).

4-(2,3-Dihydro-pyrrolo[2,3-b]pyridin-1-ylmethyl)-N-hydroxy-benzamide (24)

The title compound was obtained in 36% overall yield from compound 40h in a manner similar to that described for the preparation of 23: $^1$H NMR (500 MHz, $CD_3OD$): δ 2.99 (t, J=8.5 Hz, 2H), 3.43 (t, J=8.5 Hz, 2H), 4.58 (s, 2H), 6.50 (t, J=6.5 Hz, 1H), 7.29 (t, J=7.0 Hz, 1H), 7.39 (d, J=8.0 Hz, 2H), 7.70-7.73 (m, 3H).

Shown below in Scheme 5 is the synthetic route of preparing Compounds 2a-2p, 3a-3p, 4a-4p, and 5a-5p of this invention.

Scheme 5. Synthesis of Compounds 2a-2p, 3a-3p, 4a-4p, and 5a-5p

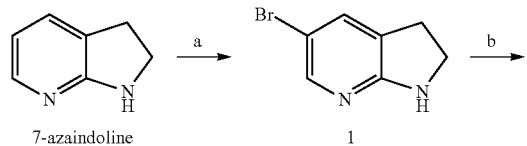

7-azaindoline            1

-continued

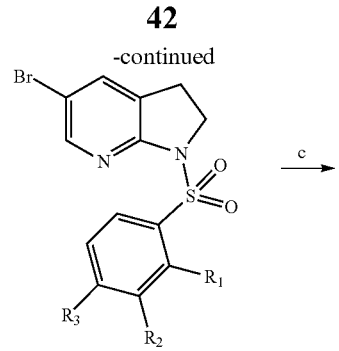

2a $R_1$ = H, $R_2$ = H, $R_3$ = H    2i $R_1$ = H, $R_2$ = H, $R_3$ = $NO_2$
2b $R_1$ = H, $R_2$ = H, $R_3$ = $OCH_3$    2j $R_1$ = H, $R_2$ = $NO_2$, $R_3$ = H
2c $R_1$ = H, $R_2$ = $OCH_3$, $R_3$ = H    2k $R_1$ = H, $R_2$ = H, $R_3$ = Br
2d $R_1$ = H, $R_2$ = $OCH_3$, $R_3$ = $OCH_3$    2l $R_1$ = H, $R_2$ = Br, $R_3$ = H
2e $R_1$ = H, $R_2$ = H, $R_3$ = F    2m $R_1$ = Br, $R_2$ = H, $R_3$ = H
2f $R_1$ = H, $R_2$ = F, $R_3$ = H    2n $R_1$ = H, $R_2$ = H, $R_3$ = CN
2g $R_1$ = H, $R_2$ = H, $R_3$ = Cl    2o naphthalenyl
2h $R_1$ = H, $R_2$ = Cl, $R_3$ = H    2p dansyl

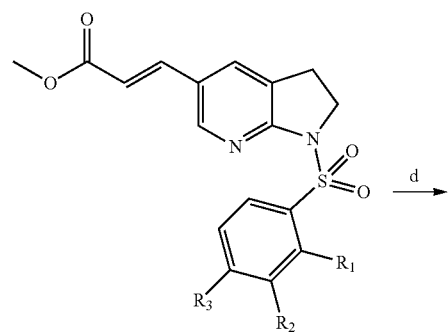

3a $R_1$ = H, $R_2$ = H, $R_3$ = H    3i $R_1$ = H, $R_2$ = H, $R_3$ = $NO_2$
3b $R_1$ = H, $R_2$ = H, $R_3$ = $OCH_3$    3j $R_1$ = H, $R_2$ = $NO_2$, $R_3$ = H
3c $R_1$ = H, $R_2$ = $OCH_3$, $R_3$ = H    3k $R_1$ = H, $R_2$ = H, $R_3$ = -$CHCHCOOCH_3$
3d $R_1$ = H, $R_2$ = $OCH_3$, $R_3$ = $OCH_3$    3l $R_1$ = H, $R_2$ = -$CHCHCOOCH_3$, $R_3$ = H
3e $R_1$ = H, $R_2$ = H, $R_3$ = F    3m $R_1$ = -$CHCHCOOCH_3$, $R_2$ = H, $R_3$ = H
3f $R_1$ = H, $R_2$ = F, $R_3$ = H    3n $R_1$ = H, $R_2$ = H, $R_3$ = CN
3g $R_1$ = H, $R_2$ = H, $R_3$ = Cl    3o naphthalenyl
3h $R_1$ = H, $R_2$ = Cl, $R_3$ = H    3p dansyl

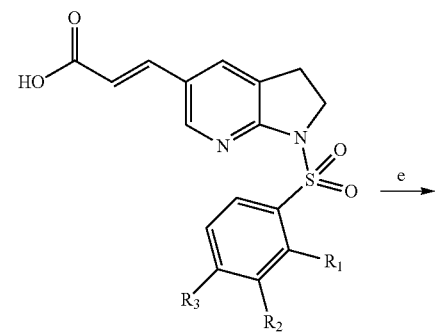

4a $R_1$ = H, $R_2$ = H, $R_3$ = H    4i $R_1$ = H, $R_2$ = H, $R_3$ = $NO_2$
4b $R_1$ = H, $R_2$ = H, $R_3$ = $OCH_3$    4j $R_1$ = H, $R_2$ = $NO_2$, $R_3$ = H
4c $R_1$ = H, $R_2$ = $OCH_3$, $R_3$ = H    4k $R_1$ = H, $R_2$ = H, $R_3$ = -CHCHCOOH
4d $R_1$ = H, $R_2$ = $OCH_3$, $R_3$ = $OCH_3$    4l $R_1$ = H, $R_2$ = -CHCHCOOH, $R_3$ = H
4e $R_1$ = H, $R_2$ = H, $R_3$ = F    4m $R_1$ = -CHCHCOOH, $R_2$ = H, $R_3$ = H
4f $R_1$ = H, $R_2$ = F, $R_3$ = H    4n $R_1$ = H, $R_2$ = H, $R_3$ = CN
4g $R_1$ = H, $R_2$ = H, $R_3$ = Cl    4o naphthalenyl
4h $R_1$ = H, $R_2$ = Cl, $R_3$ = H    4p dansyl -continued

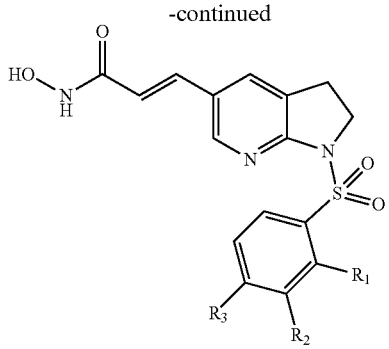

5a R₁ = H, R₂ = H, R₃ = H
5b R₁ = H, R₂ = H, R₃ = OCH₃
5c R₁ = H, R₂ = OCH₃, R₃ = H
5d R₁ = H, R₂ = OCH₃, R₃ = OCH₃
5e R₁ = H, R₂ = H, R₃ = F
5f R₁ = H, R₂ = F, R₃ = H
5g R₁ = H, R₂ = H, R₃ = Cl
5h R₁ = H, R₂ = Cl, R₃ = H
5i R₁ = H, R₂ = H, R₃ = NO₂
5j R₁ = H, R₂ = NO₂, R₃ = H
5k R₁ = H, R₂ = H, R₃ = -CHCHCONHOH
5l R₁ = H, R₂ = -CHCHCONHOH, R₃ = H
5m R₁ = -CHCHCONHOH, R₂ = H, R₃ = H
5n R₁ = H, R₂ = H, R₃ = CN
5o naphthalenyl
5p dansyl Reagents and Condition:

(a) Br₂, pyrinde, CH₂Cl₂, 0° C.

(b) substituted benzenesulfonyl chloride, pyridine, 90° C.

(c) Pd(OAc)₂, TPP, TEA, NaHCO₃, methyl acrylate, DMF, 120° C.

(d) 1M LiOH(aq.), LiOH, 40° C.

(e) EDC.HCl, HOBt, NMM, NH₂OTHP, DMF, RT, then 10% TFA(aq.), MeOH, RT

Compound 6a, 7a, 8a, 9a, and 10a of this invention can be prepared via the synthetic routes shown in Schemes 6, 7, and 8 below.

Scheme 6

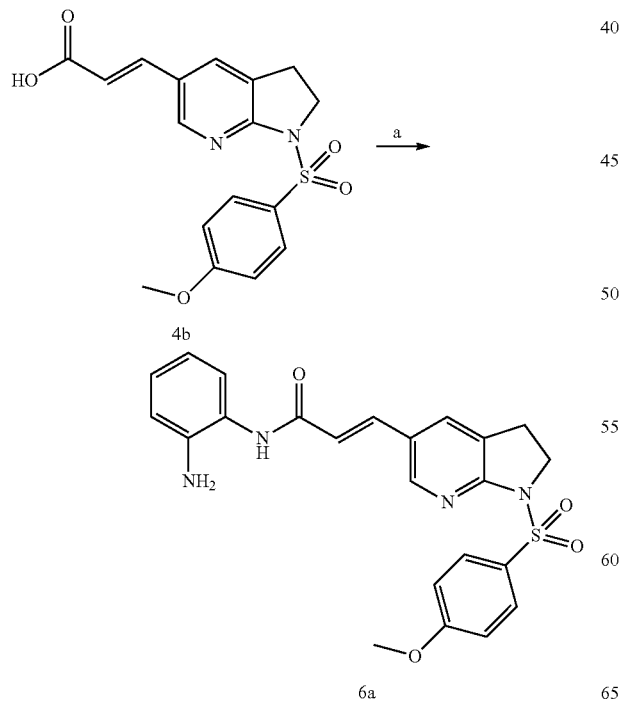

Reagent and Condition:

(a) EDC.HCl, HOBt, NMM, o-phenyldiamine, DMF, RT

Scheme 7

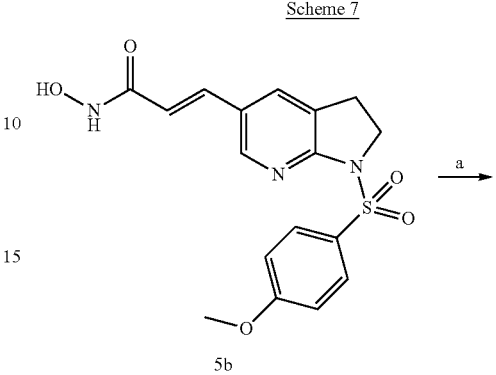

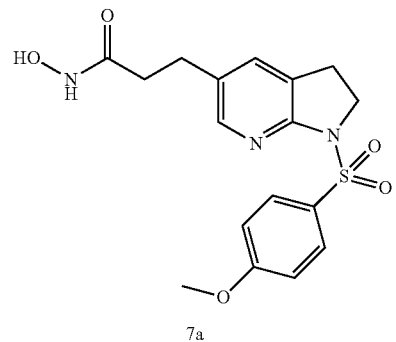

Reagent and Condition:

(a) 10% Pd/C, MeOH, H₂, RT

Scheme 8

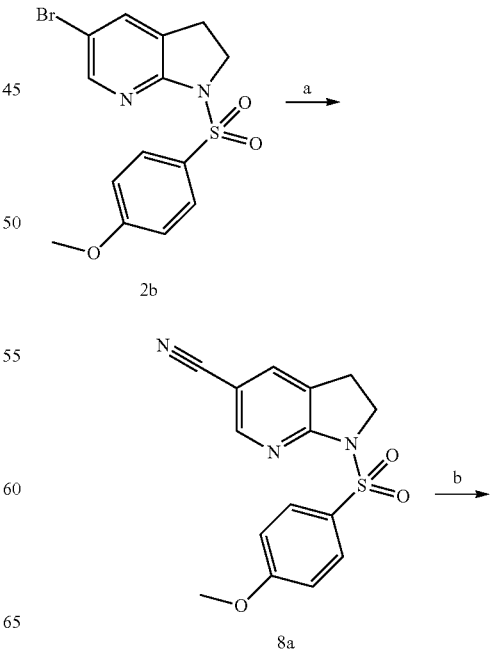

45

-continued

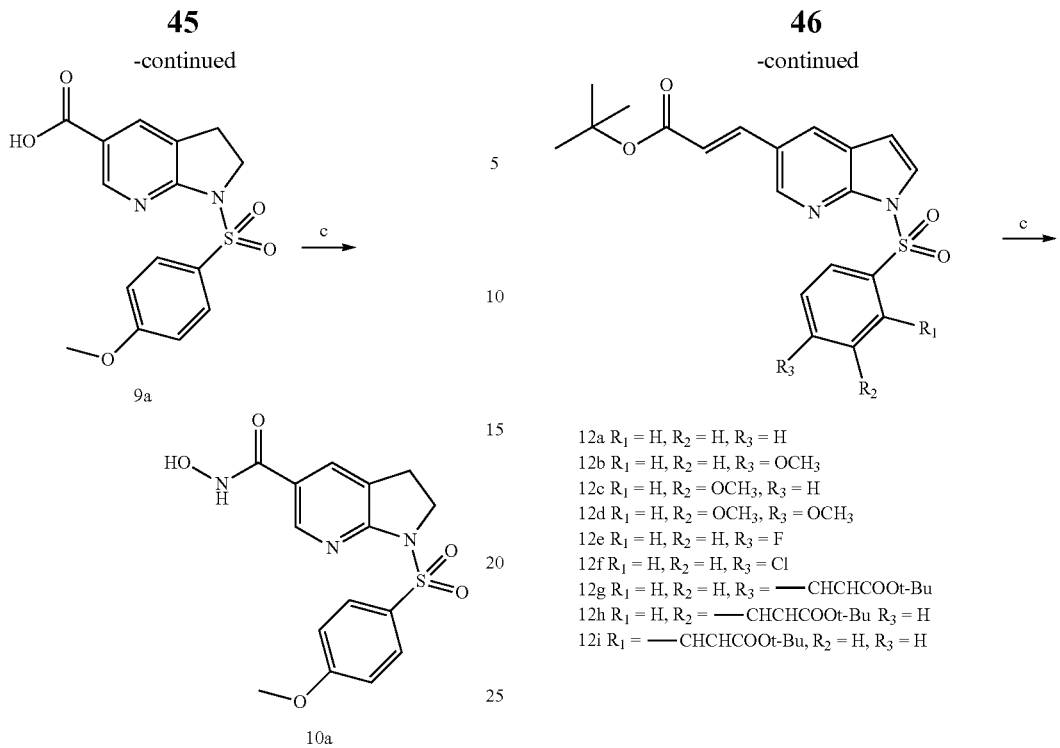

Reagents and Condition:
(a) CuCN, DMF, 150° C.
(b) 10% KOH(aq.), MeOH, reflux
(c) EDC.HCl, HOBt, NMM, NH$_2$OTHP, DMF, RT, then 10% TFA(aq.), MeOH, RT Compounds 11a-11i, 12a-12i, 13a-13i, and 14a-14i of this invention can be prepared using the synthetic route shown in Scheme 9 below.

46

-continued

12a R$_1$ = H, R$_2$ = H, R$_3$ = H
12b R$_1$ = H, R$_2$ = H, R$_3$ = OCH$_3$
12c R$_1$ = H, R$_2$ = OCH$_3$, R$_3$ = H
12d R$_1$ = H, R$_2$ = OCH$_3$, R$_3$ = OCH$_3$
12e R$_1$ = H, R$_2$ = H, R$_3$ = F
12f R$_1$ = H, R$_2$ = H, R$_3$ = Cl
12g R$_1$ = H, R$_2$ = H, R$_3$ = —CHCHCOOt-Bu
12h R$_1$ = H, R$_2$ = —CHCHCOOt-Bu R$_3$ = H
12i R$_1$ = —CHCHCOOt-Bu, R$_2$ = H, R$_3$ = H

Scheme 9

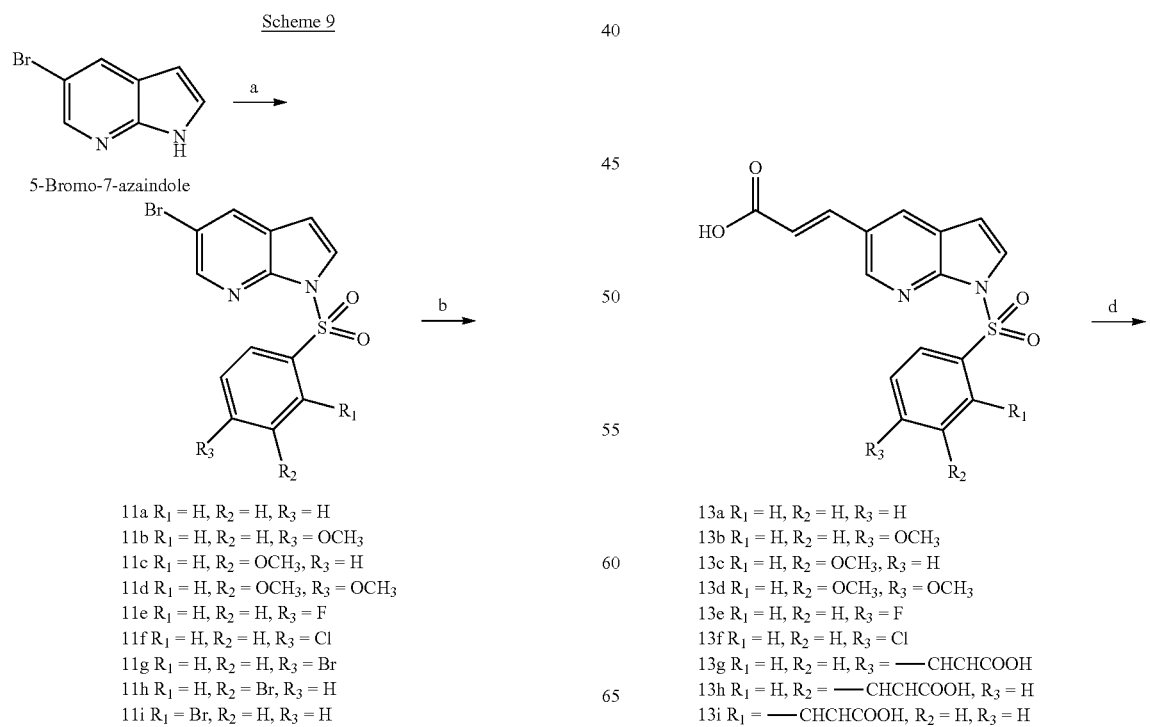

11a R$_1$ = H, R$_2$ = H, R$_3$ = H
11b R$_1$ = H, R$_2$ = H, R$_3$ = OCH$_3$
11c R$_1$ = H, R$_2$ = OCH$_3$, R$_3$ = H
11d R$_1$ = H, R$_2$ = OCH$_3$, R$_3$ = OCH$_3$
11e R$_1$ = H, R$_2$ = H, R$_3$ = F
11f R$_1$ = H, R$_2$ = H, R$_3$ = Cl
11g R$_1$ = H, R$_2$ = H, R$_3$ = Br
11h R$_1$ = H, R$_2$ = Br, R$_3$ = H
11i R$_1$ = Br, R$_2$ = H, R$_3$ = H

13a R$_1$ = H, R$_2$ = H, R$_3$ = H
13b R$_1$ = H, R$_2$ = H, R$_3$ = OCH$_3$
13c R$_1$ = H, R$_2$ = OCH$_3$, R$_3$ = H
13d R$_1$ = H, R$_2$ = OCH$_3$, R$_3$ = OCH$_3$
13e R$_1$ = H, R$_2$ = H, R$_3$ = F
13f R$_1$ = H, R$_2$ = H, R$_3$ = Cl
13g R$_1$ = H, R$_2$ = H, R$_3$ = —CHCHCOOH
13h R$_1$ = H, R$_2$ = —CHCHCOOH, R$_3$ = H
13i R$_1$ = —CHCHCOOH, R$_2$ = H, R$_3$ = H

47
-continued

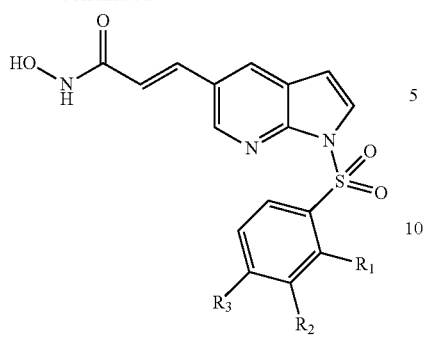

14a R₁ = H, R₂ = H, R₃ = H
14b R₁ = H, R₂ = H, R₃ = OCH₃
14c R₁ = H, R₂ = OCH₃, R₃ = H
14d R₁ = H, R₂ = OCH₃, R₃ = OCH₃
14e R₁ = H, R₂ = H, R₃ = F
14f R₁ = H, R₂ = H, R₃ = Cl
14g R₁ = H, R₂ = H, R₃ = —CHCHCONHOH
14h R₁ = H, R₂ = —CHCHCONHOH, R₃ = H
14i R₁ = —CHCHCONHOH, R₂ = H, R₃ = H

Reagents and Condition:

(a) NaH, substituted benzenesulfonyl chloride, DMF, RT (b) Pd(OAc)$_2$, TPP, TEA, NaHCO$_3$, t-Butyl acrylate, DMF, 120° C.

(c) TFA, RT (d) EDC.HCl, HOBt, NMM, NH$_2$OTHP, DMF, RT, then 10% TFA(aq.), MeOH, RT Provided below is the preparation of Compounds 1a, 2a-2p, 3a-3p, 4a-4p, 5a-5p, 6a, 7a, 8a, 9a, 10a, 11a-11i, 12a-12i, 13a-13i, and 14a-14i of this invention in detail.

5-Bromo-2,3-dihydro-1H-pyrrolo[2,3-b]pyridine (1a)

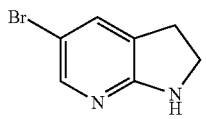

A mixture of 7-azaindoline (4 g, 33.29 mmol), pyridine (4 mL), and DCM (40 mL) was added Br$_2$ (1.72 mL, 33.29 mmol) in DCM (24 mL) using an additional funnel under ice bath in nitrogen and stirred for 2 hours. The reaction was then quenched with water and extracted with ethyl acetate (30 ml×3). The organic layer was collected, dried over anhydrous MgSO$_4$, and concentrated in vacuo to yield a dark brown product, which was purified by a flash column over silica gel (ethyl acetate:n-hexane=2:1, Rf=0.63) to afford 1 (4.88 g, 73.65%) as a yellow solid. $^1$H-NMR (500 MHz, CDCl$_3$): δ 3.06 (t, J=8.5 Hz, 2H), 3.64 (t, J=8.5 Hz, 2H), 7.31 (s, 1H), 7.85 (s, 1H).

48

5-Bromo-1-(phenylsulfonyl)-2,3-dihydro-1H-pyrrolo[2,3-b]pyridine (2a)

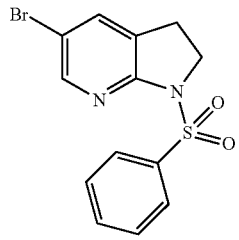 [SMILES: O=S(=O)(c1ccccc1)N1CCc2cc(Br)cnc21]

A mixture of 1a (0.35 g, 1.76 mmol), benzenesulfonyl chloride (0.34 mL, 2.64 mmol) and pyridine (3 mL) was refluxed overnight. The reaction was quenched with water and the mixture was extracted with ethyl acetate (30 mL×3). The organic layer was collected, dried over anhydrous MgSO$_4$, and concentrated in vacuo to yield a brown residue, which was purified by a flash column over silica gel (ethyl acetate:n-hexane=1:1, R$_f$=0.73) to afford 2a (0.47 g, 78.73%) as a yellow solid. $^1$H-NMR (500 MHz, CDCl$_3$): δ 3.04 (t, J=8.5 Hz, 2H), 4.08 (t, J=8.5 Hz, 2H), 7.46 (s, 1H), 7.49 (t, J=8.0 Hz, 2H), 7.58 (t, J=7.5 Hz, 1H), 8.08 (t, J=8.0 Hz, 2H), 8.18 (s, 1H).

(E)-Methyl 3-(1-(phenylsulfonyl)-2,3-dihydro-1H-pyrrolo[2,3-b]pyridin-5-yl)acrylate (3a)

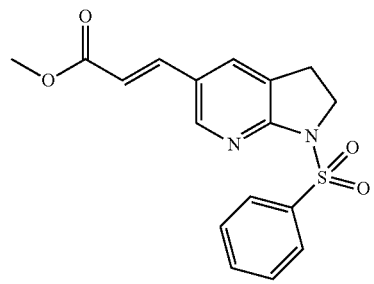 [SMILES: COC(=O)/C=C/c1cnc2c(c1)CCN2S(=O)(=O)c1ccccc1]

A mixture of 2a (0.47 g, 1.39 mmol), palladium acetate (0.03 g, 0.14 mmol), triphenylphosphine (0.07 g, 0.28 mmol), triethylamine (0.19 mL, 1.39 mmol), sodium bicarbonate (0.23 g, 2.78 mmol), and DMF (3 mL) was stirred for 10 minutes, and, after addition of methyl acrylate (0.15 mL, 1.67 mmol) at 120° C., was stirred again overnight. The mixture was subsequently purified with a flash column over silica gel (ethyl acetate:n-hexane=1:1, Rf=0.38) to afford 3a (0.38 g, 79.38%) as a yellow solid. $^1$H-NMR (500 MHz, CDCl$_3$): δ 3.09 (t, J=8.5 Hz, 2H), 3.80 (s, 3H), 4.12 (t, J=8.5 Hz, 2H), 6.30 (d, J=16.0 Hz, 1H), 7.50 (t, J=8.0 Hz, 2H), 7.56 (d, J=16.0 Hz, 1H), 7.57-7.60 (m, 2H), 8.12 (t, J=8.0 Hz, 2H), 8.25 (s, 1H).

(E)-3-(1-(Phenylsulfonyl)-2,3-dihydro-1H-pyrrolo[2,3-b]pyridin-5-yl)acrylic acid (4a)

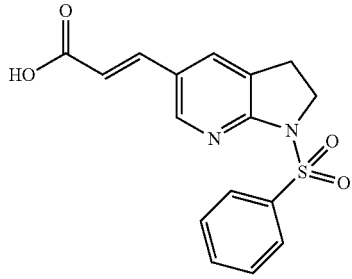 [SMILES: O=C(O)/C=C/c1cnc2c(c1)CCN2S(=O)(=O)c1ccccc1]

A mixture of 3a (0.38 g, 1.11 mmol), dioxane (5 mL), and 1 M LiOH aqueous solution (2.22 mL, 2.22 mmol) was stirred overnight at 40° C., after which the solvent was removed. Water and 3 N HCl aqueous solution were added sequentially to the resultant residue, followed by filtration. The filtrate was concentrated to yield 4a (0.36 g, 98.17%) as a white solid. $^1$H-NMR (500 MHz, DMSO-$d_6$): δ 3.08 (t, J=8.5 Hz, 2H), 4.08 (t, J=8.5 Hz, 2H), 6.44 (d, J=16.0 Hz, 1H), 7.50 (d, J=16.0 Hz, 1H), 7.58 (t, J=7.5 Hz, 2H), 7.68 (t, J=7.5 Hz, 1H), 7.94 (s, 1H), 8.01 (d, J=8.5 Hz, 2H), 8.26 (s, 1H).

(E)-N-hydroxy-3-(1-(phenylsulfonyl)-2,3-dihydro-1H-pyrrolo[2,3-b]pyridin-5-yl) acrylamide (5a)

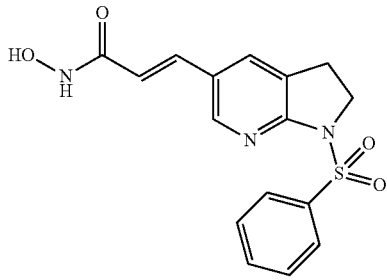 [SMILES: O=C(/C=C/c1cnc2c(c1)CCN2S(=O)(=O)c1ccccc1)NO]

A mixture of 4a (0.30 g, 0.91 mmol), EDC (0.26 g, 1.37 mmol), HOBt (0.15 g, 1.09 mmol), N-methylmorpholine (NMM; 0.24 mL, 2.18 mmol), and DMF (2 mL) was stirred for 10 minutes, and, after addition of o-(tetrahydro-2H-pyran-2-yl)hydroxylamine (0.13 g, 1.09 mmol) at room temperature, and was stirred again overnight. Removal of the solvent yielded a residue. The residue was purified with a flash column over silica gel (ethyl acetate: n-hexane=2:1, Rf=0.18) to obtain an oil product. MeOH (5 mL) and 10% TFA aqueous solution (5 mL) were added to the oil product, followed by stirring at room temperature overnight. H$_2$O was then added to precipitate a while product, which was collected by filtration to afford 5a (0.28 g, 89.09%). m.p. 198.1-199.0. $^1$H-NMR (500 MHz, DMSO-$d_6$): δ 3.08 (t, J=8.5 Hz, 2H), 4.06 (t, J=8.5 Hz, 2H), 6.35 (d, J=16.0 Hz, 1H), 7.36 (d, J=16.0 Hz, 1H), 7.58 (t, J=7.5 Hz, 2H), 7.67 (t, J=7.5 Hz, 1H), 7.74 (s, 1H), 8.00 (d, J=7.5 Hz, 2H), 8.19 (s, 1H).

5-Bromo-1-(4-methoxyphenylsulfonyl)-2,3-dihydro-1H-pyrrolo[2,3-b]pyridine (2b)

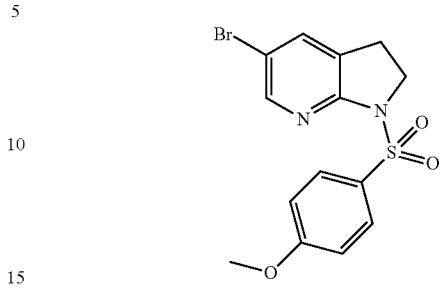

A mixture of 1a (0.99 g, 4.97 mmol), 4-methoxybenzenesulfonyl chloride (1.54 g, 7.4 mmol), and pyridine (4 mL) was refluxed overnight. The reaction was quenched with water and the mixture was extracted with ethyl acetate (30 mL×3). The organic layer was collected, dried over anhydrous MgSO$_4$, and concentrated in vacuo to yield a brown residue, which was purified with a flash column over silica gel (ethyl acetate:n-hexane=1:1, Rf=0.60) to afford 2b (0.96 g, 52.31%) as a yellow solid. $^1$H-NMR (500 MHz, CDCl$_3$): δ 3.02 (t, J=8.5 Hz, 2H), 3.84 (s, 3H), 4.05 (t, J=8.5 Hz, 2H), 6.94 (d, J=9.5 Hz, 2H), 7.45 (s, 1H), 8.01 (d, J=8.0 Hz, 2H), 8.18 (s, 1H).

(E)-tert-Butyl-3-(1-(4-methoxyphenylsulfonyl)-2,3-dihydro-1H-pyrrolo[2,3-b]pyridin-5-yl)acrylate (3b)

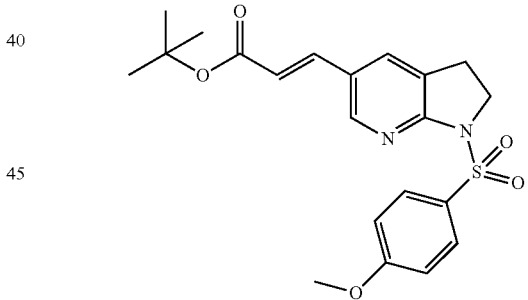

A mixture of 2b (0.15 g, 0.41 mmol), palladium acetate (0.01 g, 0.04 mmol), triphenylphosphine (0.03 g, 0.08 mmol), triethylamine (0.06 mL, 0.41 mmol), sodium bicarbonate (0.07 g, 0.82 mmol), and DMF (1.5 mL) was stirred for 10 minutes, and, after addition of t-butyl acrylate (0.07 mL, 0.49 mmol) at 120° C., and was stirred again overnight. The residue was purified with a flash column over silica gel (ethyl acetate:n-hexane=1:2, Rf=0.25) to afford 3b (0.10 g, 58.56%) as a yellow solid. $^1$H-NMR (500 MHz, CDCl$_3$): δ 1.52 (s, 9H), 3.05 (t, J=8.5 Hz, 2H), 3.84 (s, 3H), 4.08 (t, J=8.5 Hz, 2H), 6.23 (d, J=15.5 Hz, 1H), 6.94 (t, J=9.0 Hz, 2H), 7.46 (d, J=16.0 Hz, 1H), 7.51 (s, 1H), 8.05 (d, J=9.0 Hz, 2H), 8.22 (s, 1H).

51

(E)-3-(1-(4-Methoxyphenylsulfonyl)-2,3-dihydro-1H-pyrrolo[2,3-b]pyridin-5-yl) acrylic acid (4b)

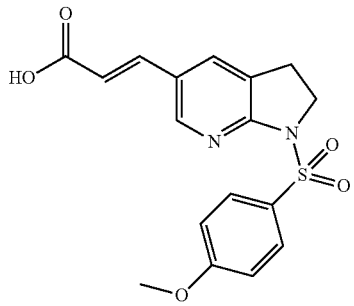 [SMILES: COc1ccc(S(=O)(=O)N2CCc3cc(/C=C/C(=O)O)cnc32)cc1]

To a mixture of 3b (1.26 g, 3.03 mmol) was added trifluoroacetic acid (10.1 mL). It was then stirred at room temperature for 1 hour. Subsequently, water was added to the resultant reaction mixture to precipitate a pale yellow product 4b, which was collected by filtration (0.81 g, 74.18 %). $^1$H-NMR (500 MHz, CD$_3$OD): δ 3.09 (t, J=8.5 Hz, 2H), 3.83 (s, 3H), 4.07 (t, J=8.5 Hz, 2H), 6.42 (d, J=16.0 Hz, 1H), 7.05 (d, J=9.0 Hz, 2H), 7.58 (d, J=16.0 Hz, 1H), 7.86 (s, 1H), 7.97 (d, J=9.0 Hz, 2H), 8.16 (s, 1H).

(E)-N-hydroxy-3-(1-(4-methoxyphenylsulfonyl)-2,3-dihydro-1H-pyrrolo[2,3-b]pyridin-5-yl)acrylamide (5b)

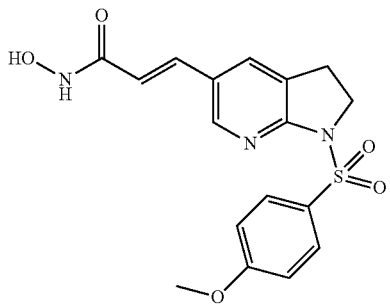

A mixture of 4b (0.80 g, 2.22 mmol), EDC (0.64 g, 3.33 mmol), HOBt (0.36 g, 2.66 mmol), NMM (0.59 mL, 5.33 mmol), and DMF (2 mL) was stirred for 10 minutes, and, after addition of o-(tetrahydro-2H-pyran-2-yl)hydroxylamine (0.31 g, 2.66 mmol), was stirred again at room temperature overnight. Removal of the solvent gave a residue. The residue was purified with a flash column over silica gel (ethyl acetate:n-hexane=2:1, Rf=0.18) to obtain an oily product. Upon addition of MeOH (3.5 mL) and 10% TFA (aq.) (3.5 mL), it was stirred at room temperature for 16 hours. Water was added to precipitate a white product, which was collected by filtration to afford 5b (0.45 g, 88.79%). m.p. 201.6-202.6. $^1$H-NMR (500 MHz, DMSO-d$_6$): δ 3.06 (t, J=8.5 Hz, 2H), 3.80 (s, 3H), 4.01 (t, J=8.5 Hz, 2H), 6.34 (d, J=16.0 Hz, 1H), 7.08 (d, J=9.0 Hz, 2H), 7.38 (d, J=16.0 Hz, 1H), 7.72 (s, 1H), 7.93 (d, J=9.0 Hz, 2H), 8.19 (s, 1H), 8.99 (br, 1H), 10.70 (s, 1H).

52

5-Bromo-1-(3-methoxyphenylsulfonyl)-2,3-dihydro-1H-pyrrolo[2,3-b]pyridine (2c)

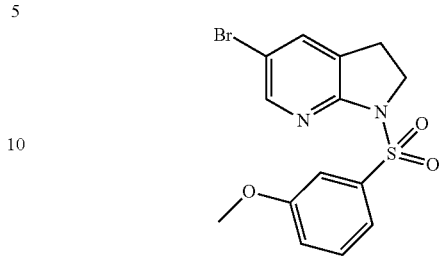

A mixture of 1a (0.35 g, 1.76 mmol), 3-methoxybenzenesulfonyl chloride (0.37 mL, 2.64 mmol), and pyridine (3 mL) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.73) to afford 2c (0.56 g, 86.17%) as a yellow solid. $^1$H-NMR (500 MHz, CDCl$_3$): δ 3.04 (t, J=8.5 Hz, 2H), 3.84 (s, 3H), 4.07 (t, J=8.5 Hz, 2H), 7.11 (dd, J=2.5, 9.0 Hz, 1H), 7.38 (t, J=8.0 Hz, 1H), 7.46 (s, 1H), 7.62 (dd, J=1.5, 8.0 Hz, 1H), 7.65 (s, 1H), 8.19 (s, 1H).

(E)-tert-Butyl-3-(1-(3-methoxyphenylsulfonyl)-2,3-dihydro-1H-pyrrolo[2,3-b]pyridin-5-yl)acrylate (3c)

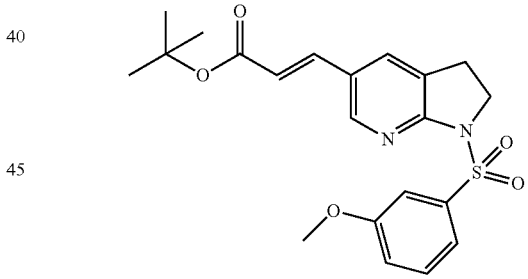

A mixture of 2c (0.56 g, 1.52 mmol), palladium acetate (0.03 g, 0.15 mmol), triphenylphosphine (0.08 g, 0.30 mmol), triethylamine (0.21 ml, 1.52 mmol), sodium bicarbonate (0.26 g, 3.04 mmol), and DMF (2.5 ml) was stirred for 10 minutes. t-Butyl acrylate (0.27 ml, 1.82 mmol) was then added at 120° C. Removal of the solvent after stirring overnight gave a residue, which was purified by a flash column over silica gel (ethyl acetate:n-hexane=1:1, Rf=0.75) to afford 3c (0.61 g, 96.36%) as a yellow solid. $^1$H-NMR (500 MHz, CDCl$_3$): δ 1.52 (s, 9H), 3.06 (t, J=8.5 Hz, 2H), 3.83 (s, 3H), 4.09 (t, J=8.5 Hz, 2H), 6.23 (d, J=16.0 Hz, 1H), 7.10 (d, J=8.0 Hz, 1H), 7.38 (t, J=8.0 Hz, 1H), 7.46 (d, J=16.0 Hz, 1H), 7.53 (s, 1H), 7.64 (d, J=8.0 Hz, 1H), 7.69 (s, 1H), 8.24 (s, 1H).

53

(E)-3-(1-(3-Methoxyphenylsulfonyl)-2,3-dihydro-1H-pyrrolo[2,3-b]pyridin-5-yl) acrylic acid (4c)

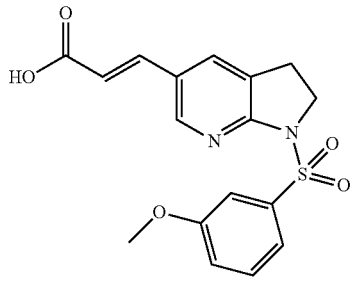 [SMILES: COc1cccc(S(=O)(=O)N2CCc3cc(/C=C/C(=O)O)cnc32)c1]

A mixture of 3c (0.62 g, 1.49 mmol) and trifluoroacetic acid (5.0 ml) was stirred at room temperature for 1 hour. Water was then added to precipitate a white product, which was collected by filtration to afford 4c (0.52 g, 96.84%) as a yellow solid. $^1$H-NMR (500 MHz, CD$_3$OD): δ 3.09 (t, J=8.5 Hz, 2H), 3.82 (s, 3H), 4.08 (t, J=8.5 Hz, 2H), 6.42 (d, J=16.0 Hz, 1H), 7.18 (dd, J=2.0, 8.5 Hz, 1H), 7.44 (t, J=8.5 Hz, 2H), 7.57-7.61 (m, 3H), 7.83 (s, 1H), 8.19 (s, 1H).

(E)-N-hydroxy-3-(1-(3-methoxyphenylsulfonyl)-2,3-dihydro-1H-pyrrolo[2,3-b]pyridin-5-yl)acrylamide (5c)

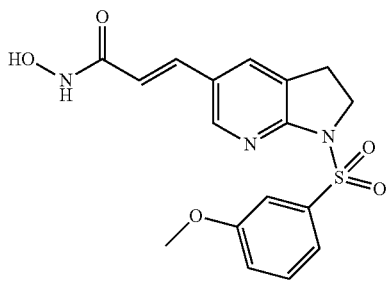 [SMILES: COc1cccc(S(=O)(=O)N2CCc3cc(/C=C/C(=O)NO)cnc32)c1]

A mixture of 4c (0.40 g, 1.11 mmol), EDC (0.32 g, 1.67 mmol), HOBt (0.18 g, 1.33 mmol), NMM (0.29 ml, 2.66 mmol), and DMF (2 ml) was stirred for 10 minutes, and, after addition of o-(tetrahydro-2H-pyran-2-yl)hydroxylamine (0.16 g, 1.34 mmol), was stirred again at room temperature overnight. The residue was purified by a flash column over silica gel (ethyl acetate:n-hexane=2:1, Rf=0.33). An oily product thus obtained was then dissolved in MeOH (3 ml) and 10% TFA (aq.) (3 ml), and stirred at room temperature overnight. To the reaction mixture was added H$_2$O to precipitate a white solid, which was collected by filtration to afford 5c (0.17 g, 40.80%). m.p. 219.1-220.4. $^1$H-NMR (500 MHz, DMSO-d$_6$): δ 3.07 (t, J=8.5 Hz, 2H), 3.79 (s, 3H), 4.03 (t, J=8.5 Hz, 2H), 6.35 (d, J=16.0 Hz, 1H), 7.22-7.24 (m, 1H), 7.37 (d, J=16.0 Hz, 1H), 7.47-7.56 (m, 3H), 7.74 (s, 1H), 8.23 (s, 1H).

54

5-Bromo-1-(3,4-dimethoxyphenylsulfonyl)-2,3-dihydro-1H-pyrrolo[2,3-b]pyridine (2d)

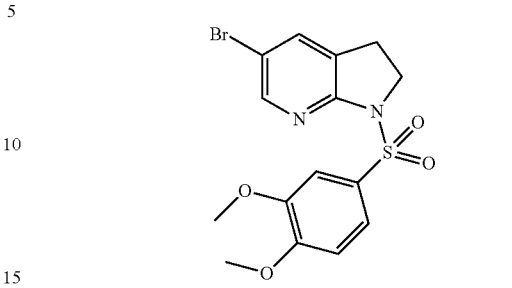

A mixture of 1a (0.35 g, 1.76 mmol), 3,4-dimethoxybenzenesulfonyl chloride (0.62 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.50) to afford 2d (0.59 g, 83.96%) as a yellow solid. $^1$H-NMR (500 MHz, CDCl$_3$): δ 3.03 (t, J=8.5 Hz, 2H), 3.91 (s, 6H), 4.04 (t, J=8.5 Hz, 2H), 6.90 (d, J=8.5 Hz, 1H), 7.46 (s, 1H), 7.64-7.66 (m, 2H), 8.19 (s, 1H).

(E)-tert-Butyl-3-(1-(3,4-dimethoxyphenylsulfonyl)-2,3-dihydro-1H-pyrrolo[2,3-b]pyridin-5-yl)acrylate (3d)

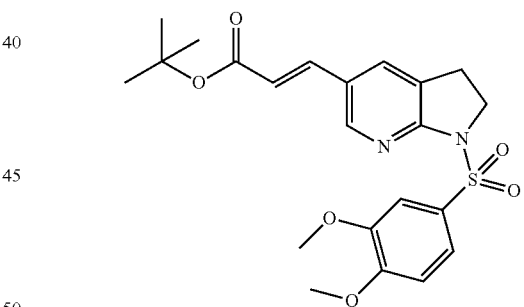

A mixture of 2d (0.59 g, 1.48 mmol), palladium acetate (0.03 g, 0.15 mmol), triphenylphosphine (0.08 g, 0.30 mmol), triethylamine (0.21 ml, 1.48 mmol), sodium bicarbonate (0.25 g, 2.96 mmol), and DMF (2.5 ml) was stirred for 10 minutes, and, after addition of t-butyl acrylate (0.26 ml, 1.78 mmol), and was stirred again at 120° C. overnight. The residue was purified by a flash column over silica gel (ethyl acetate:n-hexane=1:1, Rf=0.43) to afford 3d (0.46 g, 69.61%) as a yellow solid. $^1$H-NMR (500 MHz, CDCl$_3$): δ 1.51 (s, 9H), 3.05 (t, J=8.5 Hz, 2H), 3.90 (s, 6H), 4.06 (t, J=8.5 Hz, 2H), 6.23 (d, J=16.0 Hz, 1H), 6.90 (d, J=8.5 Hz, 1H), 7.46 (d, J=16.0 Hz, 1H), 7.52 (s, 1H), 7.66-7.69 (m, 2H), 8.23 (s, 1H).

55

(E)-3-(1-(3,4-Dimethoxyphenylsulfonyl)-2,3-dihydro-1H-pyrrolo[2,3-b]pyridin-5-yl) acrylic acid (4d)

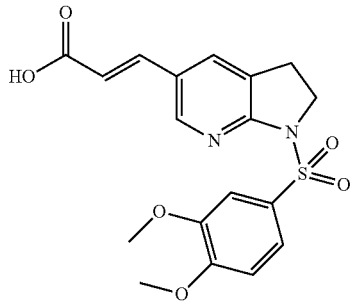 [SMILES: COc1ccc(S(=O)(=O)N2CCc3cc(/C=C/C(=O)O)cnc32)cc1OC]

A mixture of 3d (0.46 g, 1.03 mmol) and trifluoroacetic acid (3.50 ml) was stirred at room temperature for 1 hour. Water was then added to it to precipitate a white solid, which was collected by filtration to afford 4d (0.40 g, 99.47 %). $^1$H-NMR (500 MHz, CD$_3$OD): δ 3.07 (t, J=8.0 Hz, 2H), 3.83 (s, 3H), 3.86 (s, 3H), 4.04 (t, J=8.0 Hz, 2H), 6.42 (d, J=16.0 Hz, 1H), 7.06 (d, J=8.5 Hz, 1H), 7.57-7.62 (m, 3H), 7.82 (s, 1H), 8.19 (s, 1H).

(E)-3-(1-(3,4-Dimethoxyphenylsulfonyl)-2,3-dihydro-1H-pyrrolo[2,3-b]pyridin-5-yl) acrylic acid (5d)

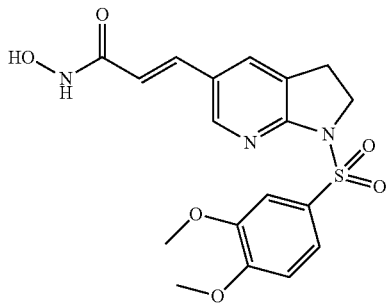 [SMILES: COc1ccc(S(=O)(=O)N2CCc3cc(/C=C/C(=O)NO)cnc32)cc1OC]

A mixture of 4d (0.40 g, 1.02 mmol), EDC (0.29 g, 1.53 mmol), HOBt (0.16 g, 1.22 mmol), NMM (0.27 ml, 2.45 mmol), and DMF (2 ml) was stirred for 10 minutes, and, after addition of o-(tetrahydro-2H-pyran-2-yl)hydroxylamine (0.14 g, 1.22 mmol), was stirred again at room temperature overnight. The residue was purified by a flash column over silica gel (ethyl acetate:n-hexane=2:1, Rf=0.23). An oily product thus obtained was then dissolved in MeOH (5 ml) and 10% TFA (aq.) (5 ml) and then stirred at room temperature overnight. Water was added to the reaction mixture to precipitate a yellow solid, which was collected to afford 5d (0.31 g, 74.96%). m.p. 215.2-216.2. $^1$H-NMR (500 MHz, DMSO-d$_6$): δ 3.04 (t, J=8.0 Hz, 2H), 3.78 (s, 3H), 3.79 (s, 3H), 3.98 (t, J=8.0 Hz, 2H), 6.35 (d, J=15.5 Hz, 1H), 7.11 (d, J=8.5 Hz, 1H), 7.37 (d, J=16.0 Hz, 1H), 7.51 (s, 1H), 7.56 (d, J=8.0 Hz, 1H), 7.73 (s, 1H), 8.23 (s, 1H).

56

5-Bromo-1-(4-fluorophenylsulfonyl)-2,3-dihydro-1H-pyrrolo[2,3-b]pyridine (2e)

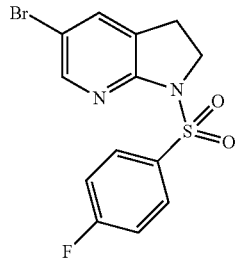 [SMILES: O=S(=O)(c1ccc(F)cc1)N1CCc2cc(Br)cnc21]

A mixture of 1a (0.35 g, 1.76 mmol), 4-fluorobenzenesulfonyl chloride (0.51 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.80) to afford 2e (0.55 g, 87.49%) as a yellow solid. $^1$H-NMR (500 MHz, CDCl$_3$): δ 3.06 (t, J=8.0 Hz, 2H), 4.07 (t, J=8.0 Hz, 2H), 7.15-7.18 (m, 2H), 7.47 (s, 1H), 8.10-8.13 (m, 2H), 8.17 (s, 1H).

(E)-Methyl-3-(1-(4-fluorophenylsulfonyl)-2,3-dihydro-1H-pyrrolo[2,3-b]pyridin-5-yl)acrylate (3e)

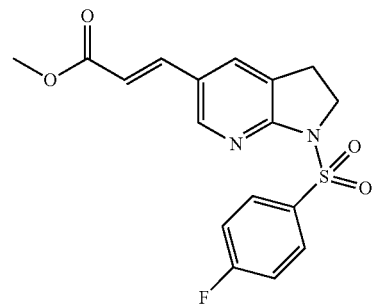 [SMILES: COC(=O)/C=C/c1cnc2c(c1)CCN2S(=O)(=O)c1ccc(F)cc1]

A mixture of 2e (0.38 g, 1.06 mmol), palladium acetate (0.02 g, 0.11 mmol), triphenylphosphine (0.06 g, 0.21 mmol), triethylamine (0.15 ml, 1.06 mmol), sodium bicarbonate (0.18 g, 2.12 mmol), and DMF (2 ml) was stirred for 10 minutes, and, after addition of methyl acrylate (0.11 ml, 1.27 mmol) at 120° C., and stirred again overnight. The residue was purified by a flash column over silica gel (ethyl acetate:n-hexane=1:1, Rf=0.60) to afford 3e (0.31 g, 80.70%) as a yellow solid. $^1$H-NMR (500 MHz, CDCl$_3$): δ 3.07 (t, J=8.5 Hz, 2H), 3.80 (s, 3H), 4.11 (t, J=8.5 Hz, 2H), 6.31 (d, J=16.0 Hz, 1H), 7.15-7.19 (m, 2H), 7.55 (s, 1H), 7.58 (d, J=16.0 Hz, 1H), 8.14-8.17 (m, 2H), 8.23 (s, 1H).

(E)-3-(1-(4-Fluorophenylsulfonyl)-2,3-dihydro-1H-pyrrolo[2,3-b]pyridin-5-yl) acrylic acid (4e)

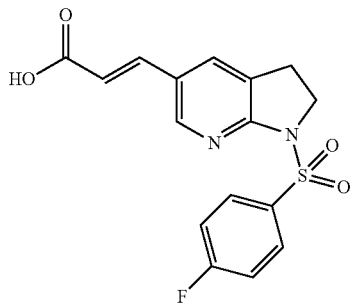

A mixture of 4e (0.31 g, 0.86 mmol), dioxane (5 ml), and 1 M LiOH (aq.) (1.72 ml, 1.72 mmol) was stirred overnight at 40° C. After the solvent was removed, the resultant residue was dissolved in water. 3 N HCl (aq.) was added to precipitate a white product, which was collected by filtration to afford 5e (0.20 g, 66.76%). $^1$H-NMR (500 MHz, DMSO-$d_6$): δ 3.08 (t, J=8.5 Hz, 2H), 4.08 (t, J=8.5 Hz, 2H), 6.45 (d, J=16.0 Hz, 1H), 7.41-7.45 (m, 2H), 7.51 (d, J=16.0 Hz, 1H), 7.95 (s, 1H), 8.07-8.10 (m, 2H), 8.26 (s, 1H).

(E)-3-(1-(4-Fluorophenylsulfonyl)-2,3-dihydro-1H-pyrrolo[2,3-b]pyridin-5-yl)-N-hydroxyacrylamide (5e)

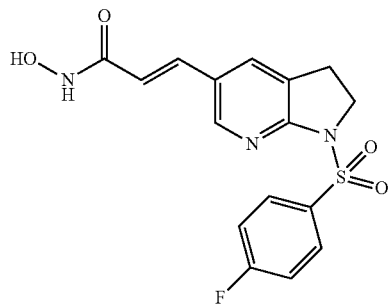

A mixture of 4e (0.40 g, 1.15 mmol), EDC (0.33 g, 1.73 mmol), HOBt (0.19 g, 1.38 mmol), NMM (0.30 ml, 2.76 mmol), and DMF (2 ml) was stirred for 10 minutes, and, after addition of o-(tetrahydro-2H-pyran-2-yl)hydroxylamine (0.16 g, 1.38 mmol), was stirred again at room temperature overnight. The residue resulting from removal of the solvent was purified by a flash column over silica gel (ethyl acetate:n-hexane=2:1, Rf=0.25). An oily product thus obtained was then dissolved in MeOH (5 ml) and 10% TFA (aq.) (5 ml), and stirred at room temperature overnight. Water was added to precipitate a pale yellow solid, which was collected by filtration to afford 5e (0.22 g, 52.65%). m.p. 209.7-210.9. $^1$H-NMR (500 MHz, CD$_3$OD): δ 3.09 (t, J=8.5 Hz, 2H), 4.09 (t, J=8.5 Hz, 2H), 6.38 (d, J=16.0 Hz, 1H), 7.26-7.30 (m, 2H), 7.47 (d, J=16.0 Hz, 1H), 7.73 (s, 1H), 8.10-8.13 (m, 2H), 8.16 (s, 1H).

5-Bromo-1-(3-fluorophenylsulfonyl)-2,3-dihydro-1H-pyrrolo[2,3-b]pyridine (2f)

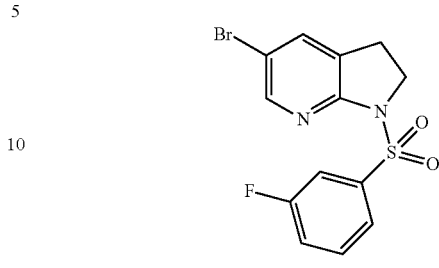

A mixture of 1a (0.35 g, 1.76 mmol), 3-fluorobenzenesulfonyl chloride (0.35 ml, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:4, Rf=0.25) to afford 2f (0.79 g, 62.83%) as a yellow solid. $^1$H-NMR (500 MHz, CDCl$_3$): δ 3.087 (t, J=8.5 Hz, 2H), 4.09 (t, J=8.5 Hz, 2H), 7.27-7.30 (m, 1H), 7.46-7.50 (m, 2H), 7.82-7.84 (m, 1H), 7.87-7.89 (m, 1H), 8.19 (s, 1H).

(E)-Methyl-3-(1-(3-fluorophenylsulfonyl)-2,3-dihydro-1H-pyrrolo[2,3-b]pyridin-5-yl)acrylate (3f)

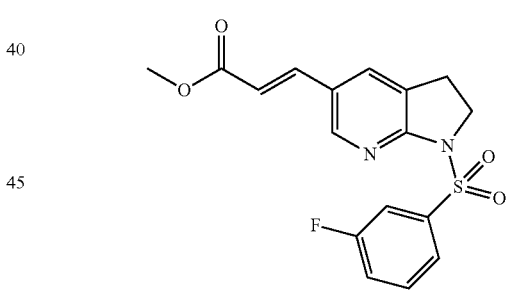

A mixture of 2f (0.15 g, 0.42 mmol), Pd$_2$(dba)$_3$ (0.04 g, 0.04 mmol), [(t-Bu)$_3$PH]BF$_4$ (0.02 g, 0.08 mmol), triethylamine (0.06 ml, 0.42 mmol), sodium bicarbonate (0.07 g, 0.84 mmol), and DMF (1.5 ml) was stirred for 10 minutes, and, after addition of methyl acrylate (0.04 ml, 0.50 mmol) at 120° C., was stirred again overnight. The residue resulting from removal of the solvent was purified by a flash column over silica gel (ethyl acetate:n-hexane=1:2, Rf=0.25) to afford 3f (0.12 g, 78.84%) as a yellow solid. $^1$H-NMR (500 MHz, CDCl$_3$): δ 3.10 (t, J=8.5 Hz, 2H), 3.79 (s, 3H), 4.11 (t, J=8.5 Hz, 2H), 6.31 (d, J=16.0 Hz, 1H), 7.28-7.30 (m, 1H), 7.46-7.50 (m, 1H), 7.58 (d, J=16.5 Hz, 2H), 7.85-7.87 (m, 1H), 7.91 (d, J=8.0 Hz, 1H), 8.25 (s, 1H).

(E)-3-(1-(3-Fluorophenylsulfonyl)-2,3-dihydro-1H-pyrrolo[2,3-b]pyridin-5-yl) acrylic acid (4f)

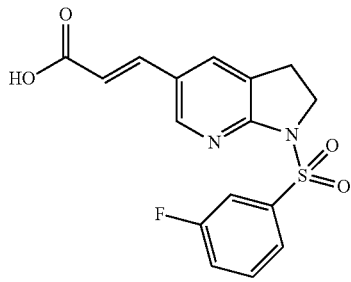 [SMILES: O=C(O)/C=C/c1cnc2c(c1)CCN2S(=O)(=O)c1cccc(F)c1]

A mixture of 3f (0.34 g, 0.94 mmol), dioxane (10 ml), and 1 M LiOH (aq.) (1.88 ml, 1.88 mmol) was stirred overnight at 40° C. After the solvent was removed, the resultant residue was dissolved in water. 3N HCl (aq.) was added to precipitate a white product, which was collected by filtration to afford 4f (0.25 g, 76.35%). $^1$H-NMR (500 MHz, DMSO-$d_6$): δ 3.09 (t, J=8.5 Hz, 2H), 4.11 (t, J=8.5 Hz, 2H), 6.46 (d, J=16.0 Hz, 1H), 7.50 (d, J=16.0 Hz, 1H), 7.54-7.58 (m, 1H), 7.63-7.67 (m, 1H), 7.82 (d, J=8.5 Hz, 1H), 7.86 (d, J=8.0 Hz, 1H), 7.97 (s, 1H), 8.28 (s, 1H).

(E)-3-(1-(3-Fluorophenylsulfonyl)-2,3-dihydro-1H-pyrrolo[2,3-b]pyridin-5-yl)-N-hydroxyacrylamide (5f)

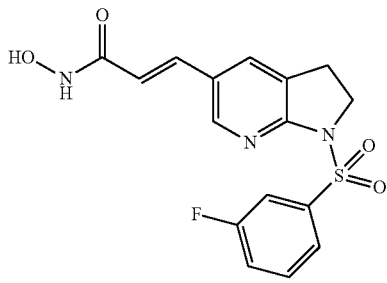 [SMILES: O=C(/C=C/c1cnc2c(c1)CCN2S(=O)(=O)c1cccc(F)c1)NO]

A mixture of 4f (0.25 g, 0.72 mmol), EDC (0.21 g, 1.08 mmol), HOBt (0.12 g, 0.86 mmol), NMM (0.19 ml, 1.73 mmol), and DMF (2 ml) was stirred for 10 minutes, and, after addition of o-(tetrahydro-2H-pyran-2-yl)hydroxylamine (0.10 g, 0.86 mmol) at room temperature, was stirred again overnight. The residue resulting from removal of the solvent was purified by a flash column over silica gel (ethyl acetate:n-hexane=2:1, Rf=0.38). An oily product thus obtained was then dissolved in MeOH (3 ml) and 10% TFA (aq.) (3 ml), and stirred at room temperature overnight. Water was added to precipitate a white solid, which was collected by filtration to afford 5f (0.15 g, 57.34%). m.p. 207.1-208.0. $^1$H-NMR (500 MHz, DMSO-$d_6$): δ 3.10 (t, J=8.5 Hz, 2H), 4.10 (t, J=8.5 Hz, 2H), 6.36 (d, J=16.0 Hz, 1H), 7.36 (d, J=16.0 Hz, 1H), 7.56 (td, J=2.5, 8.5 Hz, 1H), 7.63-7.68 (m, 1H), 7.77 (s, 1H), 7.82 (d, J=8.5 Hz, 1H), 7.86 (d, J=8.0 Hz, 1H), 8.22 (s, 1H), 10.73 (br, 1H).

5-Bromo-1-(4-chlorophenylsulfonyl)-2,3-dihydro-1H-pyrrolo[2,3-b]pyridine (2g)

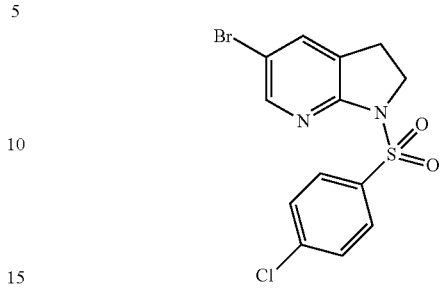

A mixture of 1a (0.35 g, 1.76 mmol), 4-chlorobenzenesulfonyl chloride (0.56 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.78) to afford 2g (0.55 g, 83.63%) as a yellow solid. $^1$H-NMR (500 MHz, CDCl$_3$): δ 3.06 (t, J=8.5 Hz, 2H), 4.08 (t, J=8.5 Hz, 2H), 7.46-7.47 (m, 3H), 8.03 (d, J=9.0 Hz, 2H), 8.17 (s, 1H).

(E)-Methyl-3-(1-(4-chlorophenylsulfonyl)-2,3-dihydro-1H-pyrrolo[2,3-b]pyridine-5-yl)acrylate (3g)

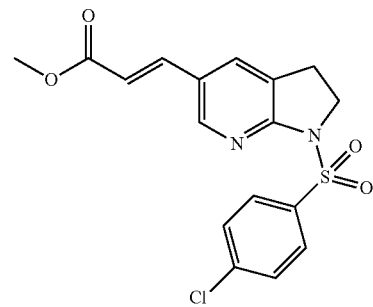 [SMILES: COC(=O)/C=C/c1cnc2c(c1)CCN2S(=O)(=O)c1ccc(Cl)cc1]

A mixture of 2g (0.40 g, 1.07 mmol), palladium acetate (0.02 g, 0.11 mmol), triphenylphosphine (0.06 g, 0.21 mmol), triethylamine (0.15 ml, 1.07 mmol), sodium bicarbonate (0.18 g, 2.14 mmol), and DMF (2 ml) was stirred for 10 minutes, and, after addition of methyl acrylate (0.11 ml, 1.28 mmol) at 120° C., was stirred again overnight. The residue resulting from removal of the solvent was purified with a flash column over silica gel (ethyl acetate:n-hexane=1:3, Rf=0.28) to afford 3g (0.37 g, 91.28%) as a yellow solid. $^1$H-NMR (500 MHz, CDCl$_3$): δ 3.10 (t, J=8.5 Hz, 2H), 3.80 (s, 3H), 4.11 (t, J=8.5 Hz, 2H), 6.31 (d, J=16.0 Hz, 1H), 7.47 (d, J=8.5 Hz, 1H), 7.56 (s, 1H), 7.58 (d, J=16.0 Hz, 1H), 8.07 (d, J=8.5 Hz, 2H), 8.23 (s, 1H).

(E)-3-(1-(4-Chlorophenylsulfonyl)-2,3-dihydro-1H-pyrrolo[2,3-b]pyridin-5-yl) acrylic acid (4g)

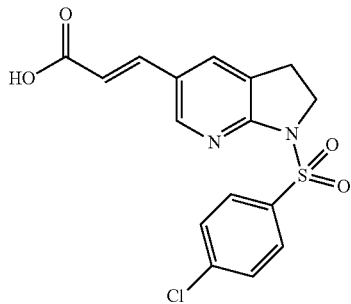 [SMILES: O=C(O)/C=C/c1cnc2c(c1)CCN2S(=O)(=O)c1ccc(Cl)cc1]

A mixture of 3g (0.37 g, 0.98 mmol), dioxane (5 ml), and 1M LiOH (aq.) (1.96 ml, 1.96 mmol) was stirred overnight at 40° C. After the solvent was removed, the resultant residue was dissolved in water. 3N HCl (aq.) was added to precipitate a white solid, which was collected by filtration to afford 4g (0.18 g, 50.35%). $^1$H-NMR (500 MHz, CD$_3$OD): δ 3.11 (t, J=8.5 Hz, 2H), 4.11 (t, J=8.5 Hz, 2H), 6.42 (d, J=16.0 Hz, 1H), 7.56-7.60 (m, 3H), 7.84 (s, 1H), 8.03 (d, J=8.5 Hz, 2H), 8.17 (s, 1H).

(E)-3-(1-(4-Chlorophenylsulfonyl)-2,3-dihydro-1H-pyrrolo[2,3-b]pyridin-5-yl)-N-hydroxyacrylamide (5g)

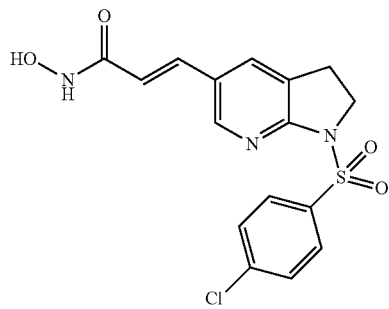 [SMILES: O=C(/C=C/c1cnc2c(c1)CCN2S(=O)(=O)c1ccc(Cl)cc1)NO]

A mixture of 4g (0.30 g, 0.82 mmol), EDC (0.24 g, 1.23 mmol), HOBt (0.13 g, 0.98 mmol), NMM (0.22 ml, 1.97 mmol), and DMF (2 ml) was stirred for 10 minutes, and, after addition of o-(tetrahydro-2H-pyran-2-yl)hydroxylamine (0.11 g, 0.98 mmol) at room temperature, was stirred again overnight. The residue resulting from removal of the solvent was purified with a flash column over silica gel (ethyl acetate:n-hexane=2:1, Rf=0.20). An oily product thus obtained was then dissolved in MeOH (3 ml) and 10% TFA (aq.) (3 ml), and stirred at room temperature overnight. Water was added to precipitate a pale yellow product, which was collected by filtration to afford 5g (0.20 g, 64.22%). m.p. 207.6-208.7. $^1$H-NMR (500 MHz, DMSO-d$_6$): δ 3.09 (t, J=8.5 Hz, 2H), 4.07 (t, J=8.5 Hz, 2H), 6.36 (d, J=16.0 Hz, 1H), 7.38 (d, J=16.0 Hz, 1H), 7.66 (d, J=8.5 Hz, 2H), 7.76 (s, 1H), 8.01 (d, J=8.5 Hz, 2H), 8.19 (s, 1H), 9.01 (br, 1H), 10.72 (s, 1H).

5-Bromo-1-(3-chlorophenylsulfonyl)-2,3-dihydro-1H-pyrrolo[2,3-b]pyridine (2h)

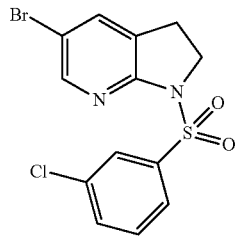 [SMILES: O=S(=O)(c1cccc(Cl)c1)N1CCc2cc(Br)cnc21]

A mixture of 1a (0.35 g, 1.76 mmol), 3-chlorobenzenesulfonyl chloride (0.37 ml, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:2, Rf=0.55) to afford 2h (0.50 g, 76.03%) as a yellow solid. $^1$H-NMR (500 MHz, CDCl$_3$): δ3.08 (t, J=8.5 Hz, 2H), 4.09 (t, J=8.5 Hz, 2H), 7.44 (t, J=8.0 Hz, 1H), 7.49 (s, 1H), 7.55 (d, J=7.5 Hz, 1H), 7.99 (d, J=8.0 Hz, 1H), 8.10 (s, 1H), 8.19 (s, 1H).

(E)-Methyl-3-(1-(3-chlorophenylsulfonyl)-2,3-dihydro-1H-pyrrolo[2,3-b]pyridin-5-yl)acrylate (3h)

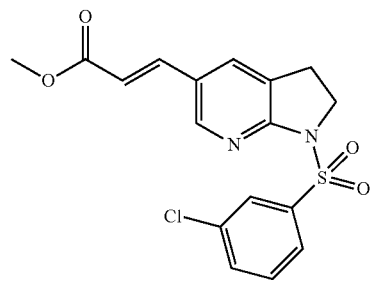 [SMILES: COC(=O)/C=C/c1cnc2c(c1)CCN2S(=O)(=O)c1cccc(Cl)c1]

A mixture of 2h (0.15 g, 0.40 mmol), Pd$_2$(dba)$_3$ (0.04 g, 0.04 mmol), [(t-Bu)$_3$PH]BF$_4$ (0.02 g, 0.08 mmol), triethylamine (0.06 ml, 0.40 mmol), sodium bicarbonate (0.07 g, 0.80 mmol), and DMF (1.5 ml) was stirred for 10 minutes, and, after addition of methyl acrylate (0.04 ml, 0.44 mmol) at 120° C., was stirred again overnight. The residue resulting from removal of the solvent was purified with a flash column over silica gel (ethyl acetate:n-hexane=1:2, Rf=0.20) to afford 3h (0.13 g, 85.79%) as a yellow solid. $^1$H-NMR (500 MHz, CDCl$_3$): δ 3.11 (t, J=8.5 Hz, 2H), 3.79 (s, 3H), 4.13 (t, J=8.5 Hz, 2H), 6.31 (d, J=16.0 Hz, 1H), 7.44 (t, J=8.0 Hz, 1H), 7.54-7.60 (m, 3H), 8.03 (t, J=8.0 Hz, 1H), 8.13 (s, 1H), 8.25 (s, 1H).

(E)-3-(1-(3-Chlorophenylsulfonyl)-2,3-dihydro-1H-pyrrolo[2,3-b]pyridin-5-yl) acrylic acid (4h)

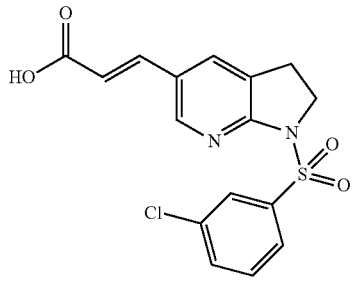

A mixture of 3h (0.36 g, 0.95 mmol), dioxane (10 ml), and 1M LiOH (aq.) (1.90 ml, 1.90 mmol) was stirred overnight at 40° C. After the solvent was removed, the resultant residue was dissolved in water. 3N HCl (aq.) was added to precipitate a white product, which was collected by filtration to afford 4h (0.31 g, 89.45%). $^1$H-NMR (500 MHz, DMSO-$d_6$): δ 3.09 (t, J=8.5 Hz, 2H), 4.11 (t, J=8.5 Hz, 2H), 6.46 (d, J=15.5 Hz, 1H), 7.51 (d, J=16.0 Hz, 1H), 7.63 (t, J=8.0 Hz, 1H), 7.77 (d, J=8.0 Hz, 1H), 7.97-7.98 (m, 2H), 8.02 (s, 1H), 8.28 (s, 1H).

(E)-3-(1-(3-Chlorophenylsulfonyl)-2,3-dihydro-1H-pyrrolo[2,3-b]pyridin-5-yl)-N-hydroxyacrylamide (5h)

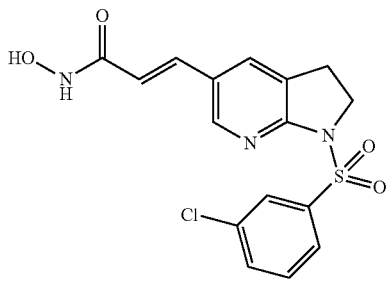 [SMILES: O=C(/C=C/c1cnc2c(c1)CCN2S(=O)(=O)c1cccc(Cl)c1)NO]

A mixture of 4h (0.31 g, 0.85 mmol), EDC (0.25 g, 1.28 mmol), HOBt (0.14 g, 1.02 mmol), NMM (0.22 ml, 2.04 mmol), and DMF (2 ml) was stirred for 10 minutes, and, after addition of o-(tetrahydro-2H-pyran-2-yl)hydroxylamine (0.29 g, 2.45 mmol) at room temperature, was stirred again overnight. The residue resulting from removal of the solvent was purified with a flash column over silica gel (ethyl acetate:n-hexane=2:1, Rf=0.20). An oily product thus obtained was dissolved in MeOH (4 ml) and 10% TFA (aq.) (4 ml) at room temperature, was stirred again overnight. Water was added to precipitate a white product, which was collected by filtration to afford 5h (0.23 g, 71.24%). m.p. 214.9-216.2. $^1$H-NMR (500 MHz, DMSO-$d_6$): δ 3.10 (t, J=8.5 Hz, 2H), 4.10 (t, J=8.5 Hz, 2H), 6.36 (d, J=16.0 Hz, 1H), 7.37 (d, J=15.5 Hz, 1H), 7.63 (t, J=8.0 Hz, 1H), 7.75-7.77 (m, 2H), 7.97 (d, J=8.0 Hz, 1H), 8.03 (s, 1H), 8.22 (s, 1H).

5-Bromo-1-(4-nitrophenylsulfonyl)-2,3-dihydro-1H-pyrrolo[2,3-b]pyridine (2i)

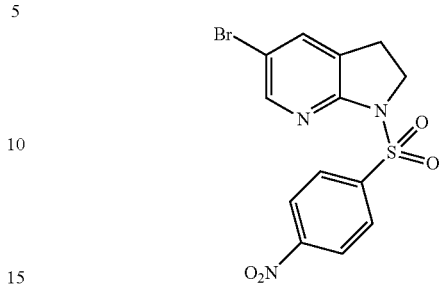

A mixture of 1 (0.35 g, 1.76 mmol), 4-nitrobenzenesulfonyl chloride (0.59 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.73) to afford 2i (0.35 g, 51.76%) as a yellow solid. $^1$H-NMR (500 MHz, CDCl$_3$): δ 3.10 (t, J=8.5 Hz, 2H), 4.13 (t, J=8.5 Hz, 2H), 7.51 (s, 1H), 8.29-8.34 (m, 4H).

(E)-tert-Butyl-3-(1-(4-nitrophenylsulfonyl)-2,3-dihydro-1H-pyrrolo[2,3-b]-pyridin-5-yl)acrylate (3i)

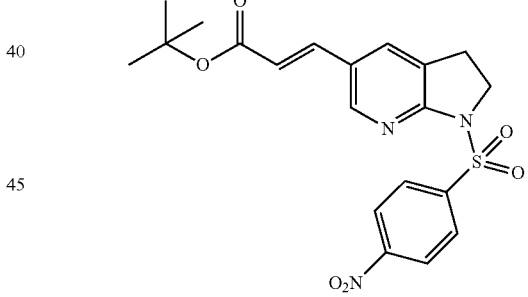

A mixture of 2i (0.35 g, 0.91 mmol), palladium acetate (0.02 g, 0.09 mmol), triphenylphosphine (0.05 g, 0.18 mmol), triethylamine (0.13 ml, 0.91 mmol), sodium bicarbonate (0.15 g, 1.82 mmol), and DMF (2 ml) was stirred for 10 minutes, and, after addition of t-butyl acrylate (0.16 ml, 1.09 mmol) at 120° C., was stirred again overnight. The residue resulting from removal of the solvent was purified with a flash column over silica gel (ethyl acetate:n-hexane=1:2, Rf=0.28) to afford 3i (0.13 g, 32.11%) as a yellow solid. $^1$H-NMR (500 MHz, CDCl$_3$): δ 1.52 (s, 9H), 3.13 (t, J=8.5 Hz, 2H), 4.16 (t, J=8.5 Hz, 2H), 6.25 (d, J=16.0 Hz, 1H), 7.46 (t, J=16.0 Hz, 1H), 7.56 (s, 1H), 8.22 (s, 1H), 8.34 (s, 4H).

65

(E)-3-(1-(4-Nitrophenylsulfonyl)-2,3-dihydro-1H-pyrrolo[2,3-b]pyridin-5-yl)-acrylic acid (4i)

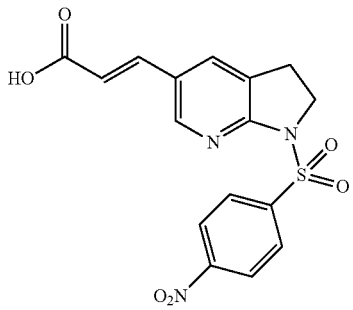 [SMILES: O=C(O)/C=C/c1cnc2c(c1)CCN2S(=O)(=O)c1ccc([N+](=O)[O-])cc1]

A mixture of 3i (0.13 g, 0.31 mmol) and trifluoroacetic acid (1.03 ml) and stirred at room temperature for 2 hours. The reaction mixture was added water to precipitate a yellow product, which was collected by filtration to afford 4i (0.06 g, 51.56%). $^1$H-NMR (500 MHz, CD$_3$OD): δ 3.16 (t, J=8.5 Hz, 2H), 4.19 (t, J=8.5 Hz, 2H), 6.44 (d, J=15.5 Hz, 1H), 7.59 (d, J=16.0 Hz, 1H), 7.87 (s, 1H), 8.22 (s, 1H), 8.34 (t, J=9.0 Hz, 2H), 8.41 (d, J=9.0 Hz, 2H).

(E)-N-hydroxy-3-(1-(4-nitrophenylsulfonyl)-2,3-dihydro-1H-pyrrolo[2,3-b]pyridin-5-yl)acrylamide (5i)

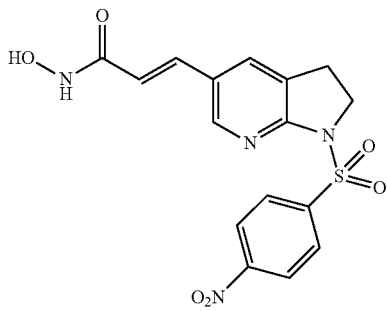 [SMILES: O=C(/C=C/c1cnc2c(c1)CCN2S(=O)(=O)c1ccc([N+](=O)[O-])cc1)NO]

A mixture of 4i (0.30 g, 0.80 mmol), EDC (0.23 g, 1.20 mmol), HOBt (0.13 g, 0.96 mmol), NMM (0.21 ml, 1.92 mmol), and DMF (2 ml) was stirred for 10 minutes, and, after addition of o-(tetrahydro-2H-pyran-2-yl)hydroxylamine (0.11 g, 0.96 mmol) at room temperature, was stirred again overnight. The residue resulting from removal of the solvent was purified with a flash column over silica gel (ethyl acetate:n-hexane=2:1, Rf=0.23). An oily product thus obtained was then dissolved in MeOH (3 ml) and 10% TFA (aq.) (3 ml), and stirred at room temperature overnight. Water was added to precipitate a yellow solid, which was collected by filtration to afford 5i (0.14 g, 44.83%). m.p. 200.4-201.5. $^1$H-NMR (500 MHz, CD$_3$OD+DMSO-d$_6$): δ 3.14 (t, J=8.5 Hz, 2H), 4.18 (t, J=8.5 Hz, 2H), 6.40 (d, J=16.0 Hz, 1H), 7.47 (d, J=16.0 Hz, 1H), 7.76 (s, 1H), 8.19 (s, 1H), 8.33 (t, J=9.0 Hz, 2H), 8.40 (d, J=9.0 Hz, 2H).

66

5-Bromo-1-(3-nitrophenylsulfonyl)-2,3-dihydro-1H-pyrrolo[2,3-b]pyridine (2j)

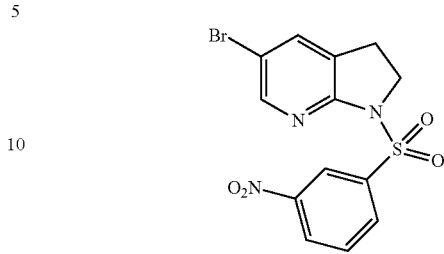

A mixture of 1a (0.35 g, 1.76 mmol), 3-nitrobenzenesulfonyl chloride (0.59 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.50) to afford 2j (0.36 g, 53.24%) as a yellow solid. $^1$H-NMR (500 MHz, CDCl$_3$): δ 3.11 (t, J=8.5 Hz, 2H), 4.16 (t, J=8.5 Hz, 2H), 7.51 (s, 1H), 7.72 (t, J=9.0 Hz, 1H), 8.18 (s, 1H), 8.42-8.44 (m, 1H), 8.46-8.49 (m, 1H), 8.96 (t, J=9.0 Hz, 1H).

(E)-tert-Butyl-3-(1-(3-nitrophenylsulfonyl)-2,3-dihydro-1H-pyrrolo[2,3-b]pyridin-5-yl)acrylate (3j)

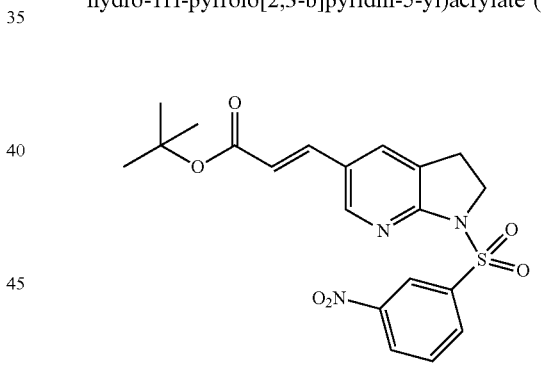

A mixture of 2j (0.36 g, 1.76 mmol), palladium acetate (0.02 g, 0.09 mmol), triphenylphosphine (0.05, 0.19 mmol), triethylamine (0.13 ml, 0.94 mmol), sodium bicarbonate (0.16 g, 1.88 mmol), and DMF (2 ml) was stirred for 10 minutes, and, after addition of t-butyl acrylate (0.16 ml, 1.13 mmol) at 120° C., was stirred again overnight. The residue resulting from removal of the solvent was purified with a flash column over silica gel (ethyl acetate:n-hexane=1:2, Rf=0.20) to afford 3j (0.30 g, 73.99%) as a yellow solid. $^1$H-NMR (500 MHz, CDCl$_3$): δ 1.52 (s, 9H), 3.14 (t, J=8.5 Hz, 2H), 4.18 (t, J=8.5 Hz, 2H), 6.25 (d, J=16.0 Hz, 1H), 7.46 (d, J=16.0 Hz, 1H), 7.56 (s, 1H), 7.72 (t, J=8.0 Hz, 1H), 8.23 (s, 1H), 8.42-8.44 (m, 1H), 8.50-8.52 (m, 1H), 9.00 (t, J=9.0 Hz, 1H).

(E)-3-(1-(3-Nitrophenylsulfonyl)-2,3-dihydro-1H-pyrrolo[2,3-b]pyridin-5-yl)acrylic acid (4j)

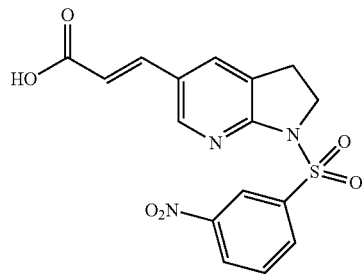 [SMILES: O=C(O)/C=C/c1cnc2c(c1)CCN2S(=O)(=O)c1cccc([N+](=O)[O-])c1]

A mixture of 3j (0.30 g, 0.70 mmol) and trifluoroacetic acid (2.33 ml) was stirred at room temperature for 2 hours. The reaction mixture was added water to precipitate a yellow product, which was collected by filtration to afford 4j (0.16 g, 60.89%). $^1$H-NMR (500 MHz, DMSO-$d_6$): δ 3.10 (t, J=8.5 Hz, 2H), 4.15 (t, J=8.5 Hz, 2H), 6.46 (d, J=16.0 Hz, 1H), 7.51 (d, J=16.0 Hz, 1H), 7.90 (t, J=8.0 Hz, 1H), 7.97 (s, 1H), 8.29 (s, 1H), 8.44 (d, J=8.0 Hz, 1H), 8.50 (d, J=8.0 Hz, 1H), 8.74 (s, 1H).

(E)-N-hydroxy-3-(1-(3-nitrophenylsulfonyl)-2,3-dihydro-1H-pyrrolo[2,3-b]pyridin-5-yl)acrylamide (5j)

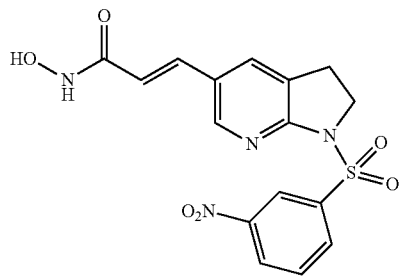 [SMILES: O=C(/C=C/c1cnc2c(c1)CCN2S(=O)(=O)c1cccc([N+](=O)[O-])c1)NO]

A mixture of 4j (0.27 g, 0.72 mmol), EDC (0.21 g, 1.08 mmol), HOBt (0.12 g, 0.86 mmol), NMM (0.19 ml, 1.73 mmol), and DMF (2 ml) was stirred for 10 minutes, and, after addition of o-(tetrahydro-2H-pyran-2-yl)hydroxylamine (0.10 g, 0.86 mmol) at room temperature, was stirred again overnight. The residue resulting from removal of the solvent was purified with a flash column over silica gel (ethyl acetate:n-hexane=2:1, Rf=0.20). An oily product thus obtained was dissolved in MeOH (5 ml) and 10% TFA (aq.) (5 ml) at room temperature, and was stirred overnight. Water was added to precipitate a yellow solid, which was collected by filtration to afford 5j (0.20 g, 71.16%). m.p. 158.8-160.3. $^1$H-NMR (500 MHz, CD$_3$OD+DMSO-$d_6$): δ 3.14 (t, J=8.5 Hz, 2H), 4.17 (t, J=8.5 Hz, 2H), 6.39 (d, J=16.0 Hz, 1H), 7.47 (d, J=15.5 Hz, 1H), 7.75 (s, 1H), 7.84 (t, J=8.0 Hz, 1H), 8.20 (s, 1H), 8.46 (d, J=8.0 Hz, 1H), 8.48-8.50 (m, 1H), 8.90 (t, J=9.0 Hz, 1H).

5-Bromo-1-(4-bromophenylsulfonyl)-2,3-dihydro-1H-pyrrolo[2,3-b]pyridine (2k)

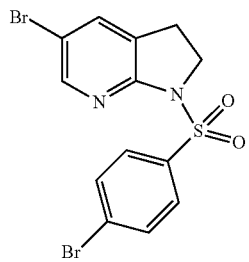 [SMILES: O=S(=O)(c1ccc(Br)cc1)N1CCc2cc(Br)cnc21]

A mixture of 1a (0.35 g, 1.76 mmol), 4-bromobenzenesulfonyl chloride (0.67 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.80) to afford 2k (0.57 g, 77.46%) as a yellow solid. $^1$H-NMR (500 MHz, CDCl$_3$): δ 3.05 (t, J=8.5 Hz, 2H), 4.06 (t, J=8.5 Hz, 2H), 7.47 (s, 1H), 7.62 (d, J=8.5 Hz, 2H), 7.95 (d, J=8.5 Hz, 2H), 8.16 (s, 1H).

(E)-tert-butyl-4-(4-(5-((E)-3-tert-butoxy-3-oxoprop-1-enyl)-2,3-dihydro-1H-pyrrolo[2,3-b]pyridin-1-ylsulfonyl)phenyl)but-2-enoate (3k)

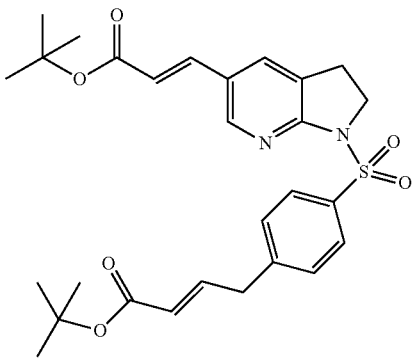 [SMILES: CC(C)(C)OC(=O)/C=C/Cc1ccc(S(=O)(=O)N2CCc3cc(/C=C/C(=O)OC(C)(C)C)cnc32)cc1]

A mixture of 2k (0.57 g, 1.36 mmol), palladium acetate (0.06 g, 0.27 mmol), triphenylphosphine (0.14 g, 0.54 mmol), triethylamine (0.38 ml, 2.72 mmol), sodium bicarbonate (0.46 g, 5.44 mmol), and DMF (3 ml) was stirred for 10 minutes, and, after addition of t-butyl acrylate (0.47 ml, 3.26 mmol) at 120° C., was stirred again overnight. The residue resulting from removal of the solvent was purified with a flash column over silica gel (ethyl acetate:n-hexane=1:2, Rf=0.25) to afford 3k (0.56 g, 80.33%) as a yellow solid. $^1$H-NMR (500 MHz, CDCl$_3$): δ 1.52 (s, 18H), 3.08 (t, J=8.5 Hz, 2H), 4.12 (t, J=8.5 Hz, 2H), 6.23 (d, J=16.0 Hz, 1H), 6.43 (d, J=15.5 Hz, 1H), 7.46 (d, J=16.0 Hz, 1H), 7.52-7.55 (m, 2H), 7.59 (d, J=8.5 Hz, 2H), 8.12 (d, J=8.5 Hz, 2H), 8.22 (s, 1H).

(E)-4-(4-(5-((E)-2-carboxyvinyl)-2,3-dihydro-1H-pyrrolo[2,3-b]pyridin-1-ylsulfonyl)-phenyl)but-2-enoic acid (4k)

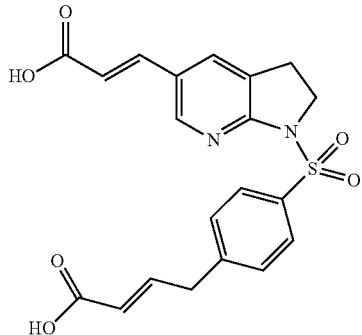 [SMILES: O=C(O)/C=C/Cc1ccc(S(=O)(=O)N2CCc3cc(/C=C/C(=O)O)cnc32)cc1]

A mixture of 3k (0.56 g, 1.09 mmol) and trifluoroacetic acid (5.50 ml) was stirred at room temperature for 2 hours. The reaction mixture was added water to precipitate a white product, which was collected by filtration to afford 4k (0.23 g, 52.70%). $^1$H-NMR (500 MHz, DMSO-$d_6$): δ 3.09 (t, J=8.5 Hz, 2H), 4.10 (t, J=8.5 Hz, 2H), 6.45 (d, J=16.0 Hz, 1H), 6.65 (d, J=16.0 Hz, 1H), 7.50 (d, J=16.0 Hz, 1H), 7.59 (d, J=16.5 Hz, 1H), 7.88 (d, J=8.5 Hz, 2H), 7.95 (s, 1H), 8.01 (d, J=8.0 Hz, 2H), 8.27 (s, 1H).

(E)-N-hydroxy-4-(4-(5-((E)-3-(hydroxyamino)-3-oxoprop-1-enyl)-2,3-dihydro-1H-pyrrolo[2,3-b]pyridin-1-ylsulfonyl)phenyl)but-2-enamide (5k)

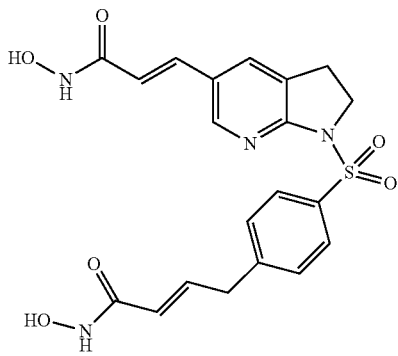 [SMILES: O=C(/C=C/Cc1ccc(S(=O)(=O)N2CCc3cc(/C=C/C(=O)NO)cnc32)cc1)NO]

A mixture of 4k (0.30 g, 0.75 mmol), EDC (0.43 g, 2.25 mmol), HOBt (0.24 g, 1.80 mmol), NMM (0.46 ml, 3.60 mmol), and DMF (2 ml) was stirred for 10 minutes, and, after addition of o-(tetrahydro-2H-pyran-2-yl)hydroxylamine (0.21 g, 1.80 mmol) at room temperature, was stirred again overnight. The residue resulting from removal of the solvent was purified with a flash column over silica gel (ethyl acetate, Rf=0.25). An oily product thus obtained was then dissolved in MeOH (3 ml) and 10% TFA (aq.) (3 ml), and stirred at room temperature overnight. Water was added to precipitate a white product, which was collected by filtration to afford 5k (0.05 g, 15.49%). m.p. 194.9-196.0 (decomp.). $^1$H-NMR (500 MHz, DMSO-$d_6$): δ 3.07 (t, J=8.5 Hz, 2H), 4.07 (t, J=8.5 Hz, 2H), 6.34 (d, J=16.0 Hz, 1H), 6.54 (d, J=16.0 Hz, 1H), 7.36 (d, J=16.0 Hz, 1H), 7.45 (d, J=16.0 Hz, 1H), 7.72-7.84 (m, 3H), 8.00 (d, J=8.5 Hz, 2H), 8.18 (s, 1H), 10.70 (s, 1H), 10.83 (s, 1H).

5-Bromo-1-(3-bromophenylsulfonyl)-2,3-dihydro-1H-pyrrolo[2,3-b]pyridine (2l)

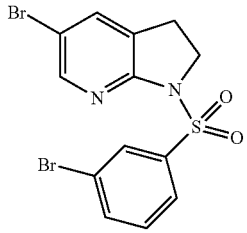 [SMILES: O=S(=O)(c1cccc(Br)c1)N1CCc2cc(Br)cnc21]

A mixture of 1a (0.35 g, 1.76 mmol), 4-bromobenzenesulfonyl chloride (0.67 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.75) to afford 2l (0.56 g, 76.10%) as a yellow solid. $^1$H-NMR (500 MHz, CDCl$_3$): δ 3.07 (t, J=8.5 Hz, 2H), 4.09 (t, J=8.5 Hz, 2H), 7.37 (t, J=8.0 Hz, 1H), 7.48-7.49 (m, 1H), 7.69-7.71 (m, 1H), 8.03-8.05 (m, 1H), 8.19 (d, J=9.0 Hz, 1H), 8.25 (d, J=8.0 Hz, 1H).

(E)-tert-butyl3-(3-(5-((E)-3-tert-butoxy-3-oxoprop-1-enyl)-2,3-dihydro-1H-pyrrolo[2,3-b]pyridin-1-ylsulfonyl)phenyl)acrylate (3l)

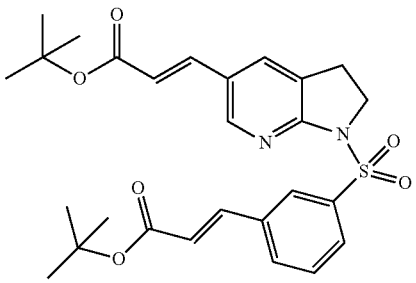 [SMILES: CC(C)(C)OC(=O)/C=C/c1cccc(S(=O)(=O)N2CCc3cc(/C=C/C(=O)OC(C)(C)C)cnc32)c1]

A mixture of 2l (0.56 g, 1.34 mmol), palladium acetate (0.06 g, 0.27 mmol), triphenylphosphine (0.14 g, 0.54 mmol), triethylamine (0.37 ml, 2.68 mmol), sodium bicarbonate (0.45 g, 5.36 mmol), and DMF (3 ml) was stirred for 10 minutes, and, after addition of t-butyl acrylate (0.47 ml, 3.22 mmol) at 120° C., was stirred again overnight. The residue resulting from removal of the solvent was purified with a flash column over silica gel (ethyl acetate:n-hexane=1:2, Rf=0.25) to afford 3l (0.65 g, 94.63%) as a yellow solid. $^1$H-NMR (500 MHz, CDCl$_3$): δ 1.52 (s, 9H), 1.54 (s, 9H), 3.09 (t, J=8.5 Hz, 2H), 4.12 (t, J=8.5 Hz, 2H), 6.24 (d, J=16.0 Hz, 1H), 6.48 (d, J=16.0 Hz, 1H), 7.46 (d, J=16.0 Hz, 1H), 7.49-7.53 (m, 2H), 7.57 (d, J=16.0 Hz, 1H), 7.68 (d, J=8.5 Hz, 1H), 8.10 (d, J=7.5 Hz, 1H), 8.24-8.28 (m, 2H).

(E)-3-(3-(5-((E)-2-carboxyvinyl)-2,3-dihydro-1H-pyrrolo[2,3-b]pyridin-1-ylsulfonyl) phenyl)acrylic acid (4l)

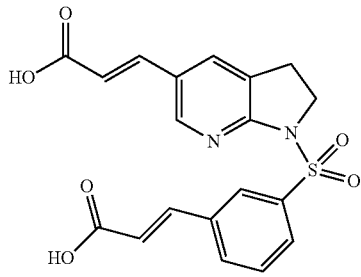 [SMILES: O=C(O)/C=C/c1cccc(S(=O)(=O)N2CCc3cc(/C=C/C(=O)O)cnc32)c1]

A mixture of 3l (0.65 g, 1.27 mmol) and trifluoroacetic acid (6.35 ml) was stirred at room temperature for 2 hours. The reaction mixture was added water to precipitate a white product, which was collected by filtration to afford 4l (0.19 g, 37.36%). $^1$H-NMR (500 MHz, DMSO-$d_6$): δ 3.09 (t, J=8.5 Hz, 2H), 4.15 (t, J=8.5 Hz, 2H), 6.44 (d, J=16.0 Hz, 1H), 6.62 (d, J=16.0 Hz, 1H), 7.49 (d, J=16.0 Hz, 1H), 7.61-7.66 (m, 2H), 7.95 (s, 1H), 8.02 (t, J=9.0 Hz, 2H), 8.21 (s, 1H), 8.26 (s, 1H).

(E)-N-hydroxy-3-(3-(5-((E)-3-(hydroxyamino)-3-oxoprop-1-enyl)-2,3-dihydro-1H-pyrrolo[2,3-b]pyridin-1-ylsulfonyl)phenyl)acrylamide (5l)

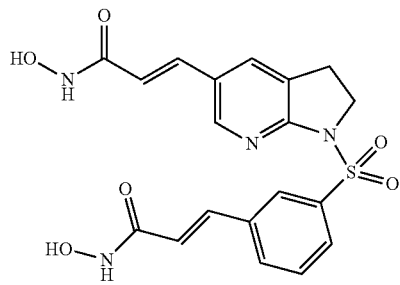 [SMILES: O=C(/C=C/c1cccc(S(=O)(=O)N2CCc3cc(/C=C/C(=O)NO)cnc32)c1)NO]

A mixture of 4l (0.30 g, 0.75 mmol), EDC (0.43 g, 2.25 mmol), HOBt (0.24 g, 1.80 mmol), NMM (0.46 ml, 3.60 mmol), and DMF (2 ml) was stirred for 10 minutes, and, after addition of o-(tetrahydro-2H-pyran-2-yl)hydroxylamine (0.21 g, 1.80 mmol) at room temperature, was stirred again overnight. The residue resulting from removal of the solvent was purified with a flash column over silica gel (ethyl acetate, Rf=0.30). An oily product thus obtained was dissolved in MeOH (5 ml) and 10% TFA (aq.) (5 ml) at room temperature, and was stirred overnight. Water was added to precipitate a white solid, which was collected by filtration to afford 5l (0.12 g, 37.17%). m.p. 219.6-220.7. $^1$H-NMR (500 MHz, DMSO-$d_6$): δ3.09 (t, J=8.5 Hz, 2H), 4.10 (t, J=8.5 Hz, 2H), 6.35 (d, J=16.0 Hz, 1H), 6.56 (d, J=16.0 Hz, 1H), 7.36 (d, J=16.0 Hz, 1H), 7.50 (d, J=16.0 Hz, 1H), 7.61 (t, J=8.5 Hz, 1H), 7.75 (s, 1H), 7.84 (d, J=8.0 Hz, 1H), 7.97 (d, J=8.0 Hz, 1H), 8.22 (d, J=10.0 Hz, 2H), 10.71 (s, 1H), 10.84 (s, 1H).

5-Bromo-1-(2-bromophenylsulfonyl)-2,3-dihydro-1H-pyrrolo[2,3-b]pyridine (2m)

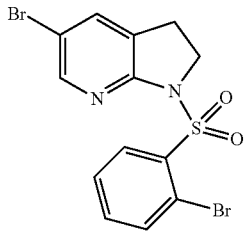 [SMILES: O=S(=O)(c1ccccc1Br)N1CCc2cc(Br)cnc21]

A mixture of 1a (0.35 g, 1.76 mmol), 2-bromobenzenesulfonyl chloride (0.67 g, 2.64 mmol) and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.83) to afford 2m (0.30 g, 40.77%) as a yellow solid. $^1$H-NMR (500 MHz, CDCl$_3$): δ 3.18 (t, J=8.5 Hz, 2H), 4.49 (t, J=8.5 Hz, 2H), 7.38-7.42 (m, 1H), 7.48-7.52 (m, 2H), 7.67 (t, J=8.0 Hz, 1H), 7.92 (s, 1H), 8.43 (d, J=8.0 Hz, 1H).

(E)-Methyl-3-(2-(5-((E)-3-methoxy-3-oxoprop-1-enyl)-2,3-dihydro-1H-pyrrolo[2,3-b]pyridin-1-ylsulfonyl)phenyl)acrylate (3m)

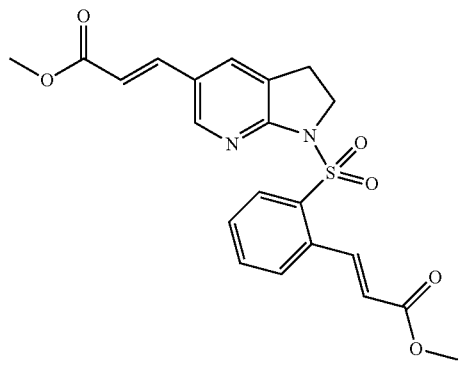

A mixture of 2m (0.31 g, 0.74 mmol), palladium acetate (0.04 g, 0.14 mmol), triphenylphosphine (0.08 g, 0.30 mmol), triethylamine (0.20 ml, 1.48 mmol), sodium bicarbonate (0.24 g, 2.96 mmol), and DMF (2 ml) was stirred for 10 minutes, and, after addition of methyl acrylate (0.16 ml, 1.78 mmol) at 120° C., was stirred again overnight. The residue resulting from removal of the solvent was purified with a flash column over silica gel (ethyl acetate:n-hexane=1:2, Rf=0.38) to afford 3m (0.17 g, 55.11%) as a yellow solid. $^1$H-NMR (500 MHz, CDCl$_3$): δ 3.09 (t, J=8.5 Hz, 2H), 3.74 (s, 3H), 3.79 (s, 3H), 4.32 (t, J=8.5 Hz, 2H), 6.22-6.25 (m, 2H), 7.48 (d, J=16.0 Hz, 1H), 7.51-7.57 (m, 4H), 7.98 (s, 1H), 8.32 (d, J=7.5 Hz, 1H), 8.52 (d, J=16.0 Hz, 1H).

(E)-3-(2-(5-((E)-2-carboxyvinyl)-2,3-dihydro-1H-pyrrolo[2,3-b]pyridin-1-ylsulfonyl) phenyl)acrylic acid (4m)

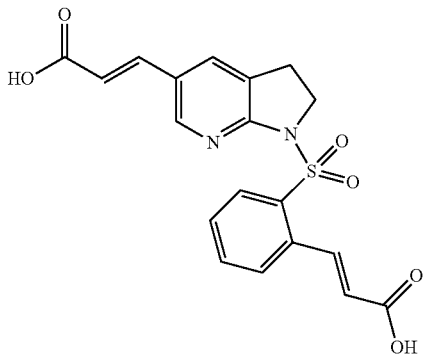 [SMILES: O=C(O)/C=C/c1cnc2c(c1)CCN2S(=O)(=O)c1ccccc1/C=C/C(=O)O]

A mixture of 3m (0.30 g, 0.70 mmol), dioxane (5 ml), and 1M LiOH (aq.) (2.88 ml, 2.80 mmol) was stirred overnight at 40° C. After the solvent was removed, the resultant residue was dissolved in water. 3N HCl (aq.) was added to precipitate a yellow product, which was collected by filtration to afford 4m (0.17 g, 60.65%). $^1$H-NMR (500 MHz, DMSO-$d_6$): δ 3.11 (t, J=8.5 Hz, 2H), 4.32 (t, J=8.5 Hz, 2H), 6.39-6.43 (m, 2H), 7.45 (d, J=16.0 Hz, 1H), 7.64 (t, J=8.0 Hz, 1H), 7.70 (t, J=8.0 Hz, 1H), 7.86 (d, J=7.5 Hz, 1H), 7.95 (s, 1H), 8.07 (s, 1H), 8.14 (d, J=8.0 Hz, 1H), 8.33 (d, J=16.0 Hz, 1H).

(E)-N-hydroxy-3-(2-(5-((E)-3-(hydroxyamino)-3-oxoprop-1-enyl)-2,3-dihydro-1H-pyrrolo[2,3-b]pyridin-1-ylsulfonyl)phenyl)acrylamide (5m)

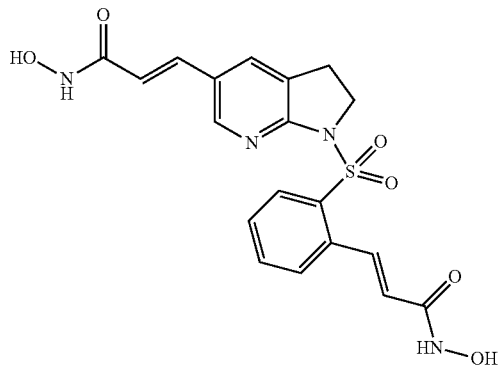 [SMILES: O=C(/C=C/c1cnc2c(c1)CCN2S(=O)(=O)c1ccccc1/C=C/C(=O)NO)NO]

A mixture of 4m (0.17 g, 0.42 mmol), EDC (0.24 g, 1.26 mmol), HOBt (0.14 g, 1.01 mmol), NMM (0.22 ml, 2.02 mmol), and DMF (2 ml) was stirred for 10 minutes, and, after addition of o-(tetrahydro-2H-pyran-2-yl)hydroxylamine (0.12 g, 1.01 mmol) at room temperature, was stirred again overnight. The residue resulting from removal of the solvent was purified with a flash column over silica gel (ethyl acetate:n-hexane=4:1, Rf=0.10). An oily product thus obtained was dissolved in MeOH (2 ml) and 10% TFA (aq.) (2 ml) at room temperature, was stirred again overnight. Water was added to precipitate a pale yellow solid, which was collected by filtration to afford 5m (0.06 g, 33.19%). m.p. 220.2-221.4. $^1$H-NMR (500 MHz, DMSO-$d_6$): δ 3.10 (t, J=8.5 Hz, 2H), 4.28 (t, J=8.5 Hz, 2H), 6.26-6.33 (m, 2H), 7.31 (d, J=16.0 Hz, 1H), 7.60-7.71 (m, 3H), 7.74 (s, 1H), 7.96 (s, 1H), 8.14-8.17 (m, 2H), 8.99 (br, 1H), 9.17 (br, 1H), 10.69 (s, 1H), 10.83 (s, 1H).

4-(5-Bromo-2,3-dihydro-1H-pyrrolo[2,3-b]pyridin-1-ylsulfonyl)benzonitrile (2n)

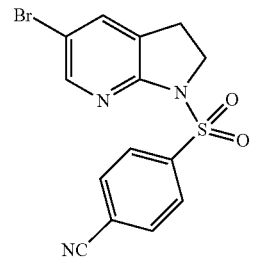 [SMILES: N#Cc1ccc(S(=O)(=O)N2CCc3cc(Br)cnc32)cc1]

A mixture of 1 (0.35 g, 1.76 mmol), 4-cyanobenzenesulfonyl chloride (0.39 g, 2.64 mmol), and pyridine (2 ml) was stirred at room temperature overnight. The reaction was quenched with water and the mixture was extracted with ethyl acetate (30 ml*3). The organic layer was collected and dried over anhydrous MgSO$_4$, and concentrated in vacuo to yield a brown residue, which was purified by a flash column over silica gel (ethyl acetate:n-hexane=1:1, Rf=0.58) to afford 2n (0.35 g, 54.60%) as a yellow solid. $^1$H-NMR (500 MHz, CDCl$_3$): δ 3.09 (t, J=8.5 Hz, 2H), 4.11 (t, J=8.5 Hz, 2H), 7.50 (s, 1H), 7.79 (d, J=8.5 Hz, 2H), 8.17 (s, 1H), 8.23 (d, J=8.5 Hz, 2H).

(E)-tert-butyl 3-(1-(4-cyanophenylsulfonyl)-2,3-dihydro-1H-pyrrolo[2,3-b]pyridine-5-yl)acrylate (3n)

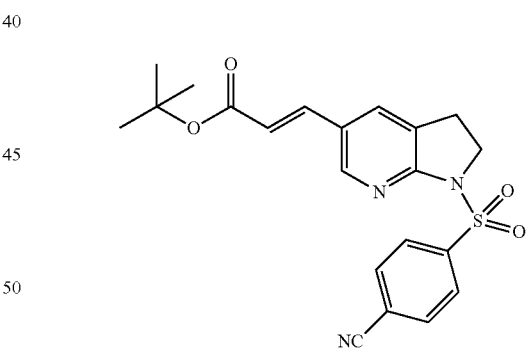

A mixture of 2n (0.15 g, 0.41 mmol), Pd$_2$(dba)$_3$ (0.04 g, 0.04 mmol), [(t-Bu)$_3$PH]BF$_4$ (0.02 g, 0.08 mmol), triethylamine (0.06 ml, 0.41 g), sodium bicarbonate (0.07 g, 0.82 mmol) and DMF (1 ml) was stirred for 10 minutes, and, after addition of t-butyl acrylate (0.07 ml, 0.49 mmol) at 120° C., was stirred again overnight. The residue resulting from removal of the solvent was purified with a flash column over silica gel (ethyl acetate:n-hexane=1:2, Rf=0.35) to afford 3n (0.20 g, 34.04%) as a yellow solid. $^1$H-NMR (500 MHz, CDCl$_3$): δ 1.52 (s, 9H), 3.12 (t, J=8.5 Hz, 2H), 4.14 (t, J=8.5 Hz, 2H), 6.25 (d, J=16.0 Hz, 1H), 7.46 (t, J=16.0 Hz, 1H), 7.56 (s, 1H), 7.79 (d, J=8.5 Hz, 2H), 8.21 (s, 1H), 8.27 (d, J=8.5 Hz, 2H).

(E)-3-(1-(4-cyanophenylsulfonyl)-2,3-dihydro-1H-pyrrolo[2,3-b]pyridin-5-yl)acrylic acid (4n)

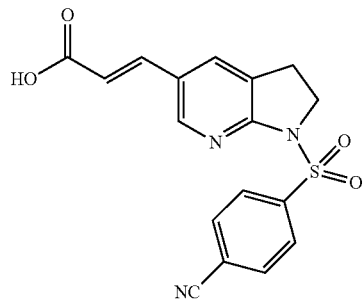 [SMILES: N#Cc1ccc(S(=O)(=O)N2CCc3cc(/C=C/C(=O)O)cnc32)cc1]

A mixture of 3n (0.20 g, 0.49 mmol) and trifluoroacetic acid (1.63 ml) and stirred at 0° C. for 40 minutes. The reaction mixture was added water to precipitate a white product, which was collected by filtration to afford 4n (0.15 g, 86.14%). $^1$H-NMR (500 MHz, DMSO-$d_6$): δ 3.10 (t, J=8.5 Hz, 2H), 4.13 (t, J=8.5 Hz, 2H), 6.45 (d, J=16.0 Hz, 1H), 7.50 (t, J=16.0 Hz, 1H), 7.96 (s, 1H), 8.07 (d, J=9.0 Hz, 2H), 8.18 (d, J=8.5 Hz, 2H), 8.25 (s, 1H).

(E)-3-(1-(4-cyanophenylsulfonyl)-2,3-dihydro-1H-pyrrolo[2,3-b]pyridin-5-yl) N-hydroxyacrylamide (5n)

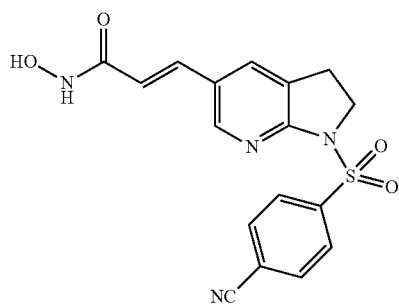 [SMILES: N#Cc1ccc(S(=O)(=O)N2CCc3cc(/C=C/C(=O)NO)cnc32)cc1]

A mixture of 4n (0.15 g, 0.42 mmol), EDC (0.12 g, 0.63 mmol), HOBt (0.07 g, 0.50 mmol), NMM (0.11 ml, 1.01 mmol), and DMF (1 ml) was stirred for 10 minutes, and, after addition of o-(tetrahydro-2H-pyran-2-yl)hydroxylamine (0.06 g, 0.50 mmol) at room temperature, was stirred again overnight. The residue resulting from removal of the solvent was purified with a flash column over silica gel (ethyl acetate:n-hexane=2:1, Rf=0.25). An oily product thus obtained was dissolved in MeOH (4 ml) and 10% TFA (aq.) (4 ml) at room temperature, and stirred overnight. Water was added to precipitate a yellow solid, which was collected by filtration to afford 5n (0.12 g, 77.14%). m.p. 226.2-227.4. $^1$H-NMR (500 MHz, CD$_3$OD): δ 3.10 (t, J=8.5 Hz, 2H), 4.12 (t, J=8.5 Hz, 2H), 6.36 (d, J=16.0 Hz, 1H), 7.36 (t, J=16.0 Hz, 1H), 7.77 (s, 1H), 8.07 (d, J=8.5 Hz, 2H), 8.18 (d, J=8.5 Hz, 3H).

5-Bromo-1-(naphthalen-1-ylsulfonyl)-2,3-dihydro-1H-pyrrolo[2,3-b]pyridine (2o)

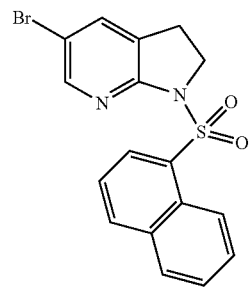 [SMILES: O=S(=O)(c1cccc2ccccc12)N1CCc2cc(Br)cnc21]

A mixture of 1a (0.35 g, 1.76 mmol), 4-naphthalene sulfonyl chloride (0.60 g, 2.64 mmol) and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.75) to afford 2o (0.30 g, 43.79%) as a yellow solid. $^1$H-NMR (500 MHz, CDCl$_3$): δ 3.06 (t, J=8.5 Hz, 2H), 4.32 (t, J=8.5 Hz, 2H), 7.42 (s, 1H), 7.55-7.59 (m, 2H), 7.62-7.66 (m, 1H), 7.91 (d, J=8.0 Hz, 1H), 8.05 (s, 1H), 8.07 (d, J=8.0 Hz, 1H), 8.53 (d, J=8.5 Hz, 1H), 8.83 (d, J=8.5 Hz, 1H).

(E)-Methyl 3-(1-(naphthalen-1-ylsulfonyl)-2,3-dihydro-1H-pyrrolo[2,3-b]pyridin-5-yl)acrylate (3o)

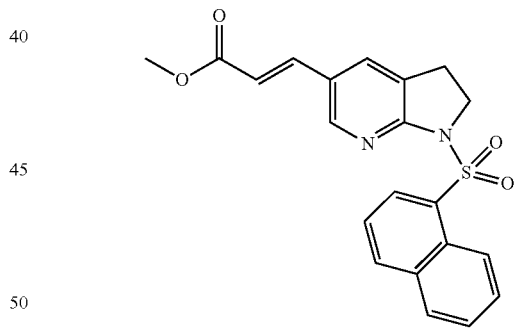

A mixture of 2o (0.29 g, 0.74 mmol), palladium acetate (0.02 g, 0.07 mmol), triphenylphosphine (0.04 g, 0.15 mmol), triethylamine (0.10 ml, 0.74 g), sodium bicarbonate (0.12 g, 1.48 mmol), and DMF (2 ml) was stirred for 10 minutes, and, after addition of methyl acrylate (0.08 ml, 0.89 mmol) at 120° C., was stirred again overnight. The residue resulting from removal of the solvent was purified with a flash column over silica gel (ethyl acetate:n-hexane=1:1, Rf=0.50) to afford 3o (0.20 g, 68.52%) as a yellow solid. $^1$H-NMR (500 MHz, CDCl$_3$): δ 3.10 (t, J=8.5 Hz, 2H), 3.77 (s, 3H), 4.36 (t, J=8.5 Hz, 2H), 6.26 (d, J=16.0 Hz, 1H), 7.51 (s, 1H), 7.54-7.61 (m, 2H), 7.63-7.66 (m, 2H), 7.91 (d, J=9.0 Hz, 1H), 8.08 (d, J=8.0 Hz, 1H), 8.11 (s, 1H), 8.57 (d, J=8.5 Hz, 1H), 8.85 (d, J=9.0 Hz, 1H).

(E)-3-(1-(Naphthalen-1-ylsulfonyl)-2,3-dihydro-1H-pyrrolo[2,3-b]pyridin-5-yl)acrylic acid (4o)

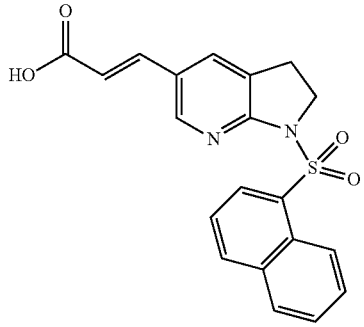 [SMILES: O=C(O)/C=C/c1cnc2c(c1)CCN2S(=O)(=O)c1cccc2ccccc12]

To a mixture of 3o (0.20 g, 0.51 mmol) and dioxane (3 ml) was added 1M LiOH (aq.) (1.02 ml, 1.02 mmol). The mixture was stirred overnight at 40° C. After the solvent was removed, the resultant residue was dissolved in water. 3N HCl (aq.) was added to precipitate a white product, which was collected by filtration to afford 4o (0.15 g, 77.31 %). $^1$H-NMR (500 MHz, DMSO-$d_6$): δ 3.13 (t, J=8.5 Hz, 2H), 4.32 (t, J=8.5 Hz, 2H), 6.41 (d, J=16.0 Hz, 1H), 7.45 (d, J=16.0 Hz, 1H), 7.65 (t, J=7.5 Hz, 1H), 7.69-7.74 (m, 2H), 7.92 (s, 1H), 8.08 (d, J=8.0 Hz, 1H), 8.11 (s, 1H), 8.28 (d, J=8.0 Hz, 1H), 8.41 (d, J=7.0 Hz, 1H), 8.64 (d, J=8.5 Hz, 1H).

(E)-N-hydroxy-3-(1-(naphthalen-1-ylsulfonyl)-2,3-dihydro-1H-pyrrolo[2,3-b]pyridine5-yl)acrylamide (5o)

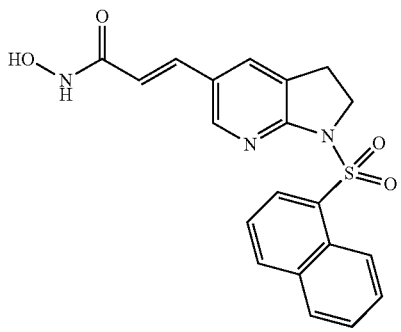 [SMILES: O=C(/C=C/c1cnc2c(c1)CCN2S(=O)(=O)c1cccc2ccccc12)NO]

A mixture of 4o (0.30 g, 0.79 mmol), EDC (0.23 g, 1.19 mmol), HOBt (0.13 g, 0.95 mmol), NMM (0.21 ml, 1.90 mmol), and DMF (2 ml) was stirred for 10 minutes, and, after addition of o-(tetrahydro-2H-pyran-2-yl)hydroxylamine (0.11 g, 0.90 mmol) at room temperature, was stirred again overnight. The residue resulting from removal of the solvent was purified with a flash column over silica gel (ethyl acetate:n-hexane=2:1, Rf=0.18). An oily product thus obtained was then dissolved in MeOH (3 ml) and 10% TFA (aq.) (3 ml), and stirred at room temperature overnight. Water was added to precipitate a yellow solid, which was collected by filtration to afford 5o (0.20 g, 64.02%). m.p. 164.5-165.7. $^1$H-NMR (500 MHz, DMSO-$d_6$): δ 3.13 (t, J=8.5 Hz, 2H), 4.31 (t, J=8.5 Hz, 2H), 6.31 (d, J=16.0 Hz, 1H), 7.31 (d, J=16.0 Hz, 1H), 7.65 (t, J=7.5 Hz, 1H), 7.69-7.74 (m, 3H), 8.04 (s, 1H), 8.08 (d, J=8.0 Hz, 1H), 8.27 (d, J=8.5 Hz, 1H), 8.40 (d, J=8.0 Hz, 1H), 8.65 (d, J=8.5 Hz, 1H).

5-(5-Bromo-2,3-dihydro-1H-pyrrolo[2,3-b]pyridin-1-ylsulfonyl)-N,N-dimethyl-naphthalen-1-amine (2p)

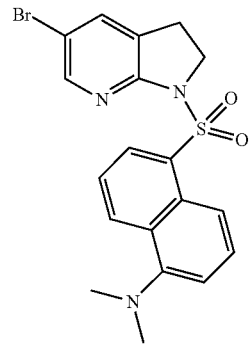 [SMILES: CN(C)c1cccc2c(S(=O)(=O)N3CCc4cc(Br)cnc43)cccc12]

A mixture of 1a (0.35 g, 1.76 mmol), dansyl sulfonyl chloride (0.71 g, 2.64 mmol), and pyridine (3 ml) was refluxed overnight. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:2, Rf=0.68) to afford 2a (0.17 g, 22.34%) as a yellow solid. $^1$H-NMR (500 MHz, CDCl$_3$): δ 2.91 (s, 6H), 3.06 (t, J=8.5 Hz, 2H), 4.31 (t, J=8.5 Hz, 2H), 7.21 (s, 1H), 7.42 (s, 1H), 7.53-7.60 (t, J=8.0 Hz, 1H), 8.04 (s, 1H), 8.52 (d, J=7.5 Hz, 2H), 8.62 (s, 1H).

(E)-Methyl-3-(1-(5-(dimethylamino)naphthalen-1-ylsulfonyl)-2,3-dihydro-1H-pyrrolo[2,3-b]pyridin-5-yl)acrylate (3p)

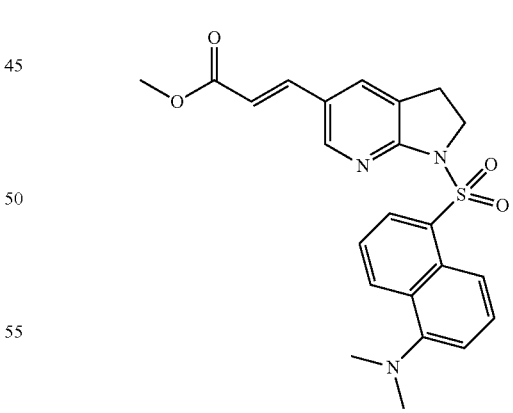

A mixture of 2p (0.37 g, 0.86 mmol), palladium acetate (0.02 g, 0.09 mmol), triphenylphosphine (0.04 g, 0.17 mmol), triethylamine (0.12 ml, 0.86 mmol), sodium bicarbonate (0.14 g, 1.72 mmol), and DMF (2 ml) was stirred for 10 minutes, and, after addition of t-butyl acrylate (0.09 ml, 1.03 mmol) at 120° C., was stirred again overnight. The residue resulting from removal of the solvent was purified with a flash column over silica gel (ethyl acetate:n- hexane=1:1, Rf=0.50) to afford 3p (0.17 g, 45.18%) as a yellow solid. ¹H-NMR (500 MHz, CD₃OD+DMSO-d₆): δ 2.89 (s, 6H), 3.19 (t, J=8.5 Hz, 2H), 4.24 (s, 3H), 4.37 (t, J=8.5 Hz, 2H), 6.50 (d, J=16.0 Hz, 1H), 7.29 (d, J=8.0 Hz, 1H), 7.59-7.64 (m, 2H), 7.69 (t, J=8.0 Hz, 1H), 7.88 (s, 1H), 8.13 (s, 1H), 8.41 (d, J=9.0 Hz, 1H), 8.48 (d, J=8.0 Hz, 1H), 8.62 (d, J=8.5 Hz, 1H).

(E)-3-(1-(5-(Dimethylamino)naphthalen-1-ylsulfonyl)-2,3-dihydro-1H-pyrrolo[2,3-b]pyridin-5-yl) acrylic acid (4p)

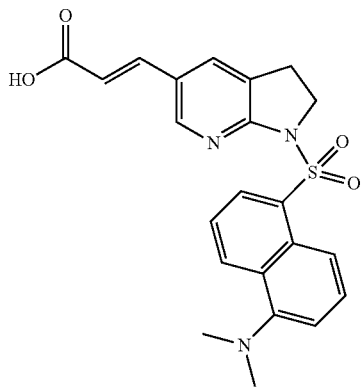 [SMILES: CN(C)c1cccc2c(S(=O)(=O)N3CCc4cc(/C=C/C(=O)O)cnc43)cccc12]

To a mixture of 3p (0.17 g, 0.39 mmol) and dioxane (3 ml) was added 1M LiOH (aq.) (0.78 ml, 0.78 mmol). The mixture was stirred overnight at 40° C. After the solvent was removed, the resultant residue was dissolved in water. 3N HCl (aq.) was added to precipitate a yellow product, which was collected by filtration to afford 4p (0.05 g, 30.27 %). ¹H-NMR (500 MHz, CD₃OD): δ 3.12 (t, J=8.5 Hz, 2H), 3.13 (s, 6H), 4.31 (t, J=8.5 Hz, 2H), 6.37 (d, J=15.5 Hz, 1H), 7.52 (d, J=16.0 Hz, 1H), 7.72-7.83 (m, 4H), 8.01 (s, 1H), 8.56 (t, J=7.5 Hz, 2H), 8.79 (s, 1H).

(E)-3-(1-(5-(dimethylamino)naphthalen-1-ylsulfonyl)-2,3-dihydro-1H-pyrrolo[2,3-b]pyridin-5-yl)-N-hydroxyacrylamide (5p)

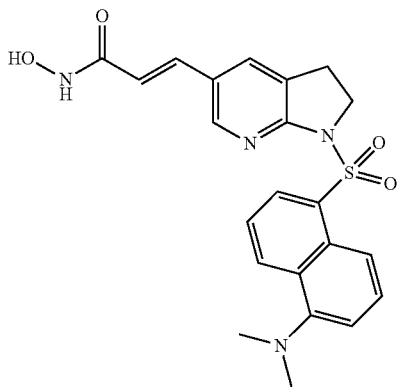 [SMILES: CN(C)c1cccc2c(S(=O)(=O)N3CCc4cc(/C=C/C(=O)NO)cnc43)cccc12]

A mixture of 4p (0.23 g, 0.54 mmol), EDC (0.16 g, 0.81 mmol), HOBt (0.09 g, 0.65 mmol), NMM (0.14 ml, 1.30 mmol), and DMF (2 ml) was stirred for 10 minutes, and, after addition of o-(tetrahydro-2H-pyran-2-yl)hydroxylamine (0.08 g, 0.65 mmol) at room temperature, was stirred again overnight. The residue resulting from removal of the solvent was purified with a flash column over silica gel (ethyl acetate:n-hexane=2:1, Rf=0.20). An oily product thus obtained was then dissolved in MeOH (3 ml) and 10% TFA (aq.) (3 ml), and stirred at room temperature overnight. Water was added to precipitate a pale yellow solid, which was collected by filtration to afford 5p (0.11 g, 46.45%). m.p. 183.1-184.7. ¹H-NMR (500 MHz, DMSO-d₆): δ 2.80 (s, 6H), 3.14 (t, J=8.5 Hz, 2H), 4.30 (t, J=8.5 Hz, 2H), 6.32 (d, J=15.5 Hz, 1H), 7.24 (d, J=7.5 Hz, 1H), 7.32 (d, J=16.0 Hz, 1H), 7.60 (t, J=8.0 Hz, 1H), 7.68 (t, J=8.0 Hz, 1H), 7.73 (s, 1H), 8.05 (s, 1H), 8.27 (d, J=9.0 Hz, 1H), 8.38 (d, J=7.0 Hz, 1H), 8.50 (t, J=8.0 Hz, 1H), 10.70 (s, 1H).

(E)-N-(2-aminophenyl)-3-(1-(4-methoxyphenylsulfonyl)-2,3-dihydro-1H-pyrrolo[2,3-b]pyridin-5-yl) acrylamide (6a)

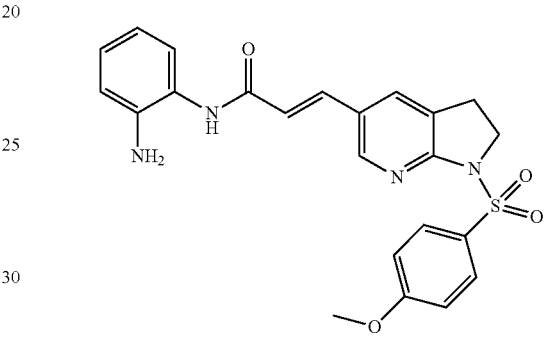

A mixture of 4b (0.20 g, 0.55 mmol), EDC (0.16 g, 0.83 mmol), HOBt (0.09 g, 0.66 mmol), NMM (0.15 ml, 1.32 mmol) and DMF (1.5 ml) was stirred for 10 minutes, then added o-phenyldiamine (0.07 g, 0.66 mmol) at room temperature, was stirred again overnight. The residue resulting from removal of the solvent was purified with a flash column over silica gel (ethyl acetate:n-hexane=4:1, Rf=0.28) to afford 6a (0.16 g, 64.57%) as an orange solid. m.p. 209.1-209.9. ¹H-NMR (500 MHz, DMSO-d₆): δ 3.09 (t, J=8.5 Hz, 2H), 3.80 (s, 3H), 4.04 (t, J=8.5 Hz, 2H), 4.91 (s, 2H), 6.56 (t, J=7.5 Hz, 1H), 6.73 (d, J=8.0 Hz, 1H), 6.79 (d, J=16.0 Hz, 1H), 6.90 (t, J=7.5 Hz, 1H), 7.09 (d, J=9.0 Hz, 2H), 7.31 (d, J=8.0 Hz, 1H), 7.47 (d, J=15.5 Hz, 1H), 7.76 (s, 1H), 7.95 (d, J=9.0 Hz, 2H), 8.25 (s, 1H), 9.35 (s, 1H).

N-hydroxy-3-(1-(4-methoxyphenylsulfonyl)-2,3-dihydro-1H-pyrrolo[2,3-b]pyridine-5-yl)propanamide (7a)

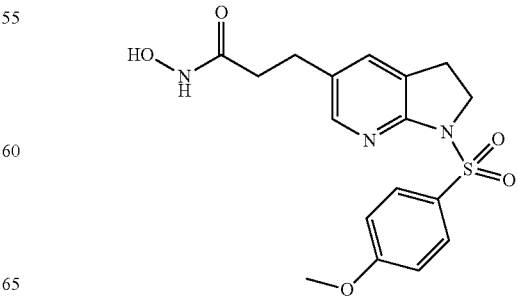

A mixture of 5b (0.11 g, 0.29 mmol) and methyl alcohol (4 ml) was stirred for 10 minutes, and, after addition of catalyst 10% palladium on carbon at room temperature, was stirred again under hydrogen gas overnight. The residue was washed by MeOH and through celite to remove 10% palladium on carbon without more purification to afford 7a (0.09 g, 82.23%) as a dark pink solid. m.p. 151.0-151.7. $^1$H-NMR (500 MHz, DMSO-$d_6$): δ 2.18 (t, J=7.5 Hz, 2H), 2.68 (t, J=7.5 Hz, 2H), 2.97 (t, J=8.5 Hz, 2H), 3.79 (s, 3H), 3.93 (t, J=8.5 Hz, 2H), 7.06 (d, J=9.0 Hz, 2H), 7.36 (s, 1H), 7.85 (s, 1H), 7.90 (t, J=9.0 Hz, 2H).

1-(4-Methoxyphenylsulfonyl)-2,3-dihydro-1H-pyrrolo[2,3-b]pyridine-5-carbonitrile (8a)

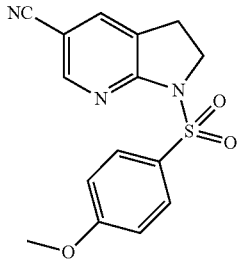 [SMILES: COc1ccc(S(=O)(=O)N2CCc3cc(C#N)cnc32)cc1]

A mixture of 2b (0.20 g, 0.54 mmol), copper (I) cyanide (0.10 g, 1.08 mmol) and DMF (3 ml) was stirred at 150° C. overnight. The residue resulting from removal of the solvent was purified with a flash column over silica gel (ethyl acetate:n-hexane=1:1, Rf=0.43) to afford 8a (0.09 g, 52.58%) as a yellow solid. $^1$H-NMR (500 MHz, CD$_3$OD): δ 3.10 (t, J=8.5 Hz, 2H), 3.85 (s, 3H), 4.14 (t, J=8.5 Hz, 2H), 6.96 (d, J=9.0 Hz, 2H), 7.51 (s, 1H), 8.03 (t, J=9.0 Hz, 2H), 8.40 (s, 1H).

1-(4-Methoxyphenylsulfonyl)-2,3-dihydro-1H-pyrrolo[2,3-b]pyridine-5-carboxylic acid (9a)

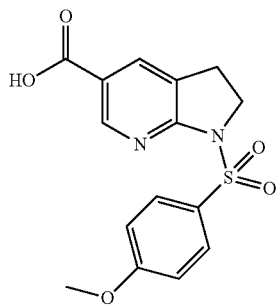 [SMILES: COc1ccc(S(=O)(=O)N2CCc3cc(C(=O)O)cnc32)cc1]

To a mixture of 8a (0.09 g, 0.29 mmol) and methyl alcohol (3 ml) was added 10% KOH (aq.) (3 ml). The mixture was refluxed for 2 hours. After it was cooled to room temperature, 3 N HCl (aq.) was then added to precipitate a white product, which was collected by filtration to afford 9a (0.06 g, 61.88%). $^1$H-NMR (500 MHz, CD$_3$OD): δ 3.09 (t, J=8.5 Hz, 2H), 3.83 (s, 3H), 4.09 (t, J=8.5 Hz, 2H), 7.04 (d, J=9.0 Hz, 2H), 7.97-8.00 (m, 3H), 8.66 (s, 1H).

N-hydroxy-1-(4-methoxyphenylsulfonyl)-2,3-dihydro-1H-pyrrolo[2,3-b]pyridine-5-carboxamide (10a)

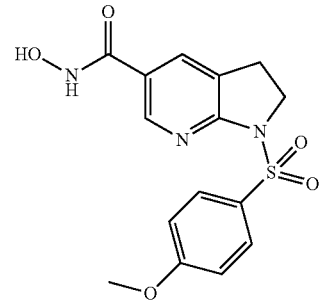 [SMILES: COc1ccc(S(=O)(=O)N2CCc3cc(C(=O)NO)cnc32)cc1]

A mixture of 9a (0.31 g, 0.93 mmol), EDC (0.27 g, 1.40 mmol), HOBt (0.15 g, 1.12 mmol), NMM (0.28 ml, 2.23 mmol), and DMF (2 ml) was stirred for 10 minutes, and, after addition of o-(tetrahydro-2H-pyran-2-yl)hydroxylamine (0.11 g, 1.12 mmol) at room temperature, was stirred again overnight. The residue resulting from removal of the solvent was purified with a flash column over silica gel (ethyl acetate:n-hexane=2:1, Rf=0.30). An oily product thus obtained was dissolved in MeOH (5 ml) and 10% TFA (aq.) (5 ml) at room temperature, and stirred overnight. Water was added to precipitate a white solid, which was collected by filtration to afford 10a (0.22 g, 74.09%). m.p. 198.5-199.9. $^1$H-NMR (500 MHz, DMSO-$d_6$): δ 3.07 (t, J=8.5 Hz, 2H), 3.80 (s, 3H), 4.03 (t, J=8.5 Hz, 2H), 7.08 (d, J=9.0 Hz, 2H), 7.80 (s, 1H), 7.94 (d, J=9.0 Hz, 2H), 8.36 (s, 1H).

5-Bromo-1-(phenylsulfonyl)-1H-pyrrolo[2,3-b]pyridine (11a)

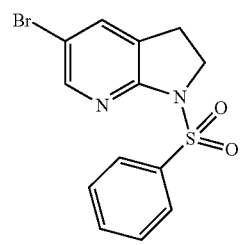 [SMILES: O=S(=O)(c1ccccc1)N1CCc2cc(Br)cnc21]

To a mixture of 5-bromo-7-azaindole (1.00 g, 5.08 mmol) and DMF (3 ml) was added 60% NaH (0.13 g, 5.59 mmol). The mixture was stirred for 10 minutes, and, after addition of benzenesulfonyl chloride (0.71 ml, 5.59 mmol), was stirred again overnight at room temperature. The reaction was quenched with water and the mixture was extracted with ethyl acetate (30 ml×3). The organic layer was collected, dried over anhydrous MgSO$_4$, and concentrated in vacuo to yield a brown residue, which was purified by a flash column over silica gel (ethyl acetate:n-hexane=1:1, Rf=0.40) to afford 11a (0.95 g, 55.46%) as a yellow solid. $^1$H-NMR (500 MHz, CDCl$_3$): δ 6.55 (d, J=4.5 Hz, 1H), 7.50 (t, J=8.0 Hz, 2H), 7.59 (t, J=7.5 Hz, 1H), 7.74 (d, J=4.0 Hz, 1H), 7.97 (d, J=2.0 Hz, 1H), 8.17 (t, J=8.0 Hz, 2H), 8.45 (d, J=2.0 Hz, 1H).

83
(E)-tert-Butyl 3-(1-(phenylsulfonyl)-1H-pyrrolo[2,3-b]pyridin-5-yl)acrylate (12a)

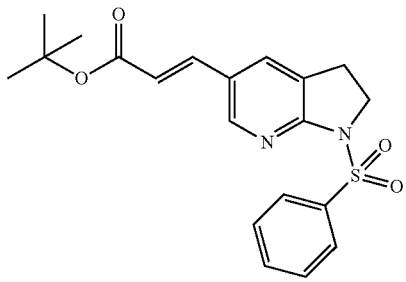 [SMILES: CC(C)(C)OC(=O)/C=C/c1cnc2c(c1)CCN2S(=O)(=O)c1ccccc1]

A mixture of 11a (0.15 g, 0.44 mmol), palladium acetate (0.01 g, 0.04 mmol), triphenylphosphine (0.03 g, 0.09 mmol), triethylamine (0.06 ml, 0.44 mmol), sodium bicarbonate (0.07 g, 0.88 mmol), and DMF (1.5 ml) was stirred for 10 minutes, and, after addition of t-butyl acrylate (0.08 ml, 0.53 mmol) at 120° C., was stirred again overnight. The residue resulting from removal of the solvent was purified with a flash column over silica gel (ethyl acetate:n-hexane=1:5, Rf=0.20) to afford 12a (0.11 g, 65.03%) as a yellow solid. $^1$H-NMR (500 MHz, CDCl$_3$): δ 1.54 (s, 9H), 6.40 (d, J=16.0 Hz, 1H), 6.61 (d, J=3.5 Hz, 1H), 7.50 (t, J=7.5 Hz, 2H), 7.59 (t, J=7.5 Hz, 1H), 7.64 (d, J=16.0 Hz, 1H), 7.75 (d, J=4.0 Hz, 1H), 7.97 (d, J=2.0 Hz, 1H), 8.20 (t, J=8.5 Hz, 2H), 8.55 (d, J=2.0 Hz, 1H).

(E)-3-(1-(Phenylsulfonyl)-1H-pyrrolo[2,3-b]pyridin-5-yl)acrylic acid (13a)

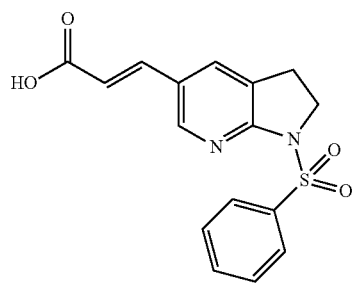 [SMILES: O=C(O)/C=C/c1cnc2c(c1)CCN2S(=O)(=O)c1ccccc1]

A mixture of 12a (1.27 g, 3.30 mmol) and trifluoroacetic acid (11.0 ml) was stirred at room temperature for 2 hours. The reaction mixture was added water to precipitate a white product, which was collected by filtration to afford 13a (0.80 g, 73.84%). $^1$H-NMR (500 MHz, CD$_3$OD): δ 6.57 (d, J=16.0 Hz, 1H), 6.77 (d, J=4.0 Hz, 1H), 7.54 (t, J=8.0 Hz, 2H), 7.65 (t, J=7.5 Hz, 1H), 7.75 (d, J=16.0 Hz, 1H), 7.85 (d, J=4.0 Hz, 1H), 8.13 (t, J=8.0 Hz, 2H), 8.25 (s, 1H), 8.52 (s, 1H).

84
(E)-N-hydroxy-3-(1-(phenylsulfonyl)-1H-pyrrolo[2,3-b]pyridin-5-yl)acrylamide (14a)

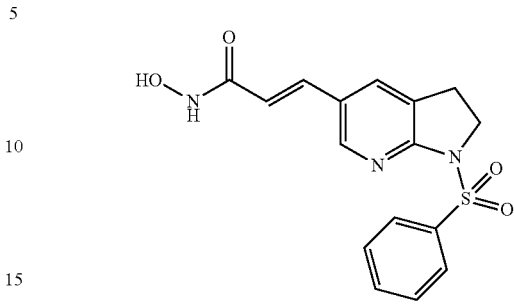

A mixture of 13a (2.00 g, 6.09 mmol), EDC (1.52 g, 9.14 mmol), HOBt (0.99 g, 7.31 mmol), NMM (1.61 ml, 4.62 mmol), and DMF (3 ml) was stirred for 10 minutes, and, after addition of o-(tetrahydro-2H-pyran-2-yl)hydroxylamine (0.86 g, 7.31 mmol) at room temperature, was stirred again overnight. The residue resulting from removal of the solvent was purified with a flash column over silica gel (ethyl acetate:n-hexane=2:1, Rf=0.25). An oily product thus obtained was dissolved in MeOH (2 ml) and 10% TFA (aq.) (2 ml) at room temperature, and stirred overnight. Water was added to precipitate a white solid, which was collected by filtration to afford 14a (1.00 g, 88.79%). m.p. 210.2-211.5. $^1$H-NMR (500 MHz, DMSO-d6): δ 6.57 (d, J=15.5 Hz, 1H), 6.75 (d, J=7.0 Hz, 1H), 7.54 (t, J=7.5 Hz, 2H), 7.64 (t, J=7.5 Hz, 1H), 7.69 (d, J=16.0 Hz, 1H), 7.85 (d, J=6.5 Hz, 1H), 8.13 (t, J=8.5 Hz, 2H), 8.17 (s, 1H), 8.51 (s, 1H).

5-Bromo-1-(4-methoxyphenylsulfonyl)-1H-pyrrolo[2,3-b]pyridine (11b)

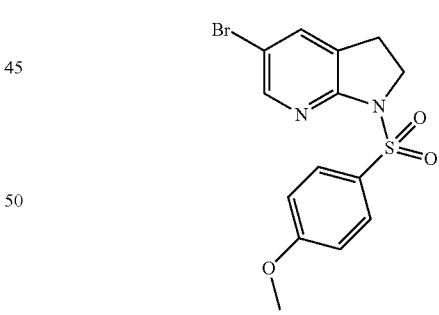

A mixture of 5-bromo-7-azaindole (0.35 g, 1.78 mmol), DMF (2 ml), and 60% NaH (0.06 g, 2.67 mmol) was stirred for 10 minutes, after addition of 4-methoxybenzenesulfonyl chloride (0.55 g, 2.67 mmol), was stirred again at room temperature overnight. Water was added to precipitate a white product, which was collected by filtration to afford 11b (0.57 g, 87.20%). $^1$H-NMR (500 MHz, CDCl$_3$): δ 3.83 (s, 3H), 6.52 (d, J=4.0 Hz, 1H), 6.93 (t, J=9.0 Hz, 2H), 7.73 (t, J=4.0 Hz, 1H), 7.96 (d, J=2.0 Hz, 1H), 8.11 (d, J=9.0 Hz, 2H), 8.44 (d, J=2.5 Hz, 1H).

(E)-tert-Butyl 3-(1-(4-methoxyphenylsulfonyl)-1H-pyrrolo[2,3-b]pyridin-5-yl) acrylate (12b)

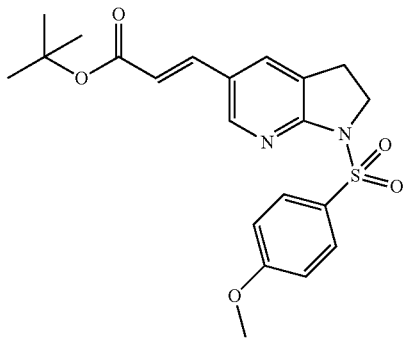 [SMILES: COc1ccc(S(=O)(=O)N2CCc3cc(/C=C/C(=O)OC(C)(C)C)cnc32)cc1]

A mixture of 11b (0.57 g, 1.55 mmol), palladium acetate (0.04 g, 0.16 mmol), triphenylphosphine (0.08 g, 0.31 mmol), triethylamine (0.22 ml, 1.55 mmol), sodium bicarbonate (0.26 g, 3.10 mmol), and DMF (2 ml) was stirred for 10 minutes, and, after addition of t-butyl acrylate (0.27 ml, 1.86 mmol) at 120° C., was stirred again overnight. The residue resulting from removal of the solvent was purified with a flash column over silica gel (ethyl acetate:n-hexane=1:4, Rf=0.33) to afford 12b (0.58 g, 90.28%) as a yellow solid. $^1$H-NMR (500 MHz, CDCl$_3$): δ 1.54 (s, 9H), 3.82 (s, 3H), 6.40 (d, J=16.0 Hz, 1H), 6.58 (d, J=4.0 Hz, 1H), 6.94 (t, J=9.0 Hz, 2H), 7.64 (d, J=16.0 Hz, 1H), 7.74 (t, J=4.0 Hz, 1H), 7.97 (d, J=2.0 Hz, 1H), 8.14 (d, J=9.0 Hz, 2H), 8.54 (d, J=1.5 Hz, 1H).

(E)-3-(1-(4-Methoxyphenylsulfonyl)-1H-pyrrolo[2,3-b]pyridin-5-yl)acrylic acid (13b)

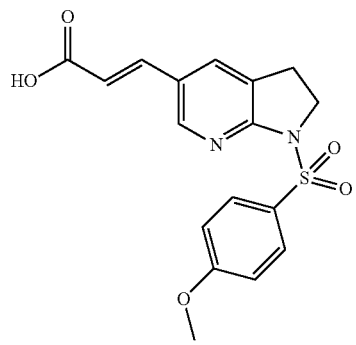 [SMILES: COc1ccc(S(=O)(=O)N2CCc3cc(/C=C/C(=O)O)cnc32)cc1]

A mixture of 12b (0.58 g, 1.40 mmol) and trifluoroacetic acid (4.67 ml) was stirred at room temperature for 1 hour. The reaction mixture was added water to precipitate a white product, which was collected by filtration to afford 13b (0.49 g, 97.66%). $^1$H-NMR (500 MHz, CD$_3$OD): δ 3.82 (s, 3H), 6.57 (d, J=16.0 Hz, 1H), 6.73 (d, J=4.0 Hz, 1H), 7.03 (t, J=9.0 Hz, 2H), 7.76 (d, J=16.0 Hz, 1H), 7.83 (t, J=4.0 Hz, 1H), 8.08 (d, J=9.0 Hz, 2H), 8.24 (d, J=2.0 Hz, 1H), 8.52 (d, J=2 Hz, 1H).

(E)-N-hydroxy-3-(1-(4-methoxyphenylsulfonyl)-1H-pyrrolo[2,3-b]pyridin-5-yl) acrylamide (14b)

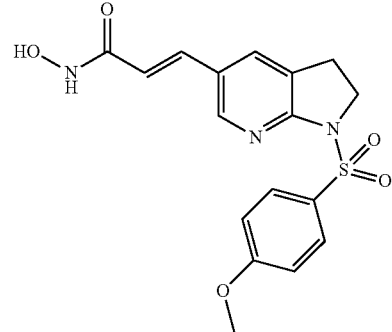 [SMILES: COc1ccc(S(=O)(=O)N2CCc3cc(/C=C/C(=O)NO)cnc32)cc1]

A mixture of 13b (0.44 g, 1.23 mmol), EDC (0.35 g, 1.85 mmol), HOBt (0.20 g, 1.48 mmol), NMM (0.32 ml, 2.95 mmol), and DMF (2 ml) was stirred for 10 minutes, and, after addition of o-(tetrahydro-2H-pyran-2-yl)hydroxylamine (0.17 g, 1.48 mmol) at room temperature, was stirred again overnight. The residue resulting from removal of the solvent was purified with a flash column over silica gel (ethyl acetate:n-hexane=2:1, Rf=0.38). An oily product thus obtained was dissolved in MeOH (5 ml) and 10% TFA (aq.) (5 ml) at room temperature, and stirred overnight. Water was added to precipitate a white solid, which was collected by filtration to afford 14b (0.37 g, 90.91%). m.p. 192.5-193.3. $^1$H-NMR (500 MHz, DMSO-d$_6$): δ 3.78 (s, 3H), 6.52 (d, J=16.0 Hz, 1H), 6.81 (d, J=4.0 Hz, 1H), 7.10 (t, J=9.0 Hz, 2H), 7.54 (d, J=16.0 Hz, 1H), 7.89 (t, J=4.0 Hz, 1H), 8.03 (d, J=9.0 Hz, 2H), 8.23 (d, J=1.5 Hz, 1H), 8.55 (d, J=1.5 Hz, 1H).

5-Bromo-1-(3-methoxyphenylsulfonyl)-1H-pyrrolo[2,3-b]pyridine (11c)

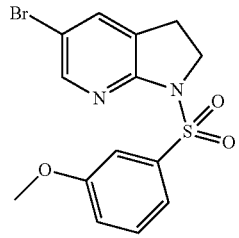 [SMILES: COc1cccc(S(=O)(=O)N2CCc3cc(Br)cnc32)c1]

A mixture of 5-bromo-7-azaindole (0.35 g, 1.78 mmol), DMF (2 ml), and 60% NaH (0.06 g, 2.67 mmol) was stirred for 10 minutes, and, after addition of 3-methoxybenzenesulfonyl chloride (0.38 ml, 2.67 mmol), was stirred again overnight at room temperature. Water was added to precipitate a white product, which was collected by filtration to afford 11c (0.57 g, 87.20%). $^1$H-NMR (500 MHz, CDCl$_3$): δ 3.84 (s, 3H), 6.55 (d, J=4.0 Hz, 1H), 7.09-7.11 (m, 1H), 7.37 (t, J=8.0 Hz, 1H), 7.69-7.75 (m, 3H), 7.98 (d, J=2.0 Hz, 1H), 8.46 (d, J=2.0 Hz, 1H).

(E)-tert-Butyl 3-(1-(3-methoxyphenylsulfonyl)-1H-pyrrolo[2,3-b]pyridin-5-yl) acrylate (12c)

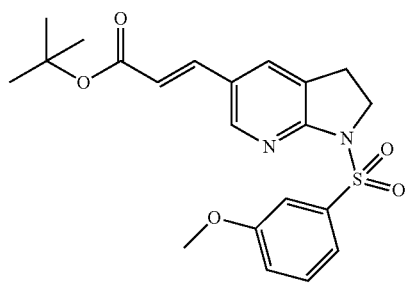 [SMILES: COc1cccc(S(=O)(=O)N2CCc3cc(/C=C/C(=O)OC(C)(C)C)cnc32)c1]

A mixture of 11c (0.60 g, 1.63 mmol), palladium acetate (0.04 g, 0.16 mmol), triphenylphosphine (0.09 g, 0.33 mmol), triethylamine (0.23 ml, 1.63 mmol), sodium bicarbonate (0.27 g, 3.26 mmol), and DMF (2 ml) was stirred for 10 minutes, and, after addition of t-butyl acrylate (0.29 ml, 1.96 mmol) at 120° C., was stirred again overnight. The residue resulting from removal of the solvent was purified with a flash column over silica gel (ethyl acetate:n-hexane=1:4, Rf=0.38) to afford 12c (0.49 g, 72.53%) as a yellow solid. $^1$H-NMR (500 MHz, CDCl$_3$): δ 1.54 (s, 9H), 3.84 (s, 3H), 6.40 (d, J=16.0 Hz, 1H), 6.60 (d, J=4.0 Hz, 1H), 7.09 (t, J=8.5 Hz, 1H), 7.37 (t, J=8.5 Hz, 1H), 7.64 (d, J=16.0 Hz, 1H), 7.71-7.78 (m, 2H), 7.78 (s, 1H), 7.98 (d, J=2.0 Hz, 1H), 8.56 (d, J=2.0 Hz, 1H).

(E)-3-(1-(3-Methoxyphenylsulfonyl)-1H-pyrrolo[2,3-b]pyridin-5-yl)acrylic acid (13c)

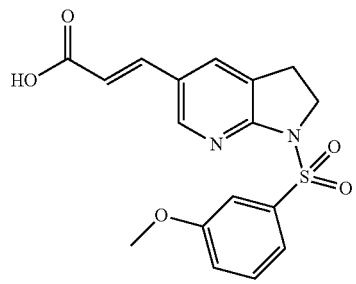 [SMILES: COc1cccc(S(=O)(=O)N2CCc3cc(/C=C/C(=O)O)cnc32)c1]

A mixture of 12c (0.49 g, 1.18 mmol) and trifluoroacetic acid (3.93 ml) and stirred at room temperature for 1 hour. The reaction mixture was added water to precipitate a white product, which was collected by filtration to afford 13c (0.39 g, 92.23%). $^1$H-NMR (500 MHz, CD$_3$OD+DMSO-d$_6$): δ 3.86 (s, 3H), 6.62 (d, J=16.0 Hz, 1H), 6.81 (d, J=4.0 Hz, 1H), 7.23 (t, J=8.5 Hz, 1H), 7.48 (d, J=8.0 Hz, 1H), 7.69-7.74 (m, 2H), 7.78 (d, J=16.0 Hz, 1H), 7.89 (d, J=4.0 Hz, 1H), 8.31 (d, J=2.0 Hz, 1H), 8.60 (d, J=2.5 Hz, 1H).

(E)-N-hydroxy-3-(1-(3-methoxyphenylsulfonyl)-1H-pyrrolo[2,3-b]pyridin-5-yl) acrylamide (14c)

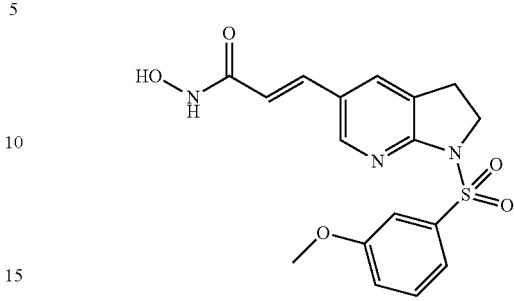

A mixture of 13c (0.39 g, 1.09 mmol), EDC (0.31 g, 1.64 mmol), HOBt (0.18 g, 1.31 mmol), NMM (0.29 ml, 2.62 mmol), and DMF (2 ml) was stirred for 10 minutes, and, after addition of o-(tetrahydro-2H-pyran-2-yl)hydroxylamine (0.15 g, 1.31 mmol) at room temperature, was stirred again overnight. The residue resulting from removal of the solvent was purified with a flash column over silica gel (ethyl acetate:n-hexane=2:1, Rf=0.50). An oily product thus obtained was dissolved in MeOH (5 ml) and 10% TFA (aq.) (5 ml) at room temperature, and stirred overnight. Water was added to precipitate a white product, which was collected by filtration to afford 14c (0.30 g, 83.69%). m.p. 207.3-208.3. $^1$H-NMR (500 MHz, DMSO-d$_6$): δ 3.78 (s, 3H), 6.53 (d, J=15.5 Hz, 1H), 6.84 (d, J=3.5 Hz, 1H), 7.26 (dd, J=2.0, 7.0 Hz, 1H), 7.50-7.56 (m, 2H), 7.61-7.64 (m, 2H), 7.92 (d, J=4.0 Hz, 1H), 8.25 (d, J=1.5 Hz, 1H), 8.59 (d, J=1.5 Hz, 1H).

5-Bromo-1-(3,4-dimethoxyphenylsulfonyl)-1H-pyrrolo[2,3-b]pyridine (11d)

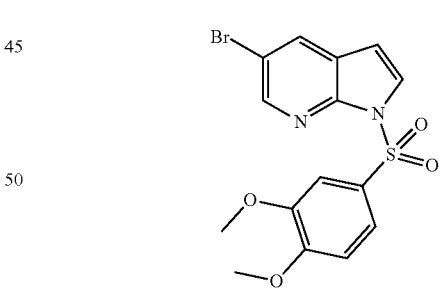

A mixture of 5-bromo-7-azaindole (0.35 g, 1.78 mmol), DMF (2 ml), and 60% NaH (0.06 g, 2.67 mmol) was stirred for 10 minutes, and after addition of 3,4-dimethoxybenzenesulfonyl chloride (0.63 g, 2.67 mmol), was stirred again overnight at room temperature. Water was added to precipitate a white product, which was collected by filtration to afford 11d (0.58 g, 82.03%). $^1$H-NMR (500 MHz, CDCl$_3$): δ 3.89 (s, 3H), 3.92 (s, 3H), 6.52 (d, J=4.0 Hz, 1H), 6.88 (d, J=8.5 Hz, 1H), 7.71-7.73 (m, 2H), 7.76 (t, J=8.5 Hz, 1H), 7.79-8.01 (m, 1H), 8.44 (d, J=2.0 Hz, 1H).

(E)-tert-Butyl 3-(1-(3,4-dimethoxyphenylsulfonyl)-
1H-pyrrolo[2,3-b]pyridin-5-yl) acrylate (12d)

(E)-3-(1-(3,4-Dimethoxyphenylsulfonyl)-1H-pyrrolo
[2,3-b]pyridin-5-yl)-N-hydroxyacrylamide (14d)

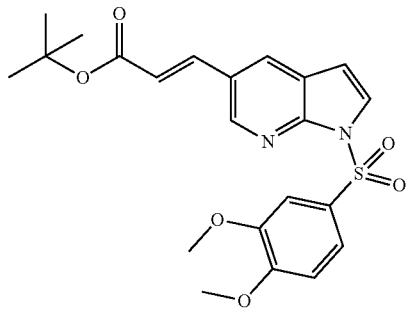 [SMILES: COc1ccc(S(=O)(=O)n2ccc3cc(/C=C/C(=O)OC(C)(C)C)cnc32)cc1OC]

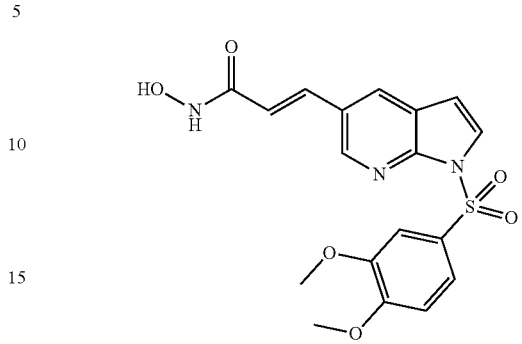

A mixture of 11d (0.58 g, 1.46 mmol), palladium acetate (0.03 g, 0.15 mmol), triphenylphosphine (0.08 g, 0.29 mmol), triethylamine (0.20 ml, 1.46 mmol), sodium bicarbonate (0.25 g, 2.92 mmol), and DMF (2 ml) was stirred for 10 minutes, and, after addition of t-butyl acrylate (0.25 ml, 1.75 mmol) at 120° C., was stirred again overnight. The residue resulting from removal of the solvent was purified with a flash column over silica gel (ethyl acetate:n-hexane=1:4, Rf=0.10) to afford 12d (0.60 g, 92.45%) as a yellow solid. $^1$H-NMR (500 MHz, CDCl$_3$): δ 1.54 (s, 9H), 3.89 (s, 3H), 3.93 (s, 3H), 6.40 (d, J=16.0 Hz, 1H), 6.59 (d, J=4.0 Hz, 1H), 6.89 (t, J=8.5 Hz, 1H), 7.64 (d, J=16.0 Hz, 1H), 7.73 (t, J=4.0 Hz, 1H), 7.78-7.80 (m, 2H), 7.98 (d, J=1.5 Hz, 1H), 8.55 (d, J=1.5 Hz, 1H).

A mixture of 13d (0.64 g, 1.65 mmol), EDC (0.48 g, 2.48 mmol), HOBt (0.27 g, 1.98 mmol), NMM (0.44 ml, 3.96 mmol), and DMF (2.5 ml) was stirred for 10 minutes, and, after addition of o-(tetrahydro-2H-pyran-2-yl)hydroxylamine (0.23 g, 1.98 mmol) at room temperature, was stirred again overnight. The residue resulting from removal of the solvent was purified with a flash column over silica gel (ethyl acetate:n-hexane=2:1, Rf=0.43).

An oily product thus obtained was dissolved in MeOH (6 ml) and 10% TFA (aq.) (6 ml) at room temperature, was stirred again overnight. Water was added to precipitate a white solid, which was collected by filtration to afford 14d (0.37 g, 63.85%). m.p. 212.3-213.5. $^1$H-NMR (500 MHz, DMSO-d$_6$): δ 3.78 (s, 3H), 3.79 (s, 3H), 6.53 (d, J=15.5 Hz, 1H), 6.80 (d, J=4.0 Hz, 1H), 7.12 (t, J=8.5 Hz, 1H), 7.54 (d, J=15.5 Hz, 1H), 7.64 (d, J=2.0 Hz, 1H), 7.69 (d, J=8.5 Hz, 1H), 7.89 (d, J=4.0 Hz, 1H), 8.23 (d, J=1.5 Hz, 1H), 8.59 (d, J=1.5 Hz, 1H).

(E)-3-(1-(3,4-Dimethoxyphenylsulfonyl)-1H-pyrrolo
[2,3-b]pyridin-5-yl)acrylic acid (13d)

5-Bromo-1-(4-fluorophenylsulfonyl)-1H-pyrrolo[2,
3-b]pyridine (11e)

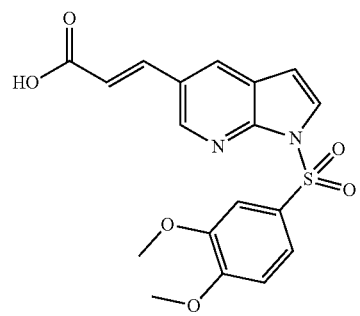 [SMILES: COc1ccc(S(=O)(=O)n2ccc3cc(/C=C/C(=O)O)cnc32)cc1OC]

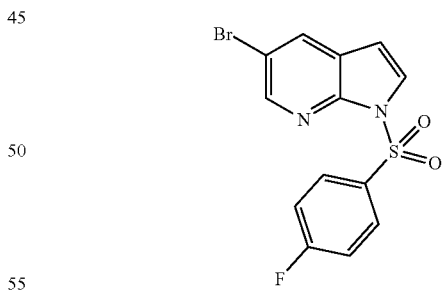

A mixture of 12c (0.60 g, 1.35 mmol) and trifluoroacetic acid (4.5 ml) was stirred at room temperature for 1 hour. The reaction mixture was added water to precipitate a white product, which was collected by filtration to afford 13c (0.48 g, 91.55%). $^1$H-NMR (500 MHz, CD$_3$OD+DMSO-d$_6$): δ 3.85 (s, 3H), 3.87 (s, 3H), 6.60 (d, J=16.0 Hz, 1H), 6.77 (d, J=4.0 Hz, 1H), 7.08 (t, J=9.0 Hz, 1H), 7.74-7.75 (m, 2H), 7.78 (d, J=16.0 Hz, 1H), 7.86 (d, J=4.0 Hz, 1H), 8.29 (d, J=2.0 Hz, 1H), 8.58 (d, J=2.0 Hz, 1H).

A mixture of 5-bromo-7-azaindole (0.35 g, 1.78 mmol), DMF (2 ml), and 60% NaH (0.06 g, 2.67 mmol) was stirred for 10 minutes, and, after addition of 4-fluorobenzenesulfonyl chloride (0.52 g, 2.67 mmol), was stirred again overnight at room temperature. Water was added to precipitate a white product, which was collected by filtration to afford 11e (0.59 g, 93.32%). $^1$H-NMR (500 MHz, CDCl$_3$): δ 6.55 (d, J=4.0 Hz, 1H), 7.17 (t, J=9.0 Hz, 2H), 7.72 (t, J=4.0 Hz, 1H), 7.99 (d, J=2.5 Hz, 1H), 8.21-8.23 (m, 2H), 8.44 (d, J=2.0 Hz, 1H).

91

(E)-tert-Butyl 3-(1-(4-fluorophenylsulfonyl)-1H-pyrrolo[2,3-b]pyridin-5-yl)acrylate (12e)

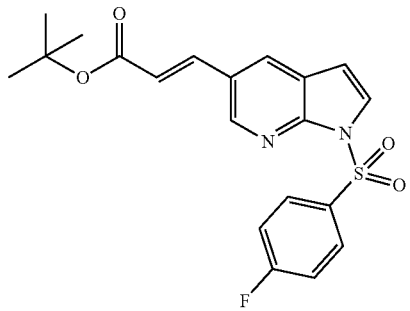 [SMILES: CC(C)(C)OC(=O)/C=C/c1cnc2c(ccn2S(=O)(=O)c2ccc(F)cc2)c1]

A mixture of 11e (0.59 g, 1.66 mmol), palladium acetate (0.04 g, 0.17 mmol), triphenylphosphine (0.09 g, 0.33 mmol), triethylamine (0.23 ml, 1.66 mmol), sodium bicarbonate (0.28 g, 3.32 mmol), and DMF (2 ml) was stirred for 10 minutes, and, after addition of t-butyl acrylate (0.29 ml, 1.99 mmol) at 120° C., was stirred again overnight. The residue resulting from removal of the solvent was purified with a flash column over silica gel (ethyl acetate:n-hexane=1:4, Rf=0.28) to afford 12e (0.44 g, 65.86%) as a yellow solid. $^1$H-NMR (500 MHz, CDCl$_3$): δ 1.54 (s, 9H), 6.40 (d, J=16.0 Hz, 1H), 6.61 (d, J=4.0 Hz, 1H), 7.17 (t, J=8.5 Hz, 2H), 7.64 (d, J=16.0 Hz, 1H), 7.73 (t, J=4.0 Hz, 1H), 7.98 (d, J=2.0 Hz, 1H), 8.25 (dd, J=5.0, 9.0 Hz, 2H), 8.54 (d, J=1.5 Hz, 1H).

(E)-3-(1-(4-Fluorophenylsulfonyl)-1H-pyrrolo[2,3-b]pyridin-5-yl)acrylic acid (13e)

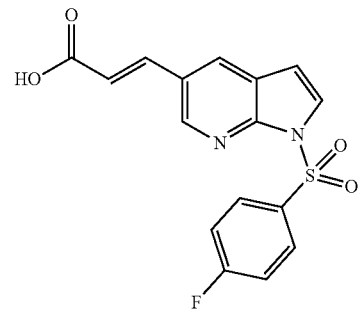

A mixture of 12e (0.47 g, 1.06 mmol) and trifluoroacetic acid (4.24 ml, 4.24 mmol) was stirred at room temperature for 2 hours. The reaction mixture was added water to precipitate a white product, which was collected by filtration to afford 13e (0.42 g, 95.84%). $^1$H-NMR (500 MHz, CD$_3$OD): δ 6.58 (d, J=16.0 Hz, 1H), 6.77 (d, J=3.5 Hz, 1H), 7.29 (t, J=8.5 Hz, 2H), 7.76 (d, J=16.0 Hz, 1H), 7.85 (t, J=4.0 Hz, 1H), 8.22-8.25 (m, 2H), 8.26 (s, 1H), 8.53 (d, J=2.0 Hz, 1H).

92

(E)-3-(1-(4-Fluorophenylsulfonyl)-1H-pyrrolo[2,3-b]pyridin-5-yl)-N-hydroxy-acrylamide (14e)

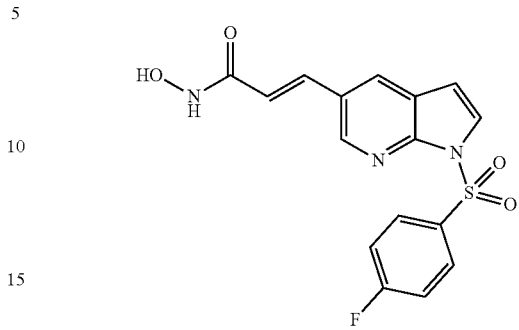

A mixture of 13e (0.36 g, 1.04 mmol), EDC (0.30 g, 1.56 mmol), HOBt (0.17 g, 1.25 mmol), NMM (0.27 ml, 2.50 mmol), and DMF (2 ml) was stirred for 10 minutes, and, after addition of o-(tetrahydro-2H-pyran-2-yl)hydroxylamine (0.15 g, 1.25 mmol) at room temperature, was stirred again overnight. The residue resulting from removal of the solvent was purified with a flash column over silica gel (ethyl acetate:n-hexane=2:1, Rf=0.63). An oily product thus obtained was dissolved in MeOH (4 ml) and 10% TFA (aq.) (4 ml) at room temperature, and stirred overnight. Water was added to precipitate a white solid, which was collected by filtration to afford 14e (0.26 g, 86.69%). m.p. 213.6-214.5. $^1$H-NMR (500 MHz, DMSO-d$_6$): δ 6.52 (d, J=15.5 Hz, 1H), 6.86 (d, J=4.0 Hz, 1H), 7.47 (t, J=9.0 Hz, 2H), 7.55 (d, J=15.5 Hz, 1H), 7.93 (d, J=4.0 Hz, 1H), 8.18-8.21 (m, 2H), 8.25 (s, 1H), 8.56 (s, 1H).

5-Bromo-1-(4-chlorophenylsulfonyl)-1H-pyrrolo[2,3-b]pyridine (11f)

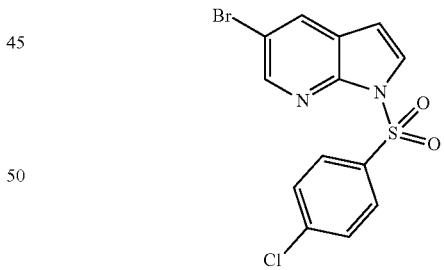

A mixture of 5-bromo-7-azaindole (0.35 g, 1.78 mmol), DMF (2 ml), and 60% NaH (0.06 g, 2.67 mmol) was stirred for 10 minutes, and, after addition of 4-chlorobenzenesulfonyl chloride (0.56 g, 2.67 mmol), was stirred again overnight at room temperature. Water was added to precipitate a white product, which was collected by filtration to afford 11f (0.55 g, 83.14%). $^1$H-NMR (500 MHz, CDCl$_3$): δ 6.56 (d, J=3.5 Hz, 1H), 7.46 (t, J=8.5 Hz, 2H), 7.71 (t, J=4.0 Hz, 1H), 7.98 (d, J=2.5 Hz, 1H), 8.12 (d, J=8.5 Hz, 2H), 8.44 (d, J=2.0 Hz, 1H).

93

(E)-tert-Butyl 3-(1-(4-chlorophenylsulfonyl)-1H-pyrrolo[2,3-b]pyridin-5-yl)acrylate (12f)

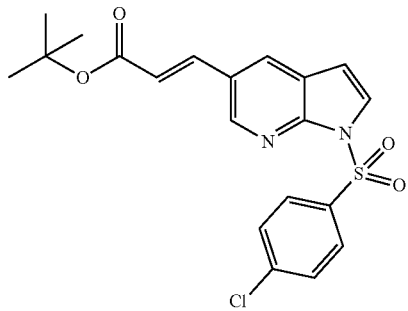 [SMILES: CC(C)(C)OC(=O)/C=C/c1cnc2c(ccn2S(=O)(=O)c2ccc(Cl)cc2)c1]

A mixture of 11f (0.49 g, 1.32 mmol), palladium acetate (0.03 g, 0.13 mmol), triphenylphosphine (0.07 g, 0.26 mmol), triethylamine (0.18 ml, 1.32 mmol), sodium bicarbonate (0.22 g, 2.64 mmol), and DMF (1.5 ml) was stirred for 10 minutes, and, after addition of t-butyl acrylate (0.23 ml, 1.58 mmol) at 120° C., was stirred again overnight. The residue resulting from removal of the solvent was purified with a flash column over silica gel (ethyl acetate:n-hexane=1:4, Rf=0.35) to afford 12f (0.38 g, 68.72%) as a yellow solid. $^1$H-NMR (500 MHz, CDCl$_3$): δ 1.54 (s, 9H), 6.40 (d, J=16.0 Hz, 1H), 6.62 (d, J=3.5 Hz, 1H), 7.47 (t, J=9.0 Hz, 2H), 7.64 (d, J=16.0 Hz, 1H), 7.72 (t, J=4.0 Hz, 1H), 7.98 (d, J=2.0 Hz, 1H), 8.15 (d, J=8.5 Hz, 2H), 8.54 (d, J=1.5 Hz, 1H).

(E)-3-(1-(4-Chlorophenylsulfonyl)-1H-pyrrolo[2,3-b]pyridin-5-yl)acrylic acid (13f)

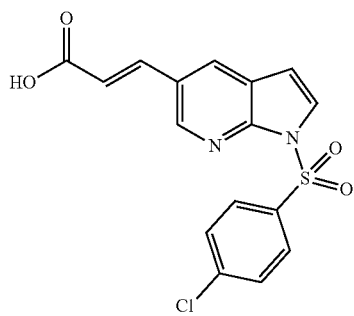 [SMILES: O=C(O)/C=C/c1cnc2c(ccn2S(=O)(=O)c2ccc(Cl)cc2)c1]

A mixture of 12f (0.54 g, 1.29 mmol) and trifluoroacetic acid (4.3 ml) was stirred at room temperature for 1 hour. The reaction mixture was added water to precipitate a white product, which was collected by filtration to afford 13f (0.43 g, 91.88%). $^1$H-NMR (500 MHz, DMSO-d$_6$): δ 6.63 (d, J=16.0 Hz, 1H), 6.86 (d, J=4.0 Hz, 1H), 7.67-7.74 (m, 3H), 7.94 (t, J=4.0 Hz, 1H), 8.11 (d, J=8.5 Hz, 2H), 8.41 (d, J=1.5 Hz, 1H), 8.65 (d, J=2.0 Hz, 1H).

94

(E)-3-(1-(4-Chlorophenylsulfonyl)-1H-pyrrolo[2,3-b]pyridin-5-yl)-N-hydroxy-acrylamide (14f)

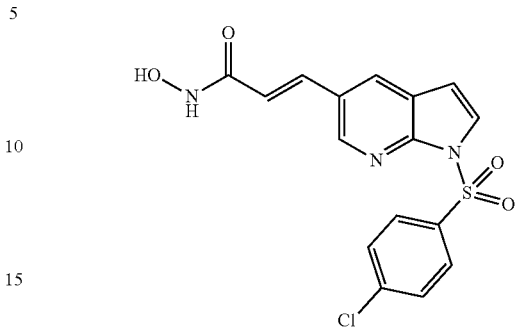

A mixture of 13f (0.42 g, 1.16 mmol), EDC (0.33 g, 1.74 mmol), HOBt (0.19 g, 1.39 mmol), NMM (0.31 ml, 2.78 mmol), and DMF (2 ml) was stirred for 10 minutes, and, after addition of o-(tetrahydro-2H-pyran-2-yl)hydroxylamine (0.16 g, 1.39 mmol) at room temperature, was stirred again overnight. The residue resulting from removal of the solvent was purified with a flash column over silica gel (ethyl acetate:n-hexane=2:1, Rf=0.44). An oily product thus obtained was dissolved in MeOH (5 ml) and 10% TFA (aq.) (5 ml) at room temperature, and stirred overnight. Water was added to precipitate a white solid, which was collected by filtration to afford 14f (0.34 g, 86.53%). m.p. 210.4-211.5. $^1$H-NMR (500 MHz, DMSO-d$_6$): δ 6.52 (d, J=16.0 Hz, 1H), 6.87 (d, J=4.0 Hz, 1H), 7.56 (d, J=16.0 Hz, 1H), 7.70 (t, J=8.5 Hz, 2H), 7.93 (d, J=4.0 Hz, 1H), 8.12 (d, J=8.5 Hz, 2H), 8.25 (s, 1H), 8.56 (s, 1H).

5-bromo-1-(4-bromophenylsulfonyl)-1H-pyrrolo[2,3-b]pyridine (11g)

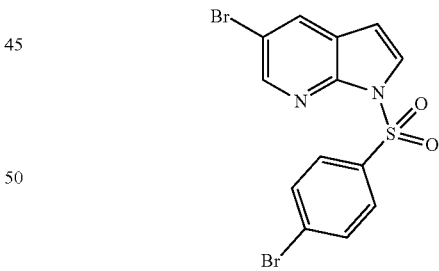

A mixture of 5-bromo-7-azaindole (0.35 g, 1.78 mmol), DMF (2 ml), and 60% NaH (0.06 g, 2.67 mmol) was stirred for 10 minutes, and, after addition of 4-bromobenzenesulfonyl chloride (0.68 g, 2.67 mmol), was stirred again overnight at room temperature. Water was added to precipitate a yellow product, which was collected by filtration to afford 11g (0.60 g, 81.20%). $^1$H-NMR (500 MHz, CDCl$_3$): δ 6.56 (d, J=4.0 Hz, 1H), 7.64 (t, J=9.0 Hz, 2H), 7.71 (t, J=4.0 Hz, 1H), 7.99 (s, 1H), 8.04 (d, J=9.0 Hz, 2H), 8.44 (d, J=2.0 Hz, 1H).

(E)-tert-Butyl 3-(4-(5-((E)-3-tert-butoxy-3-oxoprop-1-enyl)-1H-pyrrolo[2,3-b]pyridin-1-ylsulfonyl)phenyl)acrylate (12g)

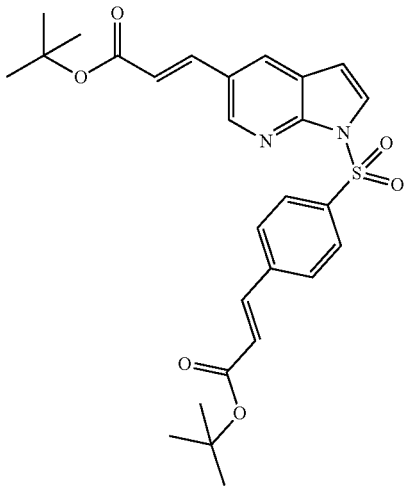 [SMILES: CC(C)(C)OC(=O)/C=C/c1ccc(S(=O)(=O)n2ccc3cc(/C=C/C(=O)OC(C)(C)C)cnc32)cc1]

A mixture of 11g (0.60 g, 1.45 mmol), palladium acetate (0.06 g, 0.30 mmol), triphenylphosphine (0.16 g, 0.58 mmol), triethylamine (0.40 ml, 2.90 mmol), sodium bicarbonate (0.48 g, 5.80 mmol), and DMF (3 ml) was stirred for 10 minutes, and, after addition of t-butyl acrylate (0.50 ml, 3.48 mmol) at 120° C., was stirred again overnight. The residue resulting from removal of the solvent was purified with a flash column over silica gel (ethyl acetate:n-hexane=1:4, Rf=0.50) to afford 12g (0.71 g, 95.90%) as a yellow solid. $^1$H-NMR (500 MHz, CDCl$_3$): δ 1.51 (s, 9H), 1.53 (s, 9H), 6.40 (d, J=16.0 Hz, 1H), 6.41 (d, J=16.0 Hz, 1H), 6.62 (d, J=4.0 Hz, 1H), 7.51 (d, J=16.0 Hz, 1H), 7.59 (t, J=8.5 Hz, 2H), 7.63 (d, J=16.0 Hz, 1H), 7.74 (t, J=4.0 Hz, 1H), 7.98 (d, J=2.0 Hz, 1H), 8.19 (d, J=8.5 Hz, 2H), 8.54 (d, J=2.0 Hz, 1H).

(E)-3-(4-(5-((E)-2-Carboxyvinyl)-1H-pyrrolo[2,3-b]pyridin-1-ylsulfonyl)phenyl) acrylic acid (13g)

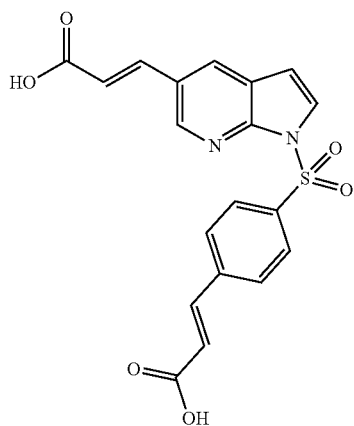 [SMILES: O=C(O)/C=C/c1ccc(S(=O)(=O)n2ccc3cc(/C=C/C(=O)O)cnc32)cc1]

A mixture of 12g (0.71 g, 1.39 mmol) and trifluoroacetic acid (4.63 ml) was stirred at room temperature for 1 hour. Water was added to precipitate a yellow solid, which was collected by filtration to afford 13g (0.51 g, 92.09%). $^1$H-NMR (500 MHz, DMSO-d$_6$): δ 6.63 (d, J=16.0 Hz, 1H), 6.65 (d, J=16.0 Hz, 1H), 6.85 (d, J=4.0 Hz, 1H), 7.57 (d, J=15.5 Hz, 1H), 7.68 (d, J=16.0 Hz, 1H), 7.91 (d, J=8.5 Hz, 2H), 7.96 (d, J=4.0 Hz, 1H), 8.10 (d, J=8.5 Hz, 2H), 8.41 (d, J=2.0 Hz, 1H), 8.67 (d, J=1.5 Hz, 1H).

(E)-N-hydroxy-3-(4-(5-((E)-3-(hydroxyamino)-3-oxoprop-1-enyl)-1H-pyrrolo[2,3-b]pyridin-1-ylsulfonyl)phenyl)acrylamide (14g)

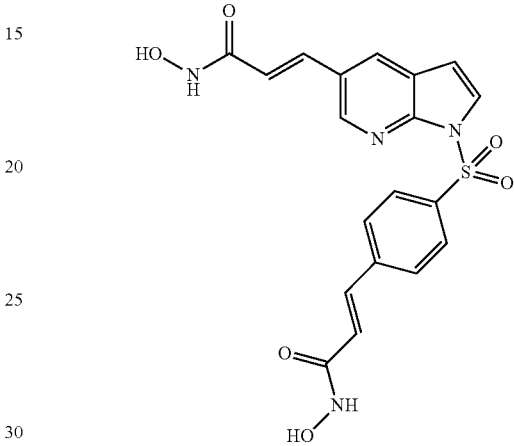

A mixture of 13g (0.48 g, 1.20 mmol), EDC (0.69 g, 3.60 mmol), HOBt (0.39 g, 2.88 mmol), NMM (0.63 ml, 5.76 mmol), and DMF (3 ml) was stirred for 10 minutes, and, after addition of o-(tetrahydro-2H-pyran-2-yl)hydroxylamine (0.34 g, 2.88 mmol) at room temperature, was stirred again overnight. The residue resulting from removal of the solvent was purified with a flash column over silica gel (ethyl acetate:n-hexane=4:1, Rf=0.48). An oily product thus obtained was dissolved in MeOH (2 ml) and 10% TFA (aq.) (2 ml) at room temperature, and stirred overnight. Water was added to precipitate a pale yellow solid, which was collected by filtration to afford 14g (0.05 g, 38.90%). m.p. 188.7-190.5 (decomp.). $^1$H-NMR (500 MHz, DMSO-d$_6$): δ 6.54 (t, J=16.0 Hz, 2H), 6.86 (d, J=4.0 Hz, 1H), 7.44 (d, J=15.5 Hz, 1H), 7.54 (d, J=15.5 Hz, 1H), 7.77 (d, J=8.5 Hz, 2H), 7.93 (d, J=4.0 Hz, 1H), 8.10 (d, J=8.5 Hz, 2H), 8.25 (s, 1H), 8.56 (s, 1H).

5-Bromo-1-(3-bromophenylsulfonyl)-1H-pyrrolo[2,3-b]pyridine (11h)

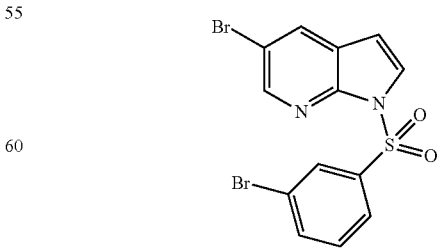

A mixture of 5-bromo-7-azaindole (0.35 g, 1.78 mmol), DMF (2 ml), and 60% NaH (0.06 g, 2.67 mmol) was stirred for 10 minutes, and, after addition of 3-bromobenzenesulfonyl chloride (0.68 g, 2.67 mmol), was stirred again overnight at room temperature. Water was added to precipitate a white product, which was collected by filtration to afford 11h (0.63 g, 85.26%). $^1$H-NMR (500 MHz, CDCl$_3$): δ 6.57 (d, J=3.5 Hz, 1H), 7.38 (t, J=8.0 Hz, 1H), 7.71 (d, J=4.5 Hz, 2H), 7.99 (d, J=2.0 Hz, 1H), 8.13 (d, J=8.0 Hz, 1H), 8.33 (s, 1H), 8.46 (d, J=2.0 Hz, 1H).

(E)-tert-Butyl 3-(3-(5-((E)-3-tert-butoxy-3-oxoprop-1-enyl)-1H-pyrrolo[2,3-b]pyridin-1-ylsulfonyl)phenyl)acrylate (12h)

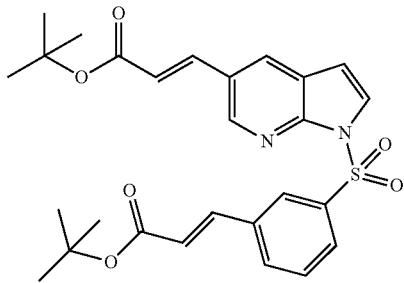 [SMILES: CC(C)(C)OC(=O)/C=C/c1cccc(S(=O)(=O)n2ccc3cc(/C=C/C(=O)OC(C)(C)C)cnc32)c1]

A mixture of 11h (0.63 g, 1.52 mmol), palladium acetate (0.06 g, 0.30 mmol), triphenylphosphine (0.16 g, 0.60 mmol), triethylamine (0.42 ml, 3.04 mmol), sodium bicarbonate (0.52 g, 6.08 mmol), and DMF (3 ml) was stirred for 10 minutes, and, after addition of t-butyl acrylate (0.54 ml, 3.64 mmol) at 120° C., was stirred again overnight. The residue resulting from removal of the solvent was purified with a flash column over silica gel (ethyl acetate:n-hexane=1:4, Rf=0.40) to afford 12h (0.70 g, 90.19%) as a yellow solid. $^1$H-NMR (500 MHz, CDCl$_3$): δ 1.53 (s, 9H), 1.54 (s, 9H), 6.40 (d, J=15.5 Hz, 1H), 6.45 (d, J=16.0 Hz, 1H), 6.62 (d, J=4.0 Hz, 1H), 7.49-7.69 (m, 4H), 7.75 (t, J=4.0 Hz, 1H), 7.98 (d, J=2.0 Hz, 1H), 8.16-8.34 (m, 1H), 8.36 (d, J=1.5 Hz, 1H), 8.56 (d, J=2.0 Hz, 1H).

(E)-3-(3-(5-((E)-2-Carboxyvinyl)-1H-pyrrolo[2,3-b]pyridin-1-ylsulfonyl)phenyl) acrylic acid (13h)

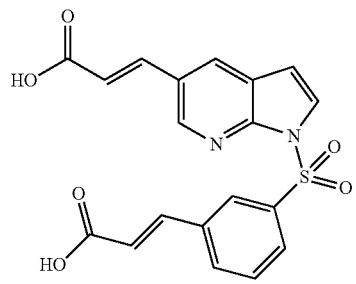 [SMILES: O=C(O)/C=C/c1cccc(S(=O)(=O)n2ccc3cc(/C=C/C(=O)O)cnc32)c1]

A mixture of 12h (0.70 g, 1.37 mmol) and trifluoroacetic acid (4.57 ml) was stirred at room temperature for 1 hour. Water was added to precipitate a yellow product, which was collected by filtration to afford 13h (0.53 g, 97.10 %). $^1$H-NMR (500 MHz, CD$_3$OD+DMSO-d$_6$): δ 6.62 (d, J=16.0 Hz, 2H), 6.83 (d, J=4.0 Hz, 1H), 7.63 (d, J=8.0 Hz, 1H), 7.69 (d, J=16.0 Hz, 1H), 7.77 (d, J=16.0 Hz, 1H), 7.94 (d, J=4.0 Hz, 2H), 8.18 (d, J=8.0 Hz, 1H), 8.31 (d, J=2.0 Hz, 1H), 8.42 (s, 1H), 8.60 (d, J=2.0 Hz, 1H).

(E)-N-hydroxy-3-(3-(5-((E)-3-(hydroxyamino)-3-oxoprop-1-enyl)-1H-pyrrolo[2,3-b]pyridin-1-ylsulfonyl)phenyl)acrylamide (14h)

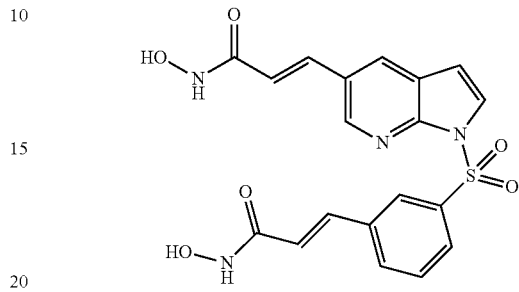

A mixture of 13h (0.57 g, 1.43 mmol), EDC (0.82 g, 4.29 mmol), HOBt (0.46 g, 3.43 mmol), NMM (0.75 ml, 6.86 mmol), and DMF (3.5 ml) was stirred for 10 minutes, and, after addition of o-(tetrahydro-2H-pyran-2-yl)hydroxylamine (0.40 g, 3.43 mmol) at room temperature, was stirred again overnight. The residue resulting from removal of the solvent was purified with a flash column over silica gel (ethyl acetate:n-hexane=4:1, Rf=0.43). An oily product thus obtained was then dissolved in MeOH (3 ml) and 10% TFA (aq.) (3 ml), and stirred at room temperature overnight. Water was added to precipitate a pale yellow solid, which was collected by filtration to afford 14h (0.13 g, 67.43%). m.p. 219.4-221.3 (decomp.). $^1$H-NMR (500 MHz, DMSO-d$_6$): δ 6.52 (t, J=15.5 Hz, 1H), 6.59 (d, J=16.0 Hz, 1H), 6.87 (d, J=4.0 Hz, 1H), 7.50 (d, J=16.0 Hz, 1H), 7.55 (d, J=15.5 Hz, 1H), 7.64 (t, J=8.5 Hz, 1H), 7.89 (d, J=8.0 Hz, 1H), 7.94 (d, J=4.0 Hz, 1H), 8.05 (d, J=8.0 Hz, 1H), 8.25 (s, 1H), 8.34 (s, 1H), 8.59 (s, 1H).

5-Bromo-1-(2-bromophenylsulfonyl)-1H-pyrrolo[2,3-b]pyridine (11i)

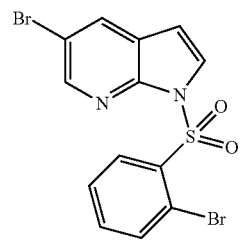 [SMILES: O=S(=O)(c1ccccc1Br)n1ccc2cc(Br)cnc21]

A mixture of 5-bromo-7-azaindole (0.35 g, 1.78 mmol), DMF (2 ml), and 60% NaH (0.06 g, 2.67 mmol) was stirred for 10 minutes, and, after addition of 2-bromobenzenesulfonyl chloride (0.68 g, 2.67 mmol), was stirred again overnight at room temperature. Water was added to precipitate a yellow product, which was collected by filtration to afford 11i (0.66 g, 89.32%). $^1$H-NMR (500 MHz, CDCl$_3$): δ 6.57 (d, J=4.0 Hz, 1H), 7.44 (t, J=8.0 Hz, 1H), 7.57 (t, J=8.0 Hz, 1H), 7.63 (d, J=8.0, 1H), 7.96 (d, J=4.0 Hz, 1H), 7.99 (d, J=2.0 Hz, 1H), 8.25 (d, J=1.5 Hz, 1H), 8.61 (d, J=8.0 Hz, 1H).

(E)-tert-Butyl 3-(2-(5-((E)-3-tert-butoxy-3-oxoprop-1-enyl)-1H-pyrrolo[2,3-b]pyridin-1-ylsulfonyl)phenyl)acrylate (12i)

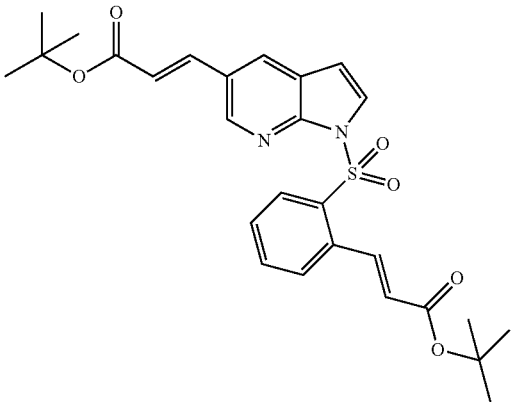 [SMILES: CC(C)(C)OC(=O)/C=C/c1cnc2c(ccn2S(=O)(=O)c2ccccc2/C=C/C(=O)OC(C)(C)C)c1]

A mixture of 11i (0.98 g, 2.36 mmol), Pd$_2$(dba)$_3$ (0.43 g, 0.47 mmol), [(t-Bu)$_3$PH]BF$_4$ (0.27 g, 0.94 mmol), triethylamine (0.66 ml, 4.72 mmol), sodium bicarbonate (0.79 g, 9.44 mmol), and DMF (2.5 ml) was stirred for 10 minutes, and, after addition of t-butyl acrylate (0.82 ml, 5.66 mmol) at 120° C., was stirred again overnight. The residue resulting from removal of the solvent was purified with a flash column over silica gel (ethyl acetate:n-hexane=1:4, Rf=0.45) to afford 12i (1.17 g, 97.09%) as a yellow solid. $^1$H-NMR (500 MHz, CDCl$_3$): δ 1.52 (s, 9H), 1.56 (s, 9H), 5.99 (d, J=15.5 Hz, 1H), 6.36 (d, J=16.0 Hz, 1H), 6.59 (d, J=4.0 Hz, 1H), 7.49-7.51 (m, 1H), 7.57-7.60 (m, 3H), 7.89 (d, J=4.0 Hz, 1H), 7.95 (s, 1H), 8.29 (d, J=16.0 Hz, 1H), 8.37 (s, 1H), 8.52-8.53 (m, 1H).

(E)-3-(2-(5-((E)-2-Carboxyvinyl)-1H-pyrrolo[2,3-b]pyridin-1-ylsulfonyl)phenyl) acrylic acid (13i)

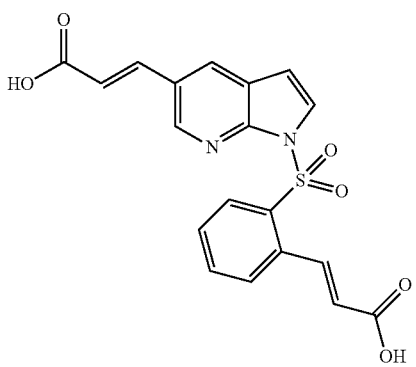 [SMILES: O=C(O)/C=C/c1cnc2c(ccn2S(=O)(=O)c2ccccc2/C=C/C(=O)O)c1]

A mixture of 12i (0.23 g, 0.45 mmol) and trifluoroacetic acid (1.5 ml) was stirred at room temperature for 1 hour. Water was added to precipitate a yellow product, which was collected by filtration to afford 13i (0.15 g, 83.67 %). $^1$H-NMR (500 MHz, CD$_3$OD+DMSO-d$_6$): δ 6.15 (d, J=16.0 Hz, 1H), 6.55 (d, J=16.0 Hz, 1H), 6.76 (d, J=4.0 Hz, 1H), 7.66-7.74 (m, 4H), 7.91 (d, J=4.0 Hz, 1H), 8.26 (s, 1H), 8.39-8.42 (m, 2H), 8.45 (d, J=16.0 Hz, 1H).

(E)-N-hydroxy-3-(2-(5-((E)-3-(hydroxyamino)-3-oxoprop-1-enyl)-1H-pyrrolo[2,3-b]pyridin-1-ylsulfonyl)phenyl)acrylamide (14i)

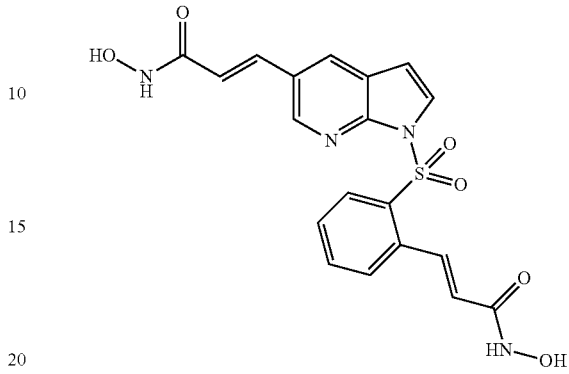

A mixture of 13i (0.90 g, 2.26 mmol), EDC (1.30 g, 6.78 mmol), HOBt (0.74 g, 5.42 mmol), NMM (1.20 ml, 10.84 mmol) and DMF (3 ml) was stirred for 10 minutes, and, after addition of o-(tetrahydro-2H-pyran-2-yl)hydroxylamine (0.64 g, 5.42 mmol) at room temperature, was stirred again overnight. The residue resulting from removal of the solvent was purified with a flash column over silica gel (ethyl acetate:n-hexane=4:1, Rf=0.45). An oily product thus obtained was dissolved in MeOH (8 ml) and 10% TFA (aq.) (8 ml) at room temperature, and stirred overnight. Water was added to precipitate a pale yellow solid, which was collected by filtration to afford 14i (0.38 g, 67.20%). m.p. 159.6-161.9 (decomp.). $^1$H-NMR (500 MHz, DMSO-d$_6$): δ 6.19 (d, J=15.5 Hz, 1H), 6.49 (d, J=5.5 Hz, 1H), 6.84 (d, J=4.0 Hz, 1H), 7.51 (d, J=16.0 Hz, 1H), 7.65-7.70 (m, 2H), 7.76 (t, J=7.0 Hz, 1H), 7.86 (d, J=4.0 Hz, 1H), 8.10 (d, J=15.5 Hz, 1H), 8.24 (s, 1H), 8.27 (d, J=8.0 Hz, 1H), 8.41 (s, 1H).

HDAC Activity Assays

Compounds 1-21, 23, 5a-5p, 6a, 7a, 10a, 14a-14i were subjected to several HDAC activity assays as described below.

More specifically, the IC$_{50}$ values of test compounds were determined by carrying out a fluorimetric histone deacetylase assay following the manufacturer's instructions. For a pan-HDAC assay, HeLa nuclear extracts were used as a source of histone deacetylase (BioVision Inc.). Histone deacetylase isomer inhibition assays were conducted using purified recombinant histone deacetylase proteins of the various isomers (BPS Bioscience Inc.). Reactions were performed in 0.1 mol/L KCl, 20 mmol/L HEPES/NaOH at pH 7.9, 20% glycerol, 0.2 mmol/L DTA, 0.5 mmol/L DTT, and 0.5 mmol/L phenylmethylsulfonylfluoride. Fluor de Lys substrate and test compounds of various concentrations (nmol/L to mol/L) were used at 37° C. in a buffer, containing 25 mmol/L Tris-Cl, pH 8.0, 137 mmol/L NaCl, 2.7 mmol/L KCl, and 1 mmol/L MgCl$_2$. Fluorescence was measured with excitation at a wavelength of 360 nm and emitted light of 460 nm (TECAN ULTRA 384) was detected. Negative (no enzyme, no inhibitor, a drug with no HDAC inhibition activity) and positive controls (a HeLa nuclear extract with no HDAC inhibitor and the known HDAC inhibitor SAHA) were included. Half maximal inhibitory concentrations (IC$_{50}$s) were determined as the test compound concentration that resulted in 50% reduction of HDAC activity increase in control wells during the incubation. Reactions were carried out in triplicate for each test compound. Each point represented the mean±SD of replicates.

Compounds 1-21, 23, 5a-5p, 6a, 7a, 10a, 14a-14i each showed an $IC_{50}$ value less than 6 μM in inhibiting HDAC in the KB cell line (oral carcinoma). Among them, Compounds 5, 6, 7, 12, 5a-5j, 5n-5p, 7a, and 14a-14f each had an $IC_{50}$ value less than 1 μM. Of note, Compound 7 showed inhibition activities in all 10 tested cell lines. See Table 2 below.

TABLE 2

Inhibiting HDAC in human cancer cell lines

| | | $IC_{50}$ (μM) | |
|---|---|---|---|
| Cell lines | Tissue Origin | SAHA | 7 |
| KB | Oral carcinoma | 0.75 ± 0.10 | 0.76 ± 0.23 |
| HSC-3 | Oral carcinoma | 0.71 ± 0.34 | 0.66 ± 0.12 |
| HONE-1 | Nasopharyngeal carcinoma | 1.18 ± 0.04 | 1.20 ± 0.31 |
| H460 | Non-small-cell lung carcinoma | 0.98 ± 0.28 | 0.57 ± 0.01 |
| A549 | Non-small-cell lung carcinoma | 1.54 ± 0.08 | 1.33 ± 0.19 |
| MCF-7 | Breast carcinoma | 1.10 ± 0.09 | 1.33 ± 0.36 |
| TSGH | Gastric carcinoma | 2.09 ± 0.09 | 2.10 ± 0.11 |
| MKN-45 | Gastric carcinoma | 1.25 ± 0.04 | 2.51 ± 0.81 |
| HT-29 | Colorectal carcinoma | 0.72 ± 0.19 | 1.24 ± 0.40 |
| PC3 | Prostate carcinoma | 1.74 ± 0.31 | 1.63 ± 0.41 |

Inhibition by Compounds 5b and 14a in twenty-four cell lines are shown in Table 3 below.

TABLE 3

$IC_{50}$ values of 5b and 14a against human cancer cell lines

| | | $IC_{50}$ ± SD (nM) | | |
|---|---|---|---|---|
| Cell line | Tissue origin | SAHA | 5b | 14a |
| KB | Oral carcinoma | 868 ± 219 | 86.6 ± 17.1 | 252 ± 58.5 |
| KB-VIN10 | KB resistant | 1848 ± 526 | 85 | 213 |
| KB-7D | KB resistant | 1098 ± 126 | 139 ± 26.8 | 276 ± 78.4 |
| KB-L30 | KB-resistant | 1505 ± 532 | 175 ± 26.8 | 445 ± 249 |
| H460 | NSCLC | 980 ± 280 | 112.5 ± 9.5 | 243 ± 70.4 |
| HT29 | Colorectal carcinoma | 720 ± 190 | 85.4 ± 9.8 | 182 ± 26.7 |
| HONE-1 | Nasopharyngeal carcinoma | 1237 ± 159 | 447 ± 45.2 | |
| H9 | T cell lymphoma | | 55.4 ± 7.8 | |
| BJAB | B cell lymphoma | | 161 ± 20.3 | |
| SCC15 | Tongue carcinoma | | 176 ± 63.9 | |
| OECM-1 | Oral carcinoma | | 384 ± 72.1 | |
| MDA-MB-231 | Breast carcinoma | | 247 ± 9.3 | 184 ± 50 |
| MCF-7 | Breast carcinoma | 1100 ± 100 | | 170 ± 55 |
| DU-145 | Prostate carcinoma | 1070 ± 40 | 90 ± 30 | 420 ± 170 |
| PC3 | Prostate carcinoma | 2740 ± 140 | 170 ± 40 | 380 ± 220 |
| LNCaP-104 | Prostate carcinoma | 1950 ± 70 | 180 ± 70 | |
| LNCaP-R1 | Prostate carcinoma | 2100 ± 90 | 150 ± 30 | 156 ± 40 |
| LNCaP-R2 | Prostate carcinoma | 760 ± 30 | 100 ± 40 | 141 ± 50 |
| HUVEC | (Normal: endothelial) | | 62.0 ± 2.8 | |
| K2 | (Normal: keratinocyte) | | 447 ± 37.3 | |
| K6 | (Normal: keratinocyte) | | 545 ± 39.0 | |
| Detroit551 | (Normal: fibroblast) | >5000 | 707 ± 64.7 | >1000 |
| RWPE-1 | (Normal: prostate) | | 240 ± 108 | |
| WI-38 | (Normal: lung) | >5000 | 272 ± 52.3 | >1000 |

Two/Three Dimensional Cell Growth Inhibitory Assay

Compounds 5b and 7 were subjected to two/three dimensional cell growth inhibitory assays following the procedure described below.

For the two dimensional assay, cancel cells in the logarithmic phase were cultured in complete medium in 96-well plates at 37° C. with 5% $CO_2$ for overnight incubation, and treated with various concentrations of test compounds for three generative times. Cells were then incubated with a serum free medium containing 3-(4,5-dimethylthiazol-2-yl)-2,5-diphenyltetrazolium bromide (MTT) at a final concentration of 0.5 mg/mM for four hours. MTT was converted to formazan by metabolically viable cells. Formazan was then soublized in 50% DMF solution containing 20% SDS at 37° C. overnight. Absorbance was measured at 570 nm using a spectramax M5 microplate reader (Molecular Devices, UK).

For the three dimensional assay, cells in the logarithmic phase were cultured in 50% Matrigel-containing complete medium in 96-well plates at 37° C. with 5% $CO_2$ for five days incubation, and treated with appropriate concentrations of test compounds for three generative times. Images of spheroids were taken under a microscope, and spheroid cell survival was determined by MTT assays.

The results are shown in Tables 4-7 below.

TABLE 4

Compound 7 compared with Paclitaxel, Vincristine, Adriamycin, and SAHA

| Compound | 2D Culture | 3D Culture | Resistance (3D/2D) |
|---|---|---|---|
| Paclitaxel (nM) | 0.2 ± 0.1 | 5,850 ± 70 | 29,250 |
| Vincristine (nM) | 0.75 ± 0.64 | 2.5 ± 0.71 | 3.33 |
| Adriamycin (μM) | 0.07 ± 0.03 | 0.72 ± 0.04 | 10.3 |
| SAHA (μM) | 2.74 ± 0.14 | 4.63 ± 0.11 | 1.69 |
| 7 (μM) | 2.99 ± 0.17 | 6.38 ± 0.16 | 2.13 |

TABLE 5

Compound 7 $IC_{50}$ values against prostate cancer cells

| Culture | Cell Line | Cell Properties | SAHA (μM) | 7 (μM) |
|---|---|---|---|---|
| 2D | Du145 | Androgen-independent | 1.07 ± 0.04 | 1.22 ± 0.05 |
| | LNCaP104-S | Androgen-dependent | 2.10 ± 0.09 | 1.98 ± 0.1 |

TABLE 5-continued

Compound 7 IC$_{50}$ values against prostate cancer cells

| Culture | Cell Line | Cell Properties | SAHA (μM) | 7 (μM) |
|---|---|---|---|---|
| | LNCaP104-R1 | Androgen-independent | 0.76 ± 0.03 | 1.15 ± 0.03 |
| | LNCaP104-R2 | Androgen-independent | 1.95 ± 0.07 | 2.09 ± 0.11 |
| 3D | LNCaP104-S | Androgen-dependent | 4.6 ± 0.12 | 3.21 ± 0.15 |
| | LNCaP104-R1 | Androgen-independent | 2.45 ± 0.1 | 2.45 ± 0.15 |

Table 5 above shows antitumoral effect of Compound 7 and SAHA on 2D cell culture and 3D cellular sphere culture of prostate cancer cells. In the 2D culture, cells were cultured in complete medium for overnight; in the 3D cellular sphere culture, cells were cultured in a semi-solid culture medium comprised of GFR-Matrigel™ (BD Biosciences, Cat. #356231) and complete medium (v:v=1:1) for five to seven days to allow the formation of three dimensional cellular spheres. The cells (in the 2D culture) and the cellular spheres (in the 3D culture) were treated with test compounds for 72 hours, and then subjected to the MTT colorimetric assay. Each value represents the mean of three independent experiments. Cellular spheres formed in semi-solid and drug effect on cellular spheres were examined using phase-contrast light microscopy. Compound 5b had a similar anti-proliferative activity in both the two and three dimension cell culture system in human prostate carcinoma cells.

TABLE 6

Compound 5b compared with Pclitaxel, Vincristine, Adriamycin, and SAHA

| Compound | IC50 value | | Resistance |
|---|---|---|---|
| | 2D Culture | 3D Culture | (3D/2D) |
| Paclitaxel (nM) | 0.2 ± 0.1 | 5850 ± 70 | 29250 |
| Vincristine (nM) | 0.75 ± 0.64 | 2.5 ± 0.71 | 3.33 |
| Adriamycin (μM) | 0.07 ± 0.03 | 0.72 ± 0.04 | 10.3 |
| SAHA (μM) | 2.74 ± 0.14 | 4.63 ± 0.11 | 1.69 |
| 5b (μM) | 0.17 ± 0.04 | 0.41 ± 0.06 | 2.41 |

TABLE 7

Compound 5b IC$_{50}$ values in a two and three dimension cell culture system in human prostate cancinoma cells

| | | MTT IC$_{50}$ ± SD (μM) | |
|---|---|---|---|
| Culture | cell line | SAHA | 5b |
| 2D | PC3 | 2.74 ± 0.14 | 0.17 ± 0.04 |
| | Du145 | 1.07 ± 0.04 | 0.09 ± 0.03 |
| | LNCaP104-S | 2.10 ± 0.09 | 0.15 ± 0.03 |
| | LNCaP104-R1 | 0.76 ± 0.03 | 0.10 ± 0.04 |
| | LNCaP104-R2 | 1.95 ± 0.07 | 0.18 ± 0.07 |
| 3D | PC3 | 4.63 ± 0.11 | 0.41 ± 0.06 |
| | LNCaP104-S | 4.6 ± 0.12 | 0.23 ± 0.03 |
| | LNCaP104-R1 | 2.45 ± 0.1 | 0.15~0.625 |

Compound 7 was tested for its antitumoral effect against PC3 prostate cancer cells grown in a 3D culture. More specifically, cellular spheres formed in semi-solid and drug effect on cellular spheres were examined using phase-contrast light microscopy. 3D structures of cells were analyzed using 4× magnification, 10× magnification, and 20× magnification. Compound 7 disrupted the spheroid structure of PC3 tumors in a concentration-dependent manner. The cytotoxic effect of compound 7 was potent in both a 3D spheroid culture and a 2D culture.

SDS-PAGE and Western Blot Analysis

Compounds 7, 5b, and 14a were subjected to the SDS-PAGE and the western blot analysis following the procedures described below.

More specifically, cells in the logarithmic phase were initially seeded at a density of $1 \times 10^6$ in 100 mm$^2$ dishes. After treatment with test compounds at various concentrations (i.e., 0.5×, 1×, 2×, and 4×IC$_{50}$; IC$_{50}$ indicia of compound in vitro potency) for the indicated times (i.e., 24 and 48 hours), adherent cells were collected for protein extract preparation. Briefly, cells were lysed with the cell lysis reagent CelLytic™ M (Sigma-Aldrich) containing 1 mM DTT, 1 mM PMSF and protease inhibitors for whole-cell lysate preparation. Equal amounts of lysate (on a protein basis) were then differentiated using the SDS-PAGE, blotted on PVDF membranes, conjugated with various specific primary antibodies, and then probed with appropriate secondary antibodies. The immunoreactive bands were detected using the ECL method and visualized on Kodak Bio-MAX MR film.

Proteins from cells were extracted and subjected to the western blotting analysis. β-Actin was used as an internal control. The deacetylase enzyme assay was based on a homogeneous fluorescence release assay. Purified recombinant HDAC enzymes were incubated with substrates and test compounds at various concentrations (i.e., 1 nM, 10 nM, 100 nM, and 1000 nM for Compounds 7 and 5b; 0.5×, 1×, 2×, and 4×IC$_{50}$ for Compound 14a) for 24 hours. After fluorophore from the deacetylated substrates, fluorescent signal was detected.

Compound 7 inhibited HDAC1-10 activities in PC3 cells in a concentration-dependent manner for 48 hours.

In a 24-hour study, Compound 5b induced inhibition of HDAC 1 and HDAC2 at 50 nM or lower and induced inhibition of HDAC6 at about 100 nM.

Compounds 7, 5b, and 14a all induced histone and α-tubulin acetylation in PC3 cells in a concentration-dependent manner. Further, Compound 5b also induced histone and α-tubulin acetylation in human BJAB B cell lymphoma and MDA-MD-231 breast carcinoma; and Compound 14a also induced histone and a-tubulin acetylation in human DU145 cells.

Cell Cycle Analysis

Compounds 7, 5b, and 14a were subjected to cell cycle analysis following the procedure described below.

More specifically, cells in the logarithmic phase were initially seeded at a density of $1 \times 10^6$ in 100 mm$^2$ dishes. After treatment with various concentrations of test compounds for the indicated times, cells were trypsinized, washed with PBS, and fixed in 70% ethanol. The fixed cells were then treated with 50 μg/mL RNase and stained with 50 μg/mL propidium iodide at room temperature for 20 minutes. The DNA content was determined by BD FACS Calibur flow cytometry system (BD Biosciences). For each analysis, 10,000 cells were counted, and the percentage of cells in each phase was calculated using ModFit LT software (Verity Software House, Inc.).

Human androgen-independent PC3 prostate cancer cells were treated with Compounds 7, 5b, and 14a at various doses (i.e., 0.5×, 1×, 2×, 4×, and 8×IC$_{50}$) for different durations (i.e., 24 and 48 hours for Compounds 7 and 5b; 6, 12, 24, and 48 hours for Compound 14a).

Compounds 7, 5b, and 14a all induced cell cycle arrest and apoptosis in androgen-independent PC3 prostate cancer cells. Compound 5b also induced p21 up-regulation.

Cell Proliferation in C6 Glioma In Vitro

The rat C6 glioma cell line was treated with Compound 7 and analyzed following the procedure described below.

C6 glioma cell line was obtained from American Type Culture Collection. Cultured cells were treated with either vehicle or Compound 7 for 24, 48, or 72 hours and further measured by the MTT assay (Liu et al., *Toxicol. Res.,* 2015). Briefly, cells were incubated with 0.25 mg/mL MTT (Sigma) at 37° C. for 1 hr and the MTT fomazan was measured spectrophotometrically (μQuant, Bio-Tek) at 595 nm after dissolution of the crystals in DMSO.

For cell cycle analysis, C6 glioma cell line was pre-treated with Compound 7 at various concentrations for the indicated times (see "Cell cycle analysis", supra). After the treatment, cells were further trypsinized, washed with PBS, and fixed in 70% ethanol. The fixed cells were then treated with RNase and stained with 50 mg/mL propidium iodide at room temperature for 20 minutes. The staining fluorescence intensity indicating the DNA content was determined by a BD FACS Calibur flow cytometry system (BD Biosciences). For each analysis, 10,000 cells were counted, and the percentage of cells in each phase (i.e., SubG1, G0-G1, S, or G2-M) was calculated.

Unexpectedly, Compound 7 inhibited the cell proliferation in a concentration-dependent manner and showed about 50% inhibition of cell proliferation at 30 uM. By contrast, SAHA, a HDAC6 inhibitor, did not exert any inhibition at the same concentration.

Cell Death in C6 Glioma In Vitro

The rat C6 glioma cell line was treated with Compound 7 and analyzed following the procedure described below.

Cell death was analyzed by a lactate dehydrogenase (LDH) assay. The culture medium was centrifuged after the experiment and the activity of LDH released into culture media was detected with a LDH cytotoxicity detection kit (Roche). The percentage of cytotoxicity was determined by the equation: [(Experimental group−Control group)/(Triton-100-treated group (100% maximal death)−Control group)]× 100%. The test compound was found to induce the cell death in a concentration-dependent manner. It unexpectedly showed about 100% induction of cell death at 30 uM after 3 days, compared with about 70% induction by SAHA.

Cell Viability in Human Glioblastoma (U87MG or GBM8401) In Vitro

U87MG human glioblastoma cell line was treated with Compound 7 and analyzed following the procedure described below.

Cell viability was assessed by an MTT assay. Briefly, cells were incubated with 0.25 mg/mL MTT (Sigma) at 37° C. for 1 hour and the MTT fomazan were measured spectrophotometrically (μQuant, Bio-Tek) at 595 nm after dissolution of the crystals in DMSO.

Compound 7 reduced viability of human glioblastoma (U87MG or GBM8401) cells in a concentration-dependent manner and showed about 70% reduction of the cell viability at 30 uM.

In Vivo HDAC Inhibitory Assay

Compound 7 was subjected to an in vivo HDAC inhibitory assay in mice following the procedure described below.

More specifically, the antitumor effect of Compound 7 was examined in the human PC3 xenografted mice. Subcutaneous inoculation of 5×10⁶ PC3 cells in specific pathogen-free male athymic mice (strain BALB/cAnN.Cg-Foxn1nu/CrlNarl) from the National Laboratory Animal Center, Taiwan, was applied. The mice were subsequently fed under specific pathogen-free conditions and provided with sterile water and food. When the tumor volume reached 150 to 200 mm³, mice were assigned to groups randomly and treated with a vehicle control and 25 mg/kg Compound 7 for 4, 8, and 24 hours (n=3) by oral administration, and then sacrificed at the time indicated. Tumor samples were obtained and frozen in liquid nitrogen before storage in −80° C. Tumor proteins were extracted and subjected to the Western blotting analysis. β-Actin was used as an internal control.

Compound 7 was effective at 25 mg/kg in inhibiting HDACs by monitoring p21, p27, histone, and α-tubulin acetylation in the PC3 xenograft model.

In Vivo Antitumor Activity Assay

Compounds 7 and 5b were tested in an in vivo antitumor activity assay following the procedure described below.

The antitumor effect of the two test compounds were examined in mice xenografted with human PC3 prostate cancer cells or HCT116 colorectal cells.

Five million PC3 cells were subcutaneously inoculated into specific pathogen-free male athymic mice (strain BALB/cAnN.Cg-Foxn1nu/CrlNarl) from the National Laboratory Animal Center, Taiwan. Mice were subsequently fed under specific pathogen-free conditions and provided with sterile water and food. When the tumor volume reached 150 to 200 mm³, mice were assigned to groups randomly and treated with vehicle control or Compound 7 or 5b at 25/50/100 mg/kg. The compound was administered once a day, 5 days/week for 2 weeks (n=6) by oral administration. Tumor volume and body weight change were measured twice a week. At the end of the experiments (day 25 after first dosing), animals were euthanized in a $CO_2$-containing chamber, and the tumors were collected and fixed in formaldehyde. The terminal deoxynucleotidyl transferase-mediated dUTP nick end labeling assay (TUNEL) was conducted for apoptosis detection. Tumor tissue sections were analyzed using a FITC In Situ Cell death detection kit (Roche) and fluorescence microscopy. Tissue treated with DNase was used as the positive control. Green fluorescence labeled nucleus indicates the induction of DNA fragmentation.

Compounds 7 inhibited human PC3 xenograft growth by about 50% at both 25 mg/kg and 50 mg/kg at day 25 after the first dosing without causing much body weight change.

Compounds 7 also inhibited human colorectal HCT116 xenograft growth by about 50-60% at 25 mg/kg, 50 mg/kg, and 100 mg/kg at day 22 after the first dosing, again without causing much body weight change.

Compounds 5b inhibited human PC3 xenograft growth by about 70% at 50 mg/kg at day 29 after the first dosing. Unexpectedly, Compounds 5b completely inhibited human PC3 xenograft growth at 100 mg/kg and achieved tumor regression from day 8 to day 29 after the first dosing.

In Vivo Antitumor Activity of Compound 7 Against Human Glioblastoma Xenograft Tumor The antitumor effect of Compound 7 was examined in human glioblastoma (U87-MG-LucNeo cells) on the xenografted mouse model. A HDAC6 inhibitor, i.e., SAHA, and clinically first-line and anti-glioblastoma drug temozolomide (TMZ) were used for comparison.

Male athymic nude mice at 5-6 weeks old were obtained from BioLasco (Taiwan) and maintained in a specific-pathogen-free facility. All experimental procedures were approved by the Institute of Animal Care and Use Committee of Taipei Medical University. Each nude mouse was anesthetized with an i.p. injection of xylazine (Sigma) and zolazepam (Zoletil 50, Virbac), and then secured in a stereotaxic frame. Luciferase expressing U87 cells (10⁶ cells in PBS) was intracranially implanted into the right striatum as previously described (Liu et al., *Toxicol. Res.*, 2015). One week after implantation, Nude mice were treated with TMZ (50 mg/kg. p.o.), SAHA (150 mg/kg, p.o.) or Compound 7 (50-100 mg/kg, p.o.) and their survival rates were analyzed in 4 groups including a vehicle group. Survival analyses showed that Compound 7 unexpectedly extended survival longer than TMZ.

Orthotopic Tumor Size Measurement

Another parallel set of xenografted nude mice treated with drug or vehicle treatment as described above were used in this experiment.

A bioluminescence IVIS 2000 imaging system was used to measure tumor size in vivo as previously described (Liu et al., *Toxicol. Res.*, 2015). Imaging analysis revealed that a low dose of Compound 7 (25 mg/kg) decreased the tumor size more than a higher dose of SAHA (150 mg/kg) or the same dose of TMZ (25 mg/kg).

Other Embodiments

Without further elaboration, it is believed that one skilled in the art can, based on the above description, utilize the present invention to its fullest extent. All publications cited herein are incorporated by reference.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention also can be made and screened for inhibitory activity against indoleamine 2,3-dioxygenase (IDO)/tryptophan 2,3-dioxygenase (TDO) and for treating IDO/TDO associated conditions. Thus, other embodiments are also within the claims.

What is claimed is:

1. A compound of formula (I):

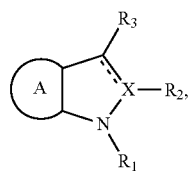
(I)

wherein
$R_1$ is $SO_2R_a$, in which $R_a$ is phenyl substituted with

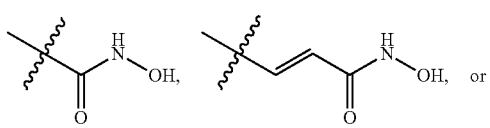

-continued

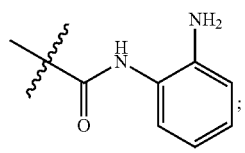

$R_2$ is H;
$R_3$ is H;
X is C;
A is unsubstituted pyridine; and
═ is a double bond, or a pharmaceutically acceptable salt or solvate thereof.

2. The compound of claim 1, wherein the compound is selected from the group consisting of the following compounds:

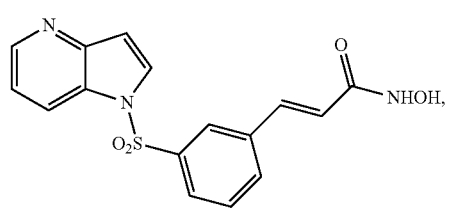
5

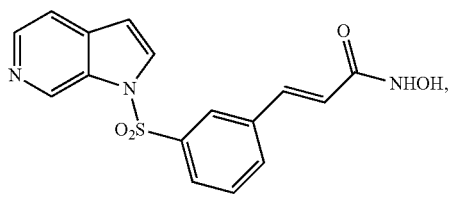
6

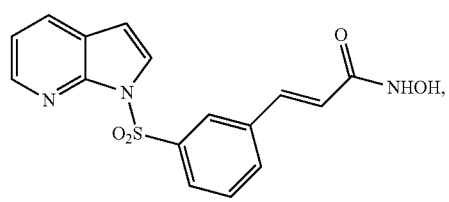
7

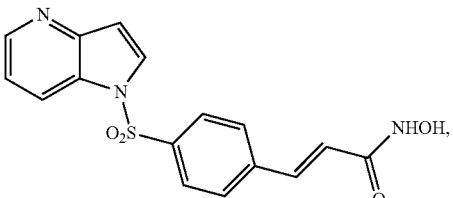
10

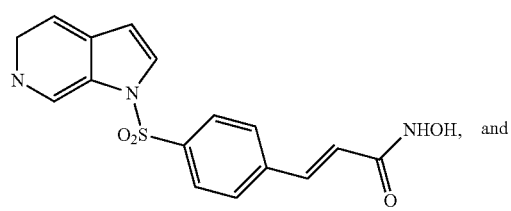
11

-continued

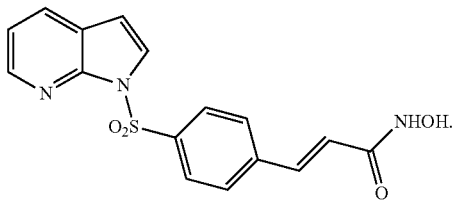

3. The compound of claim 2, wherein the compound is

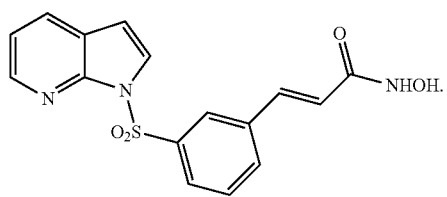

4. A pharmaceutical composition comprising a compound of claim 1 and a pharmaceutically acceptable carrier.

5. A method of alleviating, relieving, altering, ameliorating, improving, or affecting cancer comprising administering to a subject in need thereof an effective amount of a compound of claim 1.

6. The method of claim 5, wherein the cancer is glioma, prostate cancer, colorectal cancer, breast cancer, non-small-cell lung cancer, gastric cancer, oral cancer, nasopharyngeal cancer, T cell lymphoma, or B cell lymphoma.

7. The method of claim 6, wherein the cancer is glioma, prostate cancer, or colorectal cancer.

8. The method of claim 5, wherein the compound is orally administered to a subject in need thereof.

9. The method of claim 8, wherein the compound is administered once a day.

* * * * *